(12) United States Patent
Monassevitch et al.

(10) Patent No.: US 7,635,374 B2
(45) Date of Patent: Dec. 22, 2009

(54) ENDOSCOPIC FULL THICKNESS RESECTION USING SURGICAL COMPRESSION CLIPS

(75) Inventors: Leonid Monassevitch, Hadera (IL); Boaz Shenhav, Tel Aviv (IL); Boaz Harari, Tel Aviv (IL); Amir Perle, Haifa (IL); Michael Arad, Tel Aviv (IL); Shahar Millis, Pardes Hanna (IL); Kobby Greenberg, Even Yehuda (IL); Alex Geller, Kfar Saba (IL); Amir Szold, Tel Aviv (IL); Shlomo Lelcuk, Savion (IL); Doron Kopelman, Caesarea (IL); Amol Bapaye, Pune (IN); Dror Rosner, Holon (IL)

(73) Assignee: NITI Surgical Solutions Ltd., Netanya (IL)

( * ) Notice: Subject to any disclaimer, the term of this patent is extended or adjusted under 35 U.S.C. 154(b) by 150 days.

(21) Appl. No.: 11/647,912

(22) Filed: Dec. 29, 2006

(65) Prior Publication Data
US 2007/0213585 A1 Sep. 13, 2007

Related U.S. Application Data

(60) Provisional application No. 60/780,446, filed on Mar. 9, 2006.

(51) Int. Cl.
*A61B 17/10* (2006.01)
*A61B 17/08* (2006.01)
*A61B 1/00* (2006.01)
(52) U.S. Cl. .................. 606/142; 606/157; 600/104

(58) Field of Classification Search ............... 606/127, 606/142, 151, 153, 157, 158; 600/104–107, 600/204
See application file for complete search history.

(56) References Cited

U.S. PATENT DOCUMENTS

| | | | | |
|---|---|---|---|---|
| 4,038,987 | A * | 8/1977 | Komiya | 606/142 |
| 5,196,003 | A * | 3/1993 | Bilweis | 600/204 |
| 5,423,830 | A * | 6/1995 | Schneebaum et al. | 606/127 |
| 5,725,542 | A * | 3/1998 | Yoon | 606/157 |
| 6,264,086 | B1 | 7/2001 | McGuckin, Jr. | |
| 6,352,503 | B1 | 3/2002 | Matsui et al. | |
| 6,527,753 | B2 * | 3/2003 | Sekine et al. | 600/104 |
| 6,629,630 | B2 | 10/2003 | Adams | |
| 6,695,198 | B2 | 2/2004 | Adams et al. | |
| 6,820,791 | B2 | 11/2004 | Adams | |
| 6,840,423 | B2 | 1/2005 | Adams et al. | |
| 6,938,814 | B2 | 9/2005 | Sharma et al. | |
| 2004/0158263 | A1 | 8/2004 | McAlister et al. | |
| 2004/0215210 | A1 | 10/2004 | Duel | |
| 2005/0216036 | A1 | 9/2005 | Nakao | |

* cited by examiner

*Primary Examiner*—Julian W Woo
(74) *Attorney, Agent, or Firm*—Pearne & Gordon LLP

(57) ABSTRACT

A system including surgical compression clips is described and used for endoscopic full thickness resection. Similarly, methods for endoscopic full thickness resection using the described system are also discussed. Surgical compression clips using shape-memory elements are discussed. These clips are advanceable to the site of suspect tissue to be resected through a lumen of a multi-lumen sleeve encasing an endoscope. At the site of the tissue, the compression clip is opened and operated to circumscribe the suspect tissue. Grasper assemblies, advanceable through an endoscope, are also described. These latter grasp and bring the suspect tissue to the open clip. The clip is then closed and the tissue resected. The clip effects necrosis and healing at the resected site.

24 Claims, 70 Drawing Sheets

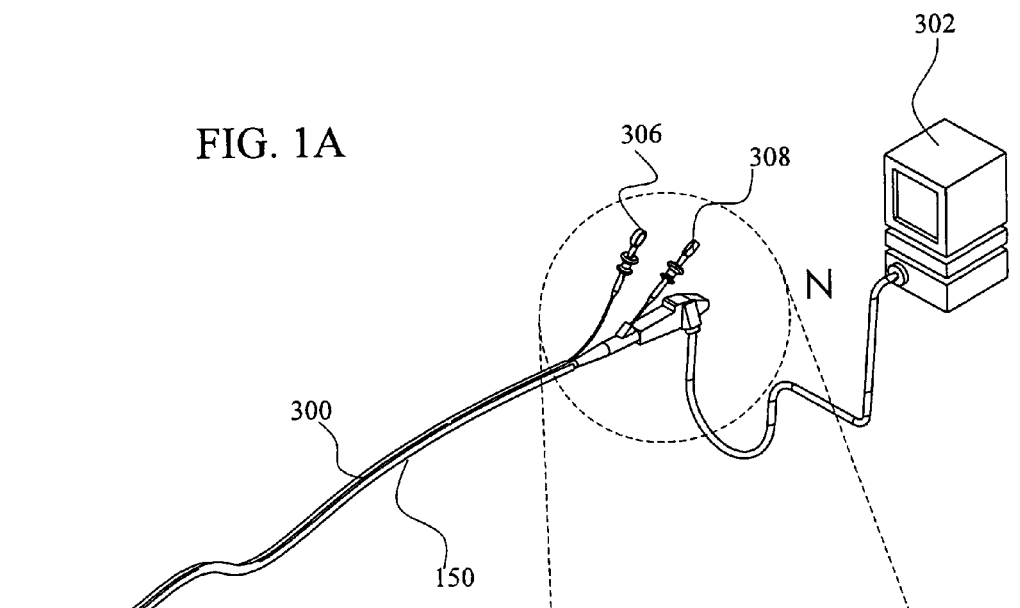
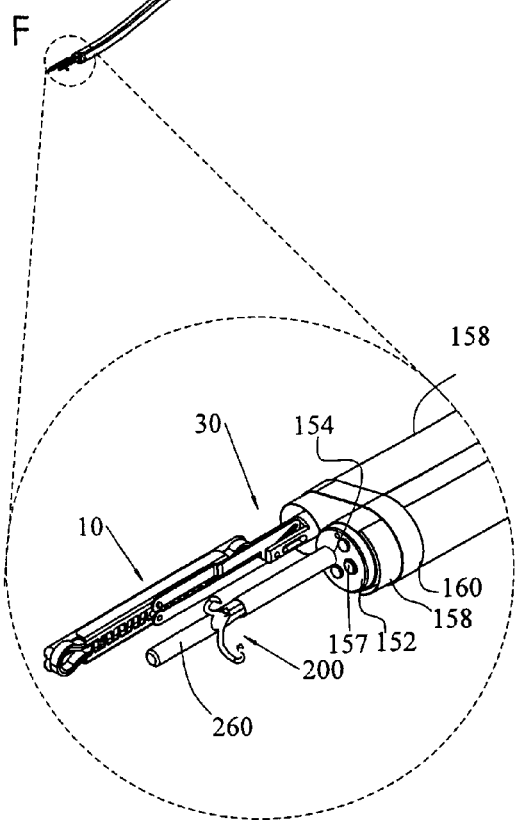
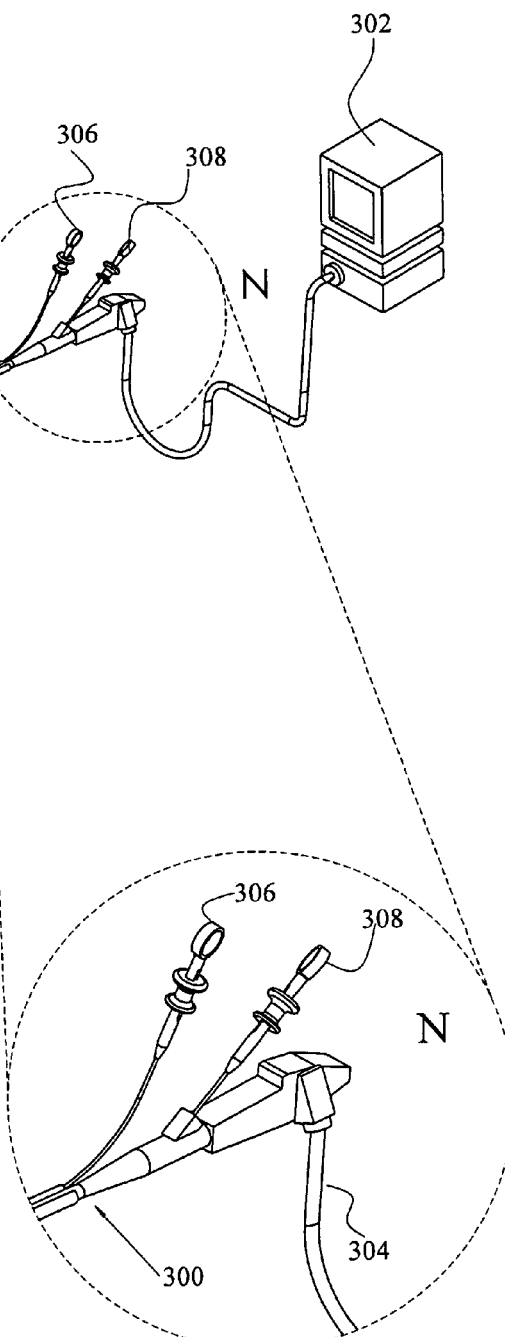
FIG. 1A
FIG. 1B
FIG. 1C

ENDOSCOPIC FULL THICKNESS RESECTION USING SURGICAL COMPRESSION CLIPS

CROSS REFERENCE TO RELATED APPLICATION

This application claims the benefit of U.S. Provisional Application No. 60/780,446, filed Mar. 9, 2006.

FIELD OF THE INVENTION

The present invention relates to a method and a system and subsystems thereof for endoscopic full thickness resection surgical procedures, typically of the gastrointestinal (GI) tract.

BACKGROUND OF THE INVENTION

Polyps are defined as growths or masses protruding from a mucous membrane of the body. Polyps may be classified by their morphology. A polyp may be attached to a mucous membrane by a stalk (pedunculated polyp) or the polyp may have a broad base (sessile polyp). They may occur in the mucous membrane of many different types of organs, such as the nose, mouth, stomach, intestines, rectum, urinary bladder, and uterus. Most polyps are benign and eventually stop growing, but some, may ultimately become cancerous tumors.

The probability of any single polyp becoming cancerous depends on its gross appearance, histological features, and size. Polyps greater than 1 centimeter have a greater risk of being or becoming cancerous than polyps smaller than 1 centimeter. As these tumors grow larger, they can invade the underlying tissue layers supporting the polyp. In the final stages, the cancer may metastasize to other distant organs. Particularly common, yet readily treatable, are polyps of the colon. Colorectal or gastric cancers, often beginning as benign or precancerous polyps, can essentially be avoided if detected and treated in their early stages by performing a polypectomy.

Polypectomy is the medical term for removing polyps, particularly small polyps of the colon and stomach. These can be removed by using a biopsy forceps, which removes small pieces of tissue. Larger polyps are usually removed by putting a noose, or snare, around the polyp base or stalk and burning through the tissue with an electric instrument (cauterization). Other devices employ physical or electrical scraping of the lining of an organ, such as the colon, rectum or stomach, to remove a polyp.

In almost all cases, the severed polyps are retrieved for examination by a pathologist. For decisively ruling out cancer, a sample of adequate size is required for the pathology laboratory. This includes a clean margin around the polyp as well as all the layers of the organ wall.

Complications, however, sometimes occur during polypectomies. Electrocauterization, for example, often produces desiccation and perforation of the organ wall. Other complications include non-specific tissue destruction caused by unnecessary heating in the treatment environment resulting from the presence of saline, a highly conductive electrolyte. Finally, conventional electrosurgical cutting or resecting devices tend to leave the operating field cluttered with tissue fragments that have been resected from the target tissue. These tissue fragments make observation of the surgical site extremely difficult.

An endoscopist's ability to resect large sessile polyps is limited, due to the inherent limitations of endoscopes, the lack of polyp accessibility, the lack of available accessories, and the difficulty in achieving full thickness resection. While colonoscopes/gastroscopes are widely used for diagnostic purposes their therapeutic abilities are limited. This is a result of the need to control and manipulate instruments, including the endoscope's distal end, from outside the body. Because of the limitations in current technology, large polyps that cannot be resected endoscopically, or polyps suspected to be malignant, are referred to surgery.

Prior art snare instruments used in polypectomies have several problems. First, it is difficult for the physician to precisely position the snare. Typically, it is necessary for the physician to repeatedly push, pull, and torque the sheath and the shaft of the instrument in order to position the snare around the polyp. Second, prior art instruments are not capable of efficient steering, because the shaft generally used includes a cable having low torsional stiffness. Third, while several attempts have been made at providing a snare instrument with a handle adapted to more adeptly steer the snare, most such prior art instruments do not specifically allow for rotating the snare so as to position it relative to the polyp. Rather, the physician must rotate the shaft of the instrument by tightly gripping and rotating the sheath where it enters the endoscope in an effort to try to maneuver the snare over the polyp.

Mechanical surgical clips for use in endoscopic surgery are known; however, they too have drawbacks. The typical known clip is a two legged clip that is passed through an endoscope's working channel via a flexible delivery catheter. Because the clip needs to pass through the endoscope, the clip's size is limited. Size limitations prevent the clip from being able to clamp off all of the vessels in the tissue around a wound. Additionally, the clip is unable to provide sufficient clamping force because of its structural design. An additional problem with these clips is that when delivering these clips to the wound site, good visualization of a bleeding vessel cannot be obtained. The endoscopist may be required to blindly attach the clip, resulting in an imprecisely performed procedure that requires guess work on the part of the endoscopist.

Currently, there are two endoscopic techniques used to resect large polyps. However, these are complicated, require significant experience and instrumentation, may be associated with complications and require repeated procedures to achieve complete resection. Determining the pathology of the lesion is usually limited because of the endoscopists' inability to perform a full thickness resection. In one technique, the piecemeal technique, a snare is used to remove the polyp piece by piece. In many cases this procedure needs more than one session to completely resect the polyp. The samples sent for pathology using this technique have the following drawbacks: loss of orientation of the resected tissue (polyp), inability to identify infiltration beyond the mucosa to diagnose malignant changes, inability to conclusively comment on the margins of resection, and inability to judge completeness of the resection. This leads to frequent follow-up endoscopic surveillance, adding to patient discomfort and extra costs to the health care system.

The second and more advanced technique is mucosectomy. With this technique the polyp is first elevated from the submucosa using a submucosal injection of a variety of solutions. The polyp is then excised using a variety of knives and/or snares. This procedure requires experience with advanced endoscopic techniques and may be associated with serious complications such as bleeding and perforation, complications that may result in surgery and hospitalization. A prerequisite for a safe mucosectomy is that the polyp should not invade the submucosa. Evaluation by high frequency intraluminal endosonography is mandatory prior to performing a mucosectomy, a procedure available at only a limited number of endoscopy centers throughout the world. Although lateral margins can be commented upon in a specimen obtained through mucosectomy, evaluation of the deeper margin of the specimen may still be in adequate.

An optimal solution would involve the resection of the entire polyp together with adequate margins (i.e. surrounding normal tissue) and the various layers of the polyp's adjacent organ wall, mucosa, submucosa, muscular propria layer and serosa (Full Thickness Resection). The tissue deficit should be endoscopically closed at the same time. To date, the only full thickness resection systems, sub-systems and methods discussed in the patent literature employ surgical staples. Staples often lead to undesired complications such as leakage of blood and other body liquids into the region of the resected polyp, particularly polyps of the colon, often resulting in severe infection. Other complications include strictures and inflammatory reactions to the foreign bodies left behind.

An additional problem with staple systems and methods is that they require a stapling mechanism which generally is relatively large and fairly rigid. This limits the maneuverability of an endoscope and does not allow approach to all locations.

Therefore, there remains a need for a method, a system and elements of a system which would facilitate full thickness resection without the drawbacks discussed above.

DEFINITIONS

"Proximal" relates to the side of the endoscope or devices closest to the user, while "distal" refers to the side of the endoscope or devices furthest from the user. Similarly, "proximal" refers to the side of the multi-lumen sleeve encasing the endoscope or of the working instruments associated with the endoscope or endoscopic system closest to the user and "distal" refers to the side furthest from the user.

"Polyp" as used in the specification and claims below is not intended to restrict the system, subsystems, elements and method discussed herein to polyps alone. Other types of suspect lesions may also be resected using the system, subsystems, elements and method discussed herein.

"Lesion" may be used in place of the word "polyp" without any intent at differentiating between the terms except where specifically indicated.

"Gastrointestinal tract" or its equivalents are used in the specifications and claims without the intent of being limiting. Other organ systems, and lesions found therein, are also contemplated as being treatable with the system, subsystems, elements and methods discussed in the present specification.

"Full thickness resection" and its equivalent "full transmural resection", both abbreviated as FTR, are used in the specification and claims without any intent at differentiating between these terms except where specifically indicated.

"Hinge spring" is a force applier and this latter term may be used herein interchangeably with hinge spring without any intent at differentiating between these terms, except where specifically indicated. Accordingly, the latch described herein, as well as elements having other shapes, may also be considered force appliers if they are used for, and their operation are based on, their possessing the properties of shape-memory materials with which to apply force in a compression clip. "Force means" may sometimes be used as a synonym for "force applier" without any attempt at differentiating between them unless specifically indicated. Similarly, hinge member may be used as a synonym for hinge spring without any attempt at differentiating between them unless specifically indicated.

"Working conduit", when used in the specification and claims, may refer to a working channel of the endoscope or a secondary lumen of the sleeve whose primary lumen encases an endoscope's insertion shaft.

"Endoscope", as used herein, should be construed as including all types of invasive instruments, flexible or rigid, having scope features. These include, but are not limited to, colonoscopes, gastroscopes, laparoscopes, and rectoscopes. Similarly, the use of "endoscopic" is to be construed as referring to all types of invasive scopes.

SUMMARY OF THE INVENTION

It is an object of the present invention to provide a system and method for full thickness resection of a lesion, typically but without being limiting, a gastrointestinal lesion such as a polyp.

An additional object is to provide a system and method that can allow for complete full thickness resection in a single procedure rather than the more typical piecemeal procedures currently in use.

It is a further object to provide a system and method where no foreign bodies are left behind in the body cavity after healing of the tissue at the resected site is completed.

It is another object of the present invention to provide a system and method for full thickness resection using compression clips. The clips exert continuous compression on the resected site along a continuous line thereby preventing undesired post-surgery fluid leakage. Such a continuous line is impossible to attain when using surgical staples.

It is an object of the present invention to provide a system and method which ensures that complete closure of a resected site is indifferent to variations in tissue thickness typical of a specific organ.

It is a further object of the present invention to provide a method and system to reduce the risk of tissue perforation when all tissue layers proximate to a lesion are resected.

It is another object of the present invention to provide a grasper assembly which allows for full transmural, i.e. full thickness, resection of a lesion, typically but without being limiting, a gastrointestinal lesion, such as a polyp.

A further object of the present invention is to provide a grasper assembly at least part of which is made of a material having shape-memory properties, allowing large reversible deformations, which enable grasping a sufficient amount of tissue for a full thickness resection.

It is an object of the present invention to provide a system and method for full thickness resection that employs instruments of relatively smaller dimensions than the large bulky instruments currently used with resections employing staples. Smaller instruments permit easier advance of the instrument to the lesion site.

The endoscopic system, its sub-systems and elements, and the method described herein may find particular use in full thickness resections of a suspect lesion, such lesion arising in for example, but without intending to be limiting, the bowel, rectum, appendix, gallbladder, uterus, stomach esophagus, etc.

In one aspect of the present invention there is provided a system for performing a full thickness resection of a portion of an organ wall for use with a surgical compression clip. The clip comprises a pair of compression elements and one or more force applier elements, the latter formed of shape memory material. The clip has an open position and a closed position and is configured to receive a full thickness of an organ wall portion when in its open position. The one or more force applier element is operative to provide a force to the compression elements, the compressive elements are operative to apply a compression force to the organ wall portion when the clip is closed around the tissue so as to cause organ wall closure after resection of a portion of the organ wall. The system for performing a full thickness resection of a portion of an organ wall with a surgical compression clip comprises: an endoscope having an insertion shaft having one or more channels; a multi-lumen sleeve having a primary lumen encasing the endoscope insertion shaft, and one or more secondary lumens; a clip applier for advancing the clip through a working conduit and for positioning the clip near the tissue to be resected, wherein the working conduit is a preselected one of (i) the one or more channels of the insertion shaft and (ii) the one or more secondary lumens of the multi-lumen sleeve; a severing element for resecting tissue, selectably extendable through the working conduit so as to be brought into a position of operational proximity to tissue extending through the compression clip; and a grasper assembly selectably extendable through the working conduit, for engaging and pulling the full thickness of an organ wall portion through the clip when the clip is in its open position. The severing element is operable to resect the full thickness of the portion of the organ wall extending through the clip.

In one embodiment of the system for performing a full thickness resection of a portion of an organ wall, the clip applier includes: two arm elements selectably engageable with the compression clip each arm element having a slot and a pin hole; a position controlling element in mechanical communication with the arm elements, the position controlling element including a first and second pin, where the first pin passes through the position controlling element and the pin hole on each of the two arm elements and the second pin passes through the position controlling element and the slot on each of the arm elements; and an activating element in mechanical communication with and operable to move the second pin in the position controlling element, thereby to produce substantially scissor-like motion of the arm elements bringing them from their closed adjacent position to their open spaced apart position and vice versa; and thereby to cause the compression clip to move from its open position to its closed position and vice versa in tandem with the motion of the arm elements of the clip applier.

In another embodiment of the system for use with a compression clip, the clip includes a threaded bolt inside a compression element of the clip, the threaded bolt having a receiving aperture, and the clip applier includes: a head element mateably insertable into the receiving aperture on the threaded bolt inside the compression element of the compression clip; and an activator for rotating the head element, thereby to cause the threaded bolt to rotate and the clip to move from its open position to its closed position and vice versa depending on the direction of rotation.

In yet another embodiment of the system for use with a compression clip, the clip includes a compression element and one or more connector elements on each of two force applier elements, and the clip applier includes: two wires each connected to a connector element on a different one of the two force applier elements; and a pin passing through an anchor positioned in the compression element, one of the wires being wound around the pin, whereby the compression clip moves from its closed position to its open position when the wires are pulled and said clip moves from its closed position to its open position when the wires are released.

In an embodiment of the system for use with a compression clip the grasper assembly is comprised of: a grasper having a closed position and an open position where the grasper is comprised of: forceps arms for grasping and pulling the portion of the organ wall to be resected; and a wire in mechanical connection with and for controlling and maneuvering the forceps arms and for bringing the forceps arms from their closed position to their open position and vice versa; and the grasper assembly also includes a grasper transporting element for transporting the grasper in its closed position to a location near the portion of the organ wall to be resected whereat the grasper is ejected from the transporting element allowing the forceps arms to open to their open position. In cases of this embodiment one or both of the wire and the forceps arms includes a bend, the bend facilitating grasping and pulling the organ wall to be resected through the clip. In some instances of this embodiment one or both of the wire and the forceps arms is formed at least partially of a shape memory material.

In a further embodiment of the system for use with a compression clip, the grasper assembly is comprised of: a flexible resilient vacuum cup having a closed and an open position; a suction source for generating negative pressure; a conduit joining the vacuum cup to the suction source; a grasper transporting element for transporting the vacuum cup in its closed position to a location near the portion of the organ wall to be resected where the vacuum cup is ejected from the transporting element allowing the vacuum cup to open to its open position and an articulation means for bringing the vacuum cup, when in its open position, to the portion of the organ wall to be resected, for engaging the tissue under a suction force, and for subsequently pulling the tissue through the surgical clip.

In another aspect of the present invention, there is provided a second system for performing a full thickness resection of a portion of an organ wall, which comprises: an endoscope having an insertion shaft having one or more channels; a multi-lumen sleeve having a primary lumen encasing the endoscope insertion shaft, and one or more secondary lumens; a compression clip having an open position and a closed position, the clip configured to receive a full thickness of an organ wall portion therethrough when in the open position, and operative to apply a compression force thereto when closed thereabout, so as to cause organ wall closure after resection of a portion of the organ wall; a clip applier for advancing the clip through a working conduit and for positioning the clip near the tissue to be resected, wherein the working conduit is a preselected one of (i) the one or more channels of the insertion shaft and (ii) the one or more secondary lumens of the multi-lumen sleeve; a severing element for resecting tissue, selectably extendable through the working conduit so as to be brought into a position of operational proximity to tissue extending through the compression clip; and a grasper assembly selectably extendable through the working conduit, for engaging and pulling the full thickness of an organ wall portion through the clip when the clip is in its open position. The severing element is operable to resect the full thickness of the portion of the organ wall extending through the clip.

In an embodiment of the system in this second aspect of the present invention the compression clip further includes a pair of generally elongated compressing elements for compressing the site of the portion of the organ wall to be resected, the compressing elements formed and configured for being disengageably joined to the clip applier. In this embodiment, the compression clip includes one or more shape memory force applier elements formed of shape memory material, the elements operative for providing a force to the pair of compressing elements for compressing the portion of the organ wall to be resected held therebetween. In some instances of this embodiment the compressing elements and the shape memory force applier elements form a planar configuration in both the clip's open and closed positions and the compressing elements of the surgical clip apply to the portion of the organ wall to be resected a compressive force acting in the plane of the clip and in a line between the compressing elements. In other cases of this embodiment, the system further includes a pair of generally elongated securing elements and wherein the one or more shape memory force applier elements are positioned between, and in mechanical connection with the operatively associated securing and compressing elements, and wherein the one or more shape memory force applier elements and the pairs of securing and compressing elements all lie in substantially the same plane in both the first open and second closed positions of the clip. A line of securing for holding the portion of the organ wall to be resected is formed by, and tangent to, the securing elements and a line of compression for compressing the portion of the organ wall to be resected is formed by, and tangent to, the compression elements. The lines of securing and of compression are not collinear lines. In these embodiments the securing and compressing elements are generally linear elements.

In some embodiments of the system in the second aspect of the invention, the clip further includes a pair of generally elongated securing elements each having formed thereon a pair of mutually opposing gripping portions adapted to secure the portion of the organ wall to be resected between them, the securing elements operationally associated with the compressing elements. The securing elements are formed and configured for being disengageably joined to the clip applier. In some instances of this embodiment the gripping portions of the securing elements include toothed first edges which are in proximity to each other when the clip is in its closed position and wherein the toothed first edges of the securing elements are spaced apart from each other when the clip is in its open position. In some instances of this embodiment, the securing and compressing elements are substantially linear elements.

In another embodiment of the system of the second aspect of the present invention, the grasper assembly of the system is comprised of: a grasper having a closed and an open position, the grasper comprised of: forceps arms for grasping and pulling the portion of the organ wall to be resected; and a wire in mechanical connection with and for controlling and maneuvering the forceps arms and for bringing the forceps arms from their closed position to their open position and vice versa. The grasper assembly also includes a grasper transporting element for transporting the grasper in its closed position to a location near the portion of the organ wall to be resected whereat the grasper is ejected from the transporting element allowing the forceps arms to open to their open position. In some instances of this embodiment, one or both of the wire and the forceps arms includes a bend, the bend facilitating grasping and pulling the organ wall to be resected through the clip. In some instances of this embodiment, one or both of the wire and the forceps arms is formed at least partially of a shape memory material.

In another embodiment of the system of the second aspect of the present invention, the system includes a grasper assembly which comprises: a flexible resilient vacuum cup having a closed and an open position; a suction source for generating negative pressure; a conduit joining the vacuum cup to the suction source; a grasper transporting element for transporting the vacuum cup in its closed position to a location near the portion of the organ wall to be resected where the vacuum cup is ejected from the transporting element allowing the vacuum cup to its open position; and an articulation means for bringing the vacuum cup, when in its open position, to the portion of the organ wall to be resected for engaging the tissue under a suction force, and for subsequently pulling the tissue through the surgical clip.

In an embodiment of the system of the second aspect of the present invention, the clip further includes a pair of compressing elements and at least two shape memory force applier elements formed of shape memory material. One of the force applier elements is constructed as a latch which is operable to engage with an engagement means formed on one end of one of the pair of compressing elements. The latch thereby exerts a force on the portion of the organ wall to be resected when the portion of the organ wall is held between the compressing elements. In this embodiment the clip further includes a wire snare.

In another aspect of the present invention there is provided a method for performing a full thickness resection of a portion of an organ wall employing an endoscope, the method comprising the steps of: placing the endoscope in a body cavity and advancing the endoscope to and positioning it near the site of the portion of the organ wall to be resected; positioning a compression clip near the site of the portion of the organ wall to be resected; extending a grasping instrument for grasping the site of the organ wall to be resected and then operating the grasping instrument to grasp and pull all tissue layers of the organ wall portion to be resected into and through the compression clip so that full thickness resection may be effected; and severing the grasped tissue with a severing instrument while it is held by the compression clip.

In an embodiment of the method of the present invention the method further includes a step of opening the compression clip prior to the step of extending a grasping instrument and also further including a step of closing the compression clip prior to the step of severing.

In one embodiment of the method of the present invention, there is also included the step of rotating the grasped and pulled portion of the organ wall to be resected over and around a working instrument extended from the endoscope. The working instrument is configured, sized and positioned for having the tissue wrapped around it thereby ensuring that all tissue layers of the organ wall to be resected have been grasped.

In another embodiment of the method of the present invention the step of extending includes the step of grasping sufficient tissue to include large margins around the portion of the organ wall being resected.

In yet another embodiment of the method of the present invention, in the step of extending the grasping instrument is advanced and brought to the site of resection through a first secondary lumen of a multi-lumen sleeve and in the step of positioning the compression clip is advanced and brought to the site of resection through a second secondary lumen of the multi-lumen sleeve, wherein the primary lumen of the sleeve encases the endoscope and wherein the second secondary lumen is the secondary lumen closest to the portion of the organ wall to be resected.

In another embodiment of the method of the present invention, in the step of extending the grasping instrument and in the step of positioning the compression clip are both advanced and brought to the site of resection through the same secondary lumen of a multi-lumen sleeve wherein the primary lumen of the sleeve encases the endoscope and wherein the aforementioned secondary lumen is the secondary lumen closest to the portion of the organ wall to be resected.

In yet another embodiment of the method, in the step of extending the grasping instrument is advanced and brought to the site of resection through a working channel of the endoscope and in the step of positioning the compression clip is advanced and brought to the site of resection through a secondary lumen of the multi-lumen sleeve, wherein the primary lumen of the sleeve encases the endoscope and wherein the aforementioned secondary lumen is the secondary lumen closest to the portion of the organ wall to be resected.

In another embodiment of the method, the method further includes the step of activating a vacuum source so as to effect the action of grasping in the step of extending by a suction operated grasping instrument.

In yet another embodiment of the method, the severing instrument in the step of severing is advanced through the secondary lumen of a multi-lumen sleeve proximate to the secondary lumen through which the surgical clip is advanced, thereby allowing the tissue to be severed to be a few millimeters from the closed clip.

In another embodiment of the method of the present invention, the severing instrument in the step of severing is advanced through the same secondary lumen of a multi-lumen sleeve as the secondary lumen through which the clip is advanced.

In yet another embodiment of the method of the present invention, the severing instrument in the step of severing is advanced through the a working channel of the endoscope, and the clip is advanced through a secondary lumen of a multi-lumen sleeve, the secondary lumen being adjacent to the working channel through which the severing device is advanced.

BRIEF DESCRIPTION OF THE DRAWINGS

The present invention will be more fully understood and its features and advantages will become apparent to those skilled in the art by reference to the ensuing description, taken in conjunction with the accompanying drawings, in which:

FIG. 1A is an overall isometric view of an endoscopic system constructed according to the present invention;

FIG. 1B is an enlarged view of the distal end of the endoscopic system shown in FIG. 1A;

FIG. 1C is an enlarged view of the proximal end of the endoscopic system shown in FIG. 1A;

FIGS. 14 and 15 show isometric views of a second embodiment of a surgical compression clip constructed according to the present invention, wherein FIG. 14 and FIG. 15 show the clip in its closed and open positions, respectively;

Similar elements in the Figures are numbered with similar reference numerals.

DETAILED DESCRIPTION OF THE PREFERRED EMBODIMENTS

Figure 2:
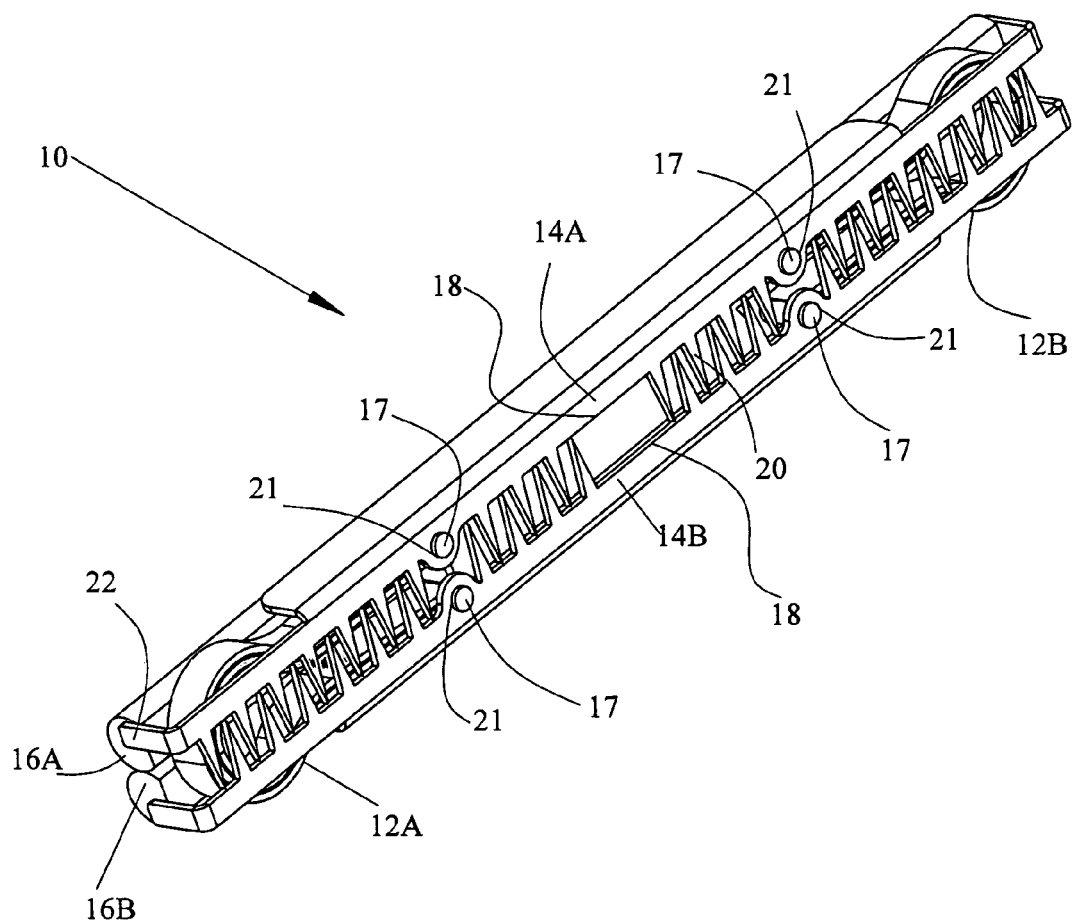
FIG. 2 shows an isometric view of the compression clip constructed according to a first embodiment in its closed position.

The present application should be read in conjunction with co-pending US application "Surgical Compression Clips", filed by the same applicant and inventors concurrently on Dec. 29, 2006. This document is herein incorporated by reference in its entirety.

The full transmural/thickness resections (FTR) contemplated by the present invention makes use of surgical compression clips, typically non-unitary compression clips, instead of conventional staples. Such clips substantially lessen the likelihood of internal leakage of bodily fluids which often occurs when staples are used. They also lessen the likelihood of bleeding and do not leave any permanent foreign body inside the body cavity.

The non-unitary, i.e. compound, surgical compression clip typically has one or more, often two, force applier elements, made of a shape-memory material, such as a nickel-titanium (Ni—Ti) alloy. The clip includes two compressing elements and two securing elements connected operationally by at least one of the shape-memory force applier elements. Typically, the compressing elements are linear as are the securing elements.

When closed on tissue, a constant compressive force acts between the two compressing elements and along their entire lengths. The compressing elements are connected at least one of their ends by the shape-memory force applier elements. The constant force which is independent of variation and tissue thickness typical of the particular organ being resected is a result of the well-documented long plateau region of the shape-memory material's stress-strain hysteresis curve. This is a consequence of properties exhibited by shape-memory materials. Additionally, stress-induced strain is recoverable in these materials; in the case of Ni—Ti alloys, 6-8% of the strain can be recovered. The shape-memory alloys have the ability to reverse large deformations (plateau part of the stress-strain hysteresis curve of the material) which results in a large clip opening. The ability to generate a constant force within a wide range of deformations ensures that the clip is equally effective irrespective of the thickness of the compressed tissue. The clip, being sutureless, promotes hemostasis and a liquid tight seal which is required for aseptic healing.

Discussions on the stress strain curves and stress-induced strain of shape memory materials can be found in many publications. See for example "Shape Memory Materials", edited by K. Otsuka and C. M. Wayman, Cambridge University Press 1998, p. 62 and; H. Tobushi et al in "Deformation Behaviour of Ni—Ti Superelastic Alloy Subjected to Strain Variation" in SMST-94: The Proceeding of the International Conference on Shape Memory and Superelastic Technology, edited by A. Pelton, D. Hodson and T. Duerig, 1995, pp. 389-391.

It should also be noted that the line of compressive force produced by the compression elements of the clips of the present invention is not collinear with the line exerted by the securing elements on the tissue to be resected. These are two different lines of action, separated by a distance. Were they to be co-linear the healing of the tissue at the compression site may be compromised. Additionally the arrangement of non-collinearity allows for more homogeneous tissue compression by the compression elements. Any penetration of the teeth for securing the tissue is compensated for by the continuous compression line more proximate to the body cavity wall.

The present invention provides an endoscopic resection system and elements thereof for use in full transmural/thickness resections (FTR). The endoscope body is positioned in the primary lumen of a multi-lumen sleeve. The secondary lumens of the sleeve are typically collapsed and rest substantially adjacent to the primary lumen while the endoscope body is advanced through the gastrointestinal (GI) tract. After the endoscope is positioned adjacent to a lesion in the gastrointestinal tract, the one or more secondary lumens are expanded by introducing and advancing the required working instruments to the distal end of the lumen(s).

A compression clip attached to an applier is brought to the lesion through one of the secondary lumens of the sleeve while the clip and its associated applier are in their closed positions. The applier and compression clip then exit the open distal end of the secondary lumen near the suspect lesion and the clip is opened by the applier.

A grasper assembly is advanced and positioned near the suspect lesion. The assembly may be advanced through another secondary lumen of the multi-lumen sleeve, or alternatively through the same secondary lumen in which the clip and its applier are advanced, or alternatively through a working channel of the endoscope. While advancing the grasper assembly in a direction from the proximal to the distal end of the endoscope, the grasper and its forceps arms are held inside a small profile grasper transporting element. After the grasper transporting element exits the secondary lumen or working channel at its distal end, the grasper exits the grasper transporting element from an open window in its side and the forceps arms of the grasper open.

The grasper then is brought to the lesion through the open clip, grasping the lesion, pulling it, and extending it further by rotating it over, and wrapping it around, the grasper transporting element. Rotation is effected by rotating the entire grasper assembly, i.e. the grasper, the grasper transporting element, and the cable or shaft. The latter is in mechanical communication with an actuator at the proximal end of the endoscope shaft. This rotation step allows for a sufficient amount of tissue to be brought to and through the open surgical clip and to be positioned for a full transmural/thickness resection. It also allows for sufficient tissue around the base of the lesion, i.e. the margin, to be resected, ensuring that no portion of a pre-cancerous or cancerous lesion escapes resection.

In order for the grasper to reach and grasp sufficient suspect tissue, parts of the grasper assembly typically, but without intending to be limiting, have a bent configuration. Additionally, the bent portion of the assembly should typically possess sufficient elasticity to perform its function. Accordingly, parts of the grasper assembly may typically, but without intending to be limiting, be formed from a shape-memory material having the property of large reversible deformation.

A second type of grasper assembly that may be used is a vacuum-based grasper assembly. In this grasper assembly a flexible vacuum cup may be transported while in its closed position in a grasper transporting element to a lesion site. The vacuum cup is connected by one or more tubes to a suction producing source. The vacuum cup is brought adjacent to the lesion to be resected where it opens and uses suction to grasp the polyp and sufficient lateral margins. It then brings the tissue towards and through an open compression clip. Typically, the vacuum-based grasper assembly includes a means for articulation of the vacuum cup.

Once all the suspected tissue and tissue margins are brought through the open clip, i.e. past the clip's securing elements, the clip is closed. A severing device then severs the suspect tissue, and all tissue layers of the organ wall adjacent to it, while the clip compresses the resection site, producing tissue closure, necrosis and healing. As the compression clip closes over the pulled tissue, the teeth of the securing element ensure that the clip will not slip off the tissue during or after the resection.

The applier may be detached from the clip prior to resection. However, it is preferable that the applier be detached from the clip and withdrawn through the lumen or working channel through which it entered after resection. In such a case the applier acts to support the clip and resection site during resection. Similarly, after the clip is returned to its closed position and the suspect tissue is severed, the grasper or vacuum cup holding the severed tissue and the grasper transporting element are withdrawn together with the endoscope from the body.

In some embodiments of the vacuum-based grasper, the polyp or other suspect tissue may be withdrawn from the body cavity through the sleeve. Alternatively, the vacuum may be turned off, and the vacuum-based grasper assembly withdrawn outside the body while leaving the resected polyp in the lumen. The polyp can then be retrieved using commercially available retraction devices or graspers to pull the resected polyp until it emerges from the body cavity.

The grasper assemblies and the clips and their appliers of the present invention may be used with standard commercially available endoscopes. Dedicated or specially designed endoscopes are not required.

It should be further noted that the instruments taught herein, including all the compression clips, can be used in resecting large pedunculated polyps as well as sessile polyps.

Additionally, the invention is not limited to any particular direction or shape of the resection incision; both radial and longitudinal incisions are contemplated by the present invention.

The shape-memory force applier elements contemplated in the present invention are typically made of Ni—Ti alloys but other shape memory materials may also be used. The other elements of the clip, i.e. the compressing elements and the securing elements (and possibly separate toothed elements for attachment to the securing elements when there is no integrally formed toothed edge on the securing elements), may also be made of a shape-memory material such as a Ni—Ti alloy, but that is not essential. Other metals or alloys, such as stainless steel or other titanium alloys, and even certain plastic materials may also be used.

The system and method described herein have certain advantages which inter alia include:

- The sleeve being thin and flexible does not compromise the physician's ability to insert and maneuver the endoscope in place;
- The system can be adapted to work with commercially available endoscopes. Dedicated endoscopes may be considered but are not a requirement.
- The instruments can be advanced only after the endoscope is in place, once again not hindering positioning of the endoscope;
- Closure is dependent on continuously compressing the tissue at the resected site and is indifferent to the variation of tissue thickness typical of a specific organ;
- The system may allow for complete full thickness resection in a single procedure rather than the more typical piecemeal procedures currently being in use;
- No foreign bodies are left behind in the body cavity after healing of the resected site is completed;
- The method of the present invention allows for retrieval of a complete sample for pathology, a sample including adequate tissue margins and all the tissue layers of the adjacent organ wall; and
- Since the compression clip employed makes use of shape memory materials, the clip may be of relatively small dimensions and there is no need for large instruments, such as currently employed stapler firing mechanisms. This permits easier advance of the instrument to the lesion site.

Before explaining embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIGS. 1A-1C, to which reference is now made, show an overall view of an endoscopic system constructed according to the present invention, an enlarged view of the system's distal end F and an enlarged view of the system's proximal end N, respectively.

FIG. 1A includes an endoscope insertion shaft 300 encased in a multi-lumen sleeve 150. At the distal end F of endoscope insertion shaft 300, working instruments constructed according to the present invention may exit. These instruments include a surgical clip 10 attached to an applier 30 and a grasper assembly 200 including a grasper transporting element 260. These instruments are inserted into a working channel 154 of endoscope insertion shaft 300 or one or more secondary lumens 158 of sleeve 150. Insertion of the instruments is effected at the proximal end N of endoscope insertion shaft 300. They are advanced in the direction of, and ultimately exit at, or adjacent to, the distal end F of endoscope insertion shaft 300. Actuators 306 and 308 may be any of many known to those skilled in the art. They can apply one or a combination of control actions or movements, such as pull and release, articulation, swivel and the like. Endoscope insertion shaft 300 is typically connected to a fiberoptic cable 304 which communicates images to a visual display 302.

Details of the instruments used, the multi-lumen sleeve and other specific aspects of the system of the present invention are further discussed below.

Figure 3A:
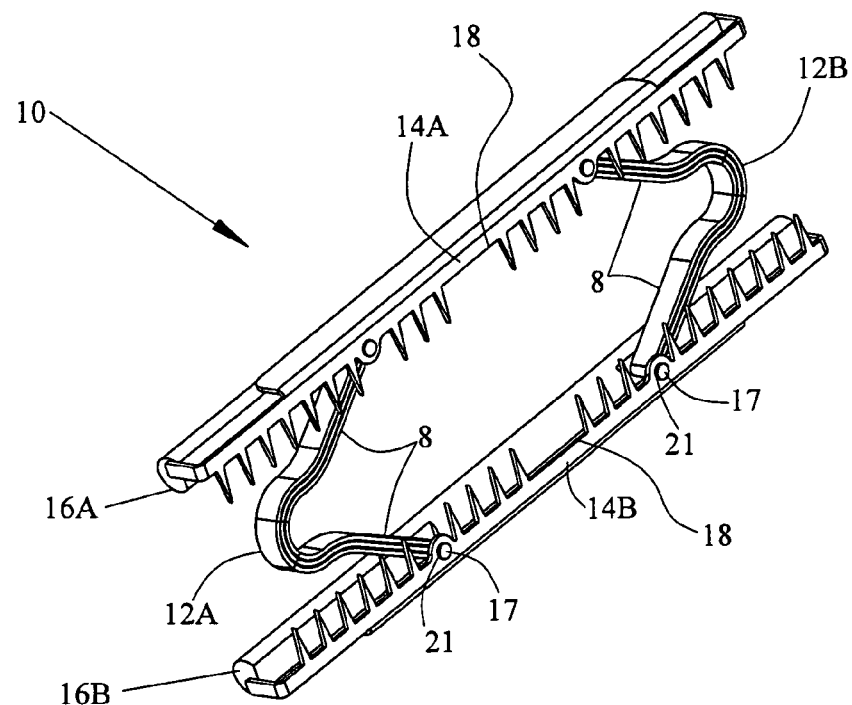
FIGS. 3A and 3B show isometric top and bottom views of the compression clip shown in FIG. 2 in its open position.
Figure 3B:
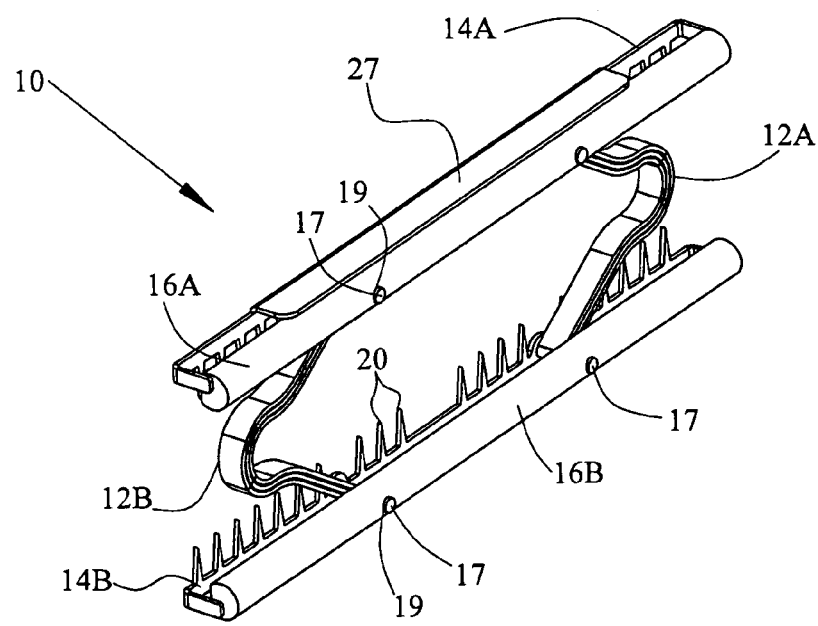

Reference is now made to FIGS. 2-3B where FIG. 2 presents a view of a non-unitary compression clip constructed according to a first embodiment of the present invention. In FIG. 2 the clip is shown in its closed position. FIGS. 3A and 3B present a view of the compression clip shown in FIG. 2 in its open position.

Clip 10 is constructed of two shape-memory hinge springs 12A and 12B; also herein often denoted as force appliers. Typically, but without intending to be limiting, the shape-memory material is a Ni—Ti alloy. The operation of the clip relies on shape-memory effects exhibited by these materials. Springs 12A and 12B may be made of a single wire or flattened wire or strip or it may be constructed of two or more wires, flattened wires or strips connected together at their ends. Furthermore, in some embodiments, the springs may be constructed to have a coiled shape.

Clip 10 further includes two securing elements 14A and 14B, each of which has a series of teeth 20 for grasping tissue. Each of securing elements 14A and 14B may be formed from a single piece or welded together from several pieces, typically but without intending to be limiting, of metal. Teeth 20 may be formed integrally with elements 14A and 14B or they may be joined to the elements, for example, by welding. Generally, these securing elements are made of metal and typically are welded or otherwise joined to two metal compressing elements 16A and 16B. However, the securing elements and the compressing elements may be joined together by any method known to those skilled in the art. Securing elements 14A and 14B may also be formed integrally with compressing elements 16A and 16B, respectively.

Securing elements 14A and 14B are formed with spacings 18 configured and sized to receive the pushing elements of a clip applier (not shown). Compressing elements 16A and 16B, typically, but without intending to be limiting, are cylindrically-shaped. These include holes 19 (best seen in FIG. 3B) into which connectors 17 (also best seen in FIG. 3B) of hinge springs 12A and 12B are insertable. Insertion of hinge springs 12A and 12B occurs prior to welding or otherwise joining toothed securing elements 14A and 14B to compressing elements 16A and 16B, respectively. As a result of the weld or other joining method, securing elements 14A and 14B prevent connectors 17 of hinge springs 12A and 12B from dropping out of holes 19. Securing elements 14A and 14B, and compressing elements 16A and 16B are joined together by hinge springs using any method known to those skilled in the art, particularly in the art of articulation hinges (swing joints). The natural tension of hinge springs 12A and 12B operates to keep compressing elements 16A and 16B in their closed position as in FIG. 2.

The metal used for forming securing elements 14A and 14B, compressing elements 16A and 16B and teeth 20, if these latter are made from separate pieces and welded to elements 14A and 14B, should be a rigid metal such as, but without being limiting, stainless steel.

While in the above embodiment, securing elements 14A and 14B are welded to compressing elements 16A and 16B, respectively, in other embodiments this need not be the case. The securing and compressing elements may be joined to each other by mechanical means such as by U-shaped elements positioned on securing elements 14A and 14B clippably engageable to compressing elements 16A and 16B or by press connections wherein an edge on each of securing elements 14A and 14B would be pressed to enter a slit in their respective compressing elements 16A and 16B. Alternatively, securing elements 14A and 14B and compressing elements 16A and 16B can be crimped together.

In other embodiments, securing elements 14A and 14B and compressing elements 16A and 16B may be made of a single piece of plastic, for example by ejection molding. In such embodiments, only hinge springs 12A and 12B are made of metal, specifically a shape-memory metal or alloy, typically but without intending to be limiting, a Ni—Ti alloy. In such plastic embodiments, hinge springs 12A and 12B (force appliers) would typically be snapped into place between securing elements 14A and 14B and compressing elements 16A and 16B. However, it is evident to one skilled in the art that other methods of introducing the metal hinge springs 12A and 12B could also be used.

Clip 10 in its closed position appears as shown in FIG. 2. Hinge springs 12A and 12B exert no force when the clip is fully closed, i.e. when compressing elements 16A and 16B lie proximate and tangent to each other. However, as compressing elements 16A and 16B are separated apart, hinge springs 12A and 12B exert a force which tries to bring compressing elements 16A and 16B and securing elements 14A and 14B together. When clip 10 is to be opened, pushing elements of a clip applier (not shown) may be positioned and wedged between teeth 20 of securing elements 14A and 14B or they may be positioned in a spacing or indentation 18. The applier is activated to apply a force via its pushing elements (not shown). This force opposes the force exerted by binge springs 12A and 12B. This counter force spreads securing elements 14A and 14B and compressing elements 16A and 16B apart. It also spreads hinge springs 12A and 12B as in FIGS. 3A and 3B.

After tissue is brought to and positioned between the separated compressing elements 16A and 16B, the applier is operated to relax the applied force allowing securing elements 14A and 4B to move toward each other and to return to their original closed position (FIG. 2). Shape-memory hinge springs 12A and 12B also relax and return to their original shape. The tissue positioned between the securing and compressing elements of clip 10 prevents compressing elements 16A and 16B and springs 12A and 12B from completely returning to their original-closed positions. Once the compressing elements are stopped by the tissue, continued closure of the applier's pushing elements leads to separation of the pushing elements of the applier from securing elements 14A and 14B of clip 10. This, in turn, causes the applier to disengage from clip 10.

While the shape-memory elements used to effect opening or closing of clip 10 are here described as hinge springs, these elements can more generally be classified as force appliers. Therefore, it should be understood that elements of any shape which can generate a force for either opening or closing a compression clip may be used and these elements can and will often be denoted herein as force appliers.

In other embodiments, pushing elements of a clip applier are inserted into special indentations in securing elements 14A and 14B. The spacing/indentation is best seen as element 718 in FIGS. 25A and 26A discussed below. In yet another embodiment, when pushing securing elements 14A and 14B, the pushing elements of an applier (not shown) are inserted and loosely held in holes (not shown) positioned on securing elements 14A and 14B. It should be obvious to those skilled in the art that the pushing/attachment elements of a clip applier can be received in apertures positioned anywhere in the clip assembly including, but not limited to the securing elements and the compressing elements.

Figure 4A:
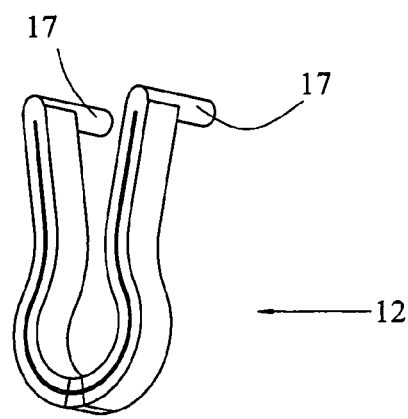
FIGS. 4A, 4B and 4C show isometric views of different configurations of spring elements constructed according to various embodiments of the present invention.
Figure 4B:
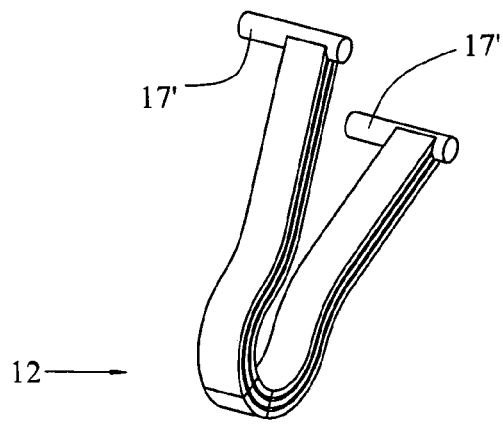
Figure 4C:
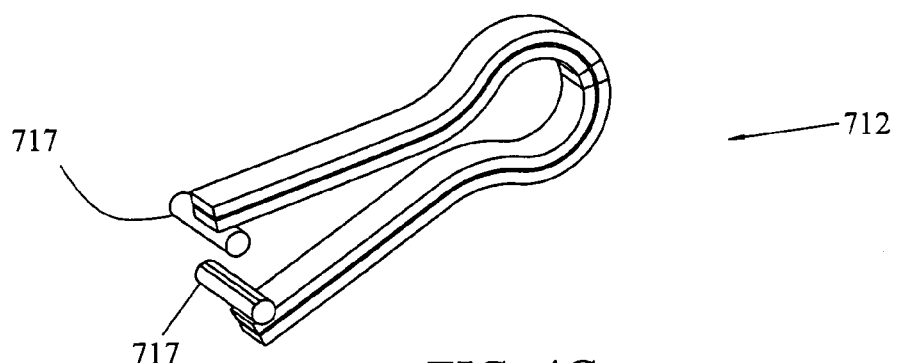

Shape-memory hinge springs 12A and 12B can have distinctive connectors 17 at their ends as shown in FIGS. 4A-4C. A hinge spring having uni-directional connectors 17 is shown in FIG. 4A. However, the use of hinge springs with bi-directional connectors 17' as shown in FIG. 4B is advantageous over the uni-directional connectors 17 shown in FIG. 4A. The hinge spring's bi-directionality allows connectors 17' to be inserted simultaneously into holes 21 in securing elements 14A and 14B and into holes 19 in compressing elements 16A and 16B. This increases stability of the clip 10. It also reduces the chance that hinge springs 12A and 12B will be displaced during operation of the clip and interfere with closure of the clip. The positioning of hinge springs 12A and 12B with connectors 17' can readily be seen in FIGS. 2, 3A and 3B where clip 10, in its closed and open positions, is shown. Reference to the use of hinge springs with connectors of the type of connector 717 shown in FIG. 4C will be made later in the text.

Connectors 17, 17' and 717 shown in FIGS. 4A, 4B and 4C respectively form articulating joints when they are inserted into corresponding apertures or holes in compression elements and/or securing elements as described in the first through fourth compression clip embodiments described below. These connectors rotate or swing in their respective apertures and holes allowing for articulation.

It should be noted that as in clip 10 of FIGS. 2-3B, in some embodiments teeth 20 do not necessarily extend the entire length of securing element 14A and 14B while in others they do.

Additionally, it should be noted that in some embodiments of clip 10 in FIGS. 2-3B, teeth 20 need not be distributed uniformly along securing elements 14A and 14B. Additionally, at both ends of elements 14A and 14B there is a small bend 22 welded or otherwise joined to the sides. In some embodiments, bend 22 may be integrally formed as part of elements 14A and 14B. This provides extra security against clip 10 slipping off the compressed suspect tissue during resection.

In the compression clip embodiments shown in FIGS. 2-3B and as discussed elsewhere in this specification, the securing elements and their respective compressing elements have been described as separate elements. In their operational state within the clips, these are typically a single joined element reflecting a single part and may be thought of as such. In the joined part, the securing elements attach to and grip the tissue to be resected while the compressing elements act to press the parts of the resected site together even when they are formed as separate elements and are only later joined together to operate as a single part.

Reference is now made to FIGS. 5-9 where various views of a first embodiment of a clip applier are shown. The clip applier may be used with surgical compression clip 10 shown in and described in conjunction with FIGS. 2-3B.

Figure 5:
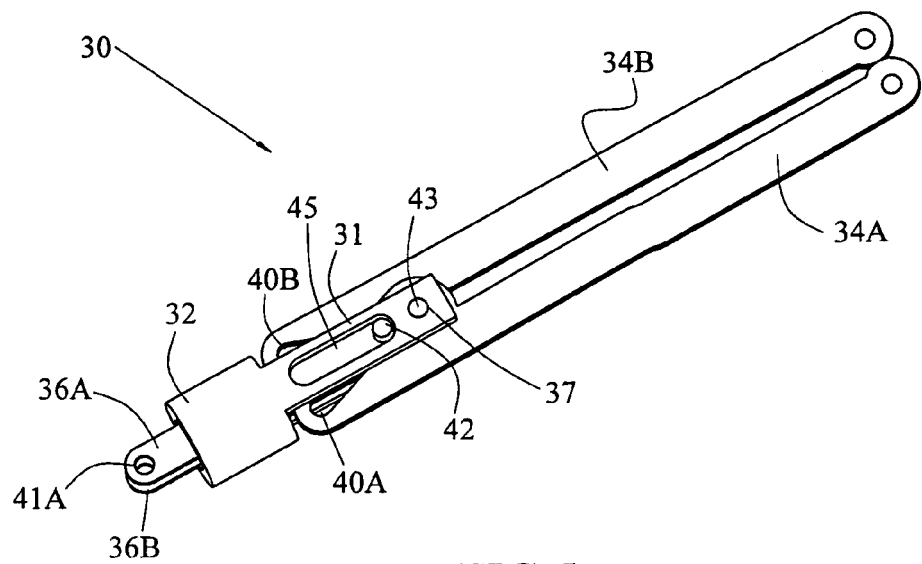
FIG. 5 is an isometric view of a clip applier constructed according to one embodiment of the present invention, the applier in its closed position.

FIG. 5 shows clip applier 30 in its closed position. Clip applier 30 is comprised of applier arms 34A and 34B, applier base 32, and connector elements 36A and 36B. The elements of clip applier 30 are typically constructed of stainless steel but they may also be constructed of other metals, such as, but not limited to, titanium, titanium alloys or reinforced plastics.

Figure 6:
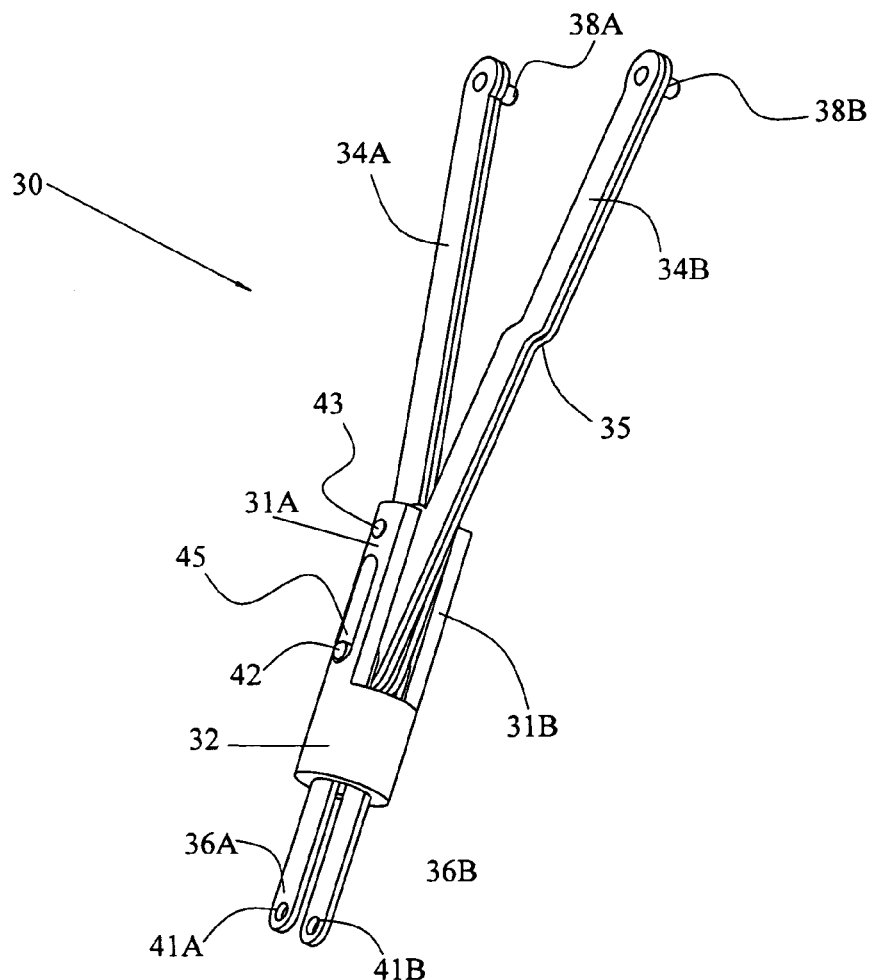
FIG. 6 is an isometric view of the clip applier in FIG. 5, the applier in its open position.

As best seen in FIG. 6 where clip applier 30 is shown in it open position, each of applier arms 34A and 34B has, at its distal end, an insertion projection 38A and 38B, respectively. Insertion projections 38A and 38B are formed substantially transverse to applier arms 34A and 34B and are operative for insertion between teeth 20 of securing elements 14A and 14B in FIG. 2, or into indentations 718 of clip 710 in FIG. 25A, or alternatively into holes positioned in securing elements 14A and 14B and compressing elements 16A and 16B.

Figure 7:
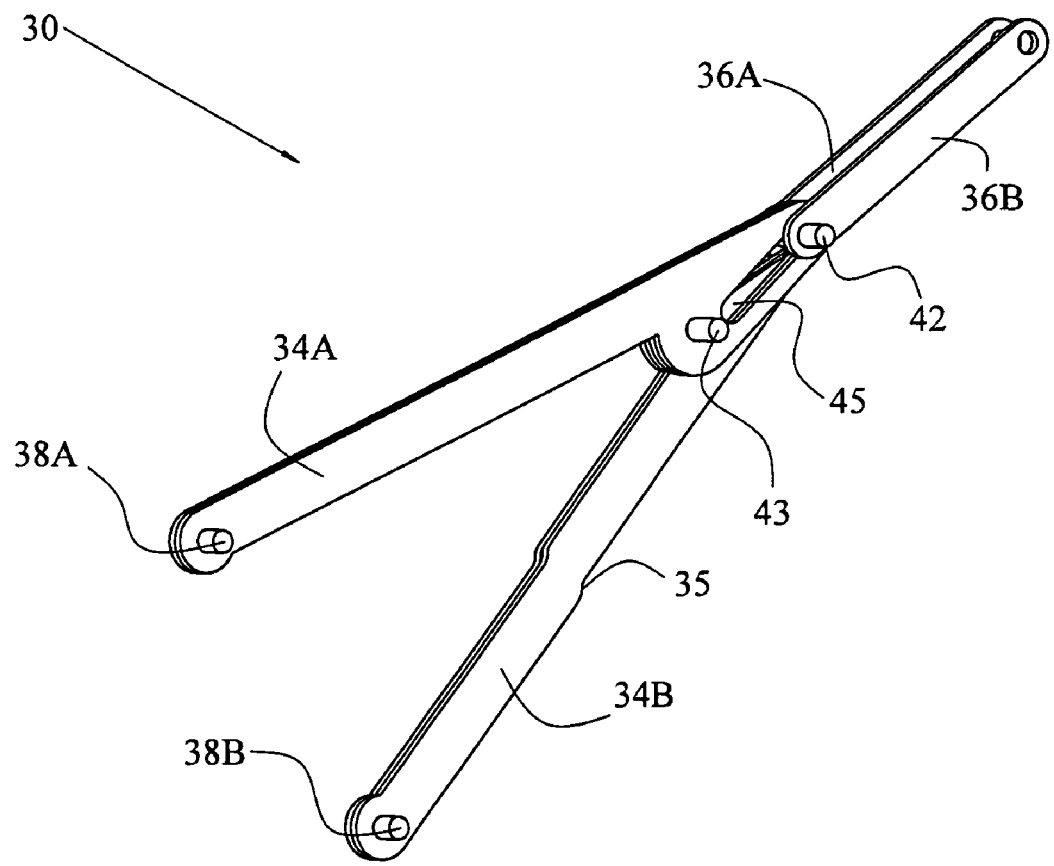
FIG. 7 is an isometric view of the clip applier in FIG. 5 without its base element, the applier in its open position.

FIG. 7 shows open clip applier 30 without its applier base 32.

As seen in FIGS. 5 and 6, applier base 32 has a generally barrel-like shape from which emerges a pair of applier base projections 31. Each of these projections 31 has an applier base slot 45 and an applier base projection hole 37. Each of applier arms 34A and 34B has at its proximal end applier arm slots 40A and 40B and applier arm holes (not shown). Applier arm 34B is constructed with a bend 35 in it so that the distal portions of arm 34B and arm 34A can lie in the same plane. It also allows insertion projections 38A and 38B to lie in the same plane.

Each of connector elements 36A and 36B has a pair of holes 41A-41D (41C and 41D not visible), one at each end of each element.

Applier arms 34A and 34B are joined to applier base 32 by connecting pin 43 which passes through applier base projection holes 37 and applier arm holes (not shown). Pin 42 is inserted into holes (not shown) in connector elements 36A and 36B and is movable in applier base slots 45 and applier arm slots 40A and 40B. As pin 42 moves it forces applier arm slots 40A and 40B to overlap with applier base slots 45 at the point of the pin, thus creating an opening and closing effect.

The proximal ends of connector elements 36B and 36A, respectively, are attached to an operating cable (not shown) that exits the proximate end of the endoscope. The cable is activated by an actuator 306 (FIG. 1A), for example, positioned outside the proximal end N (FIG. 1A) of the endoscope.

Figure 8:
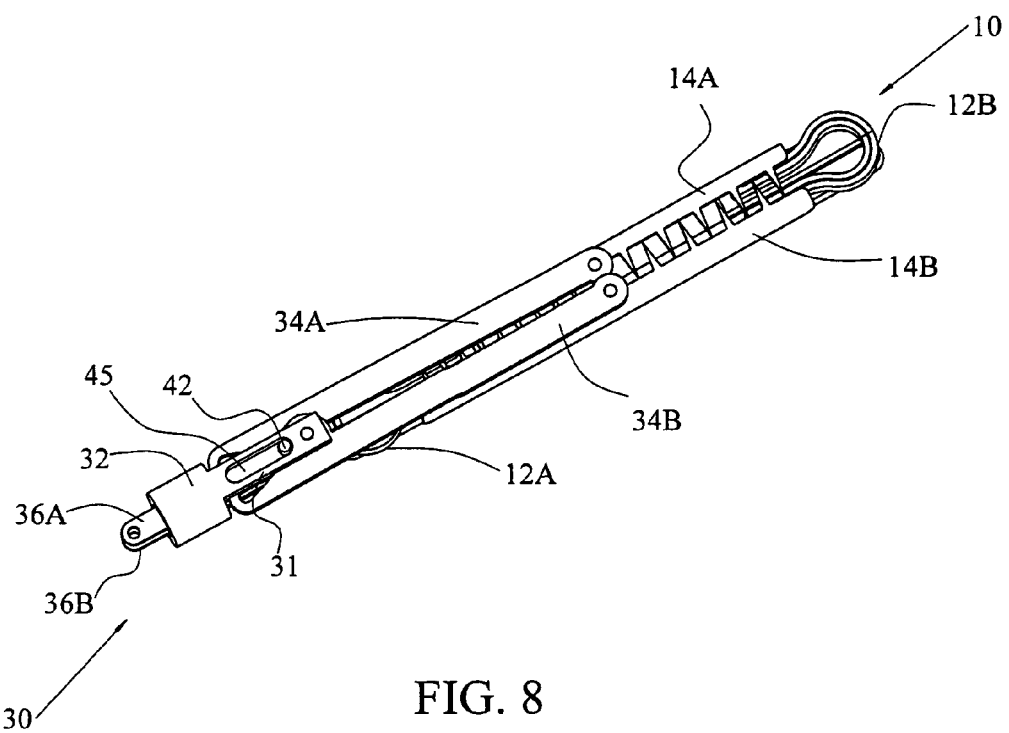
FIG. 8 is an isometric view of the clip applier of FIG. 5 used to position the clip in FIG. 2, the clip being attached to the applier and in its closed position.
Figure 9:
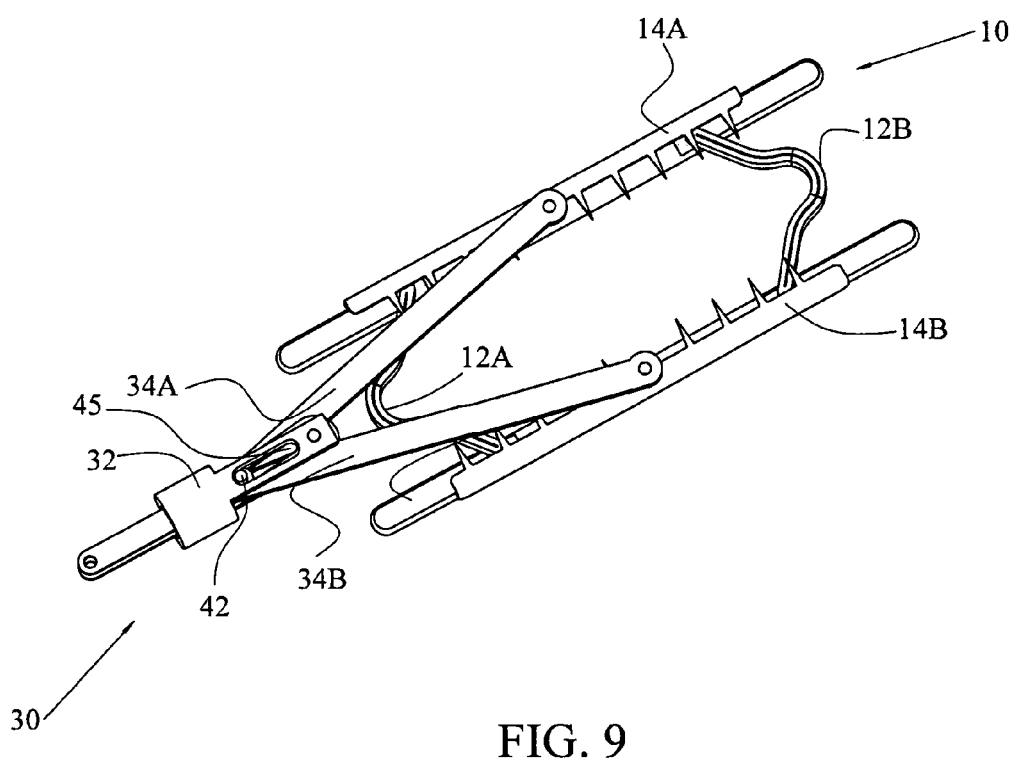
FIG. 9 is an isometric view of a clip applier used to position the clip in FIG. 2, the clip being attached to the applier and in its open position.

FIG. 8 and FIG. 9 show clip applier 30 of the present embodiment attached to surgical compression clip 10 described in FIGS. 2-3B in its closed and open position, respectively.

To open clip applier 30, an operating cable (not visible) pulls connector elements 36A and 36B in the proximal direction. Concurrently, pin 42 moves to the proximal end of applier base slots 45 and the proximal ends of applier arm slots 40A and 40B. In that position, applier arms 34A and 34B move apart as in FIG. 9.

To close clip applier 30, the tension in the operating cable (not visible) is released. In doing so, the force that hinge springs 12A and 12B exert is greater than that of the operating cable. A force is thus exerted on applier arms 34A and 34B through securing elements 14A and 14B. The clip's force brings applier arms 34A and 34B together, which pushes connector elements 36A and 36B in the distal direction. Concurrently, pin 42 moves to the distal end of applier base slots 45 and the distal ends of applier arm slots 40A and 40B. In that position, applier arms 34A and 34B move together as in FIG. 8.

Figure 26A:
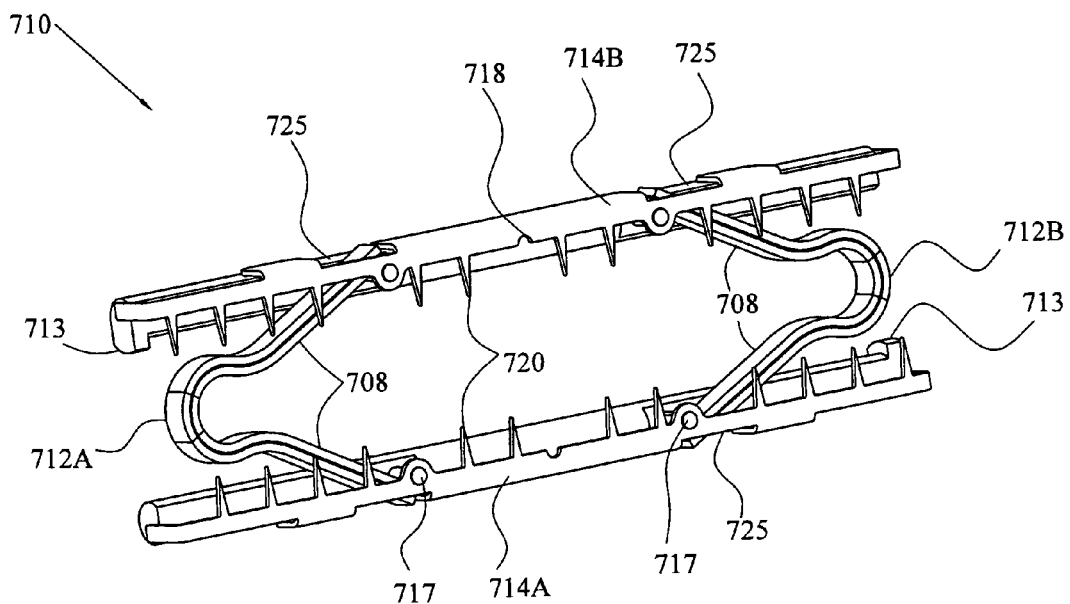
FIGS. 26A and 26B are an isometric top and bottom view of a clip constructed according to the embodiment of FIGS. 25A and 25B, the clip being in its open position.
Figure 26B:
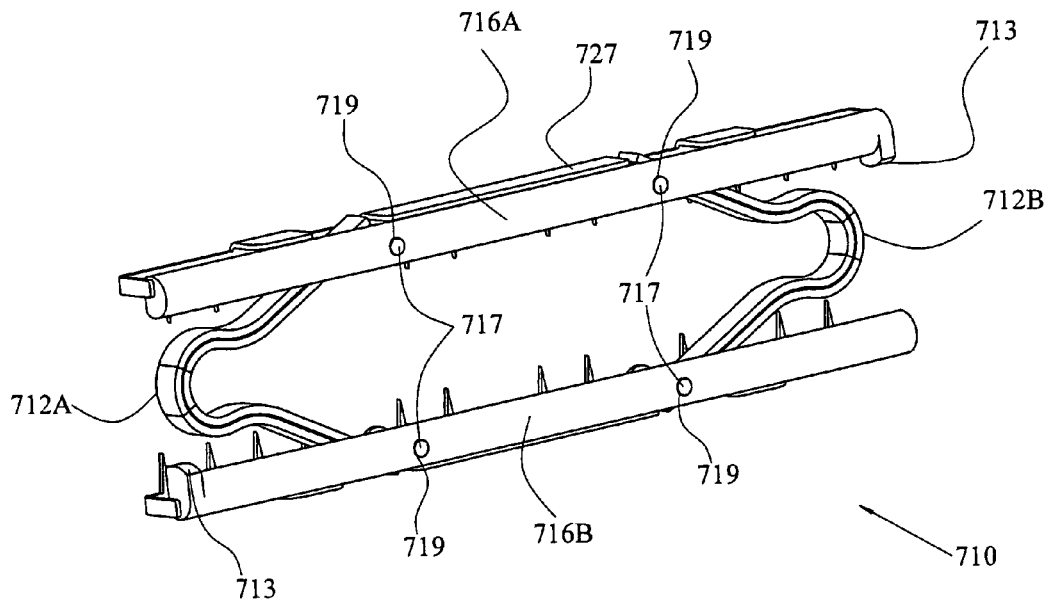

When applier arms 34A and 34B are pushed apart as in FIG. 9, insertion projections 38A and 38B of clip applier 30 push against the spacings between teeth 20 of securing elements 14A and 14B of clip 10 shown in FIG. 2 (or indentations 718 of clip 710 shown in and discussed below in conjunction with FIGS. 26A and 26B) so that securing elements 14A and 14B and compressing elements 16A and 16B of clip 10 move apart. When applier arms 34A and 34B are moved together as in FIG. 8, insertion projections 38A and 38B of clip applier 30 exert a reduced force on the spacings between the teeth 20 of securing elements 14A and 14B of clip 10 in FIG. 2 (or on indentions 718 of clip 710 shown in and discussed in conjunction with FIGS. 26A and 26B) so that securing elements 14A and 14B and compressing elements 16A and 16B of clip 10 move together. The counter force exerted by hinge springs 12A and 12B keeps clip applier 30 in place. Once tension generated by springs 12A and 12B is reduced sufficiently, that is as clip 10 closes on and compresses tissue, insertion projections 38A and 38B of applier 30 essentially fall away and disengage from clip 10.

Figure 10:
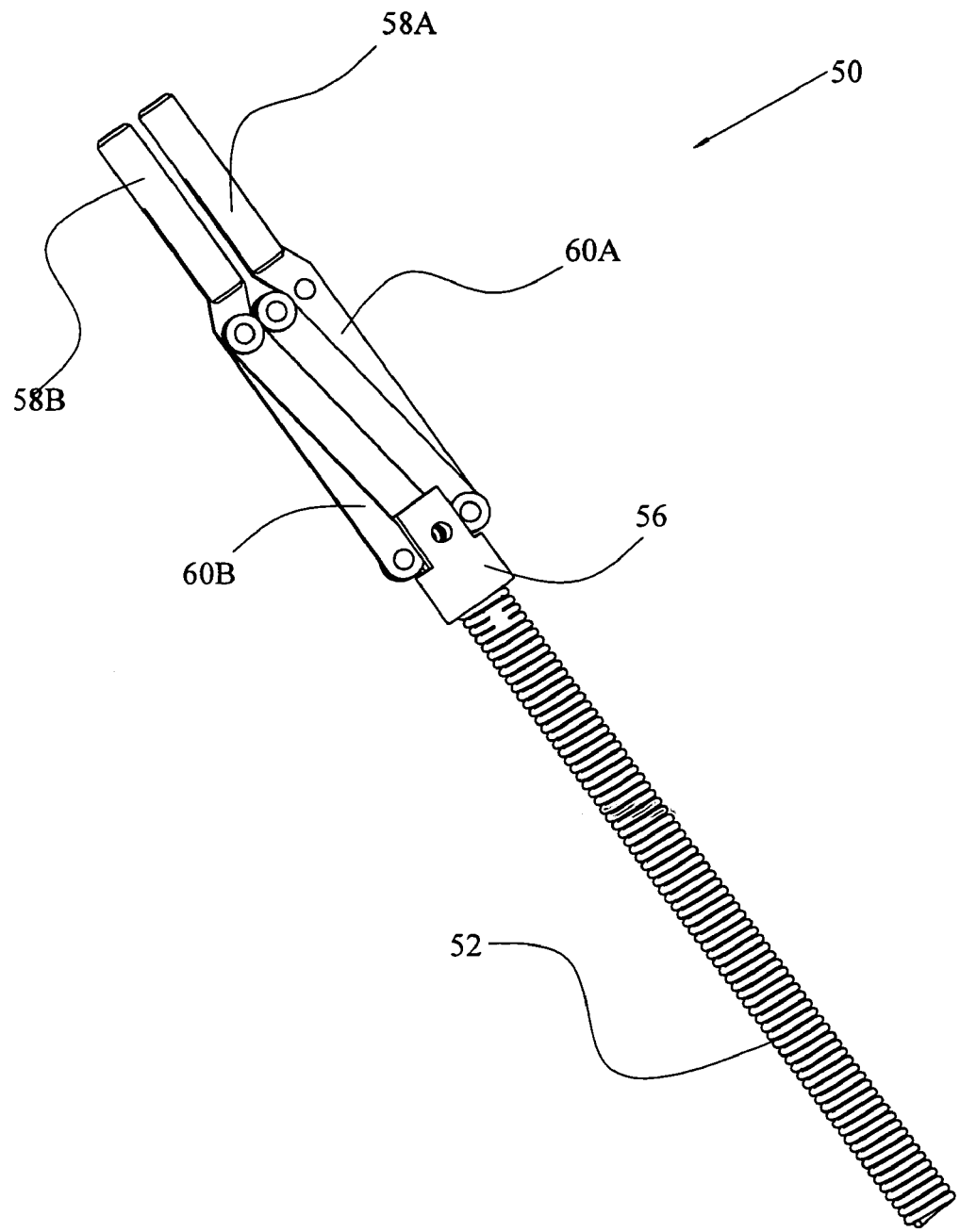
FIG. 10 is an isometric view of a clip applier constructed according to a second embodiment of the present invention, the applier in its closed position.
Figure 11:
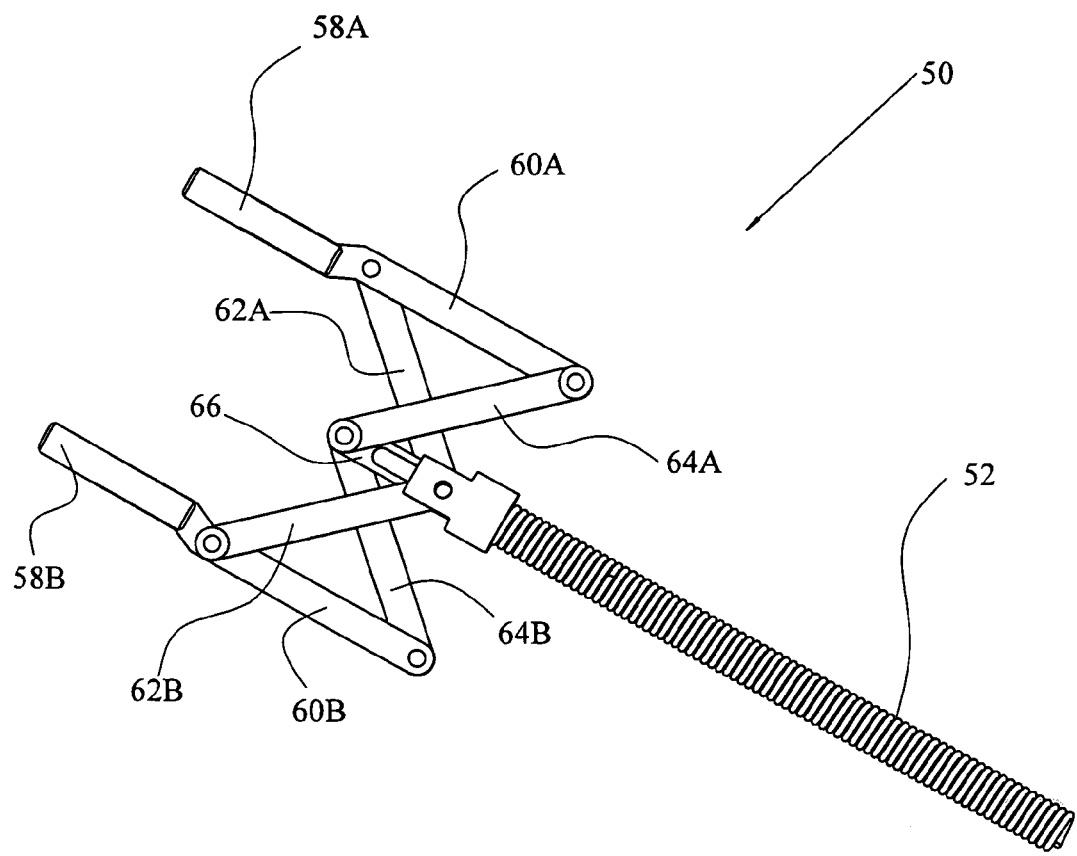
FIG. 11 is an isometric view of the clip applier in FIG. 10, the applier in its open position.

FIGS. 10-13, to which reference is now made, show various views of a second embodiment of a clip applier constructed according to the present invention. The applier is intended for use with the surgical compression clip (slightly modified as discussed below) shown in and discussed in conjunction with FIGS. 2-3B. FIG. 10 shows the clip applier in its closed position, while FIG. 11 shows the applier in its open position.

Turning to FIG. 11 first, clip applier 50 includes insertion links 60A and 60B which are swing jointed by links 62A, 62B, 64A, 64B and central bar 66. An operating cable (not shown) is connected to the proximal end of central bar 66 and inserted into spring 52. The latter connection can be achieved by welding or any other connecting method or means known to those skilled in the art.

Figure 12:
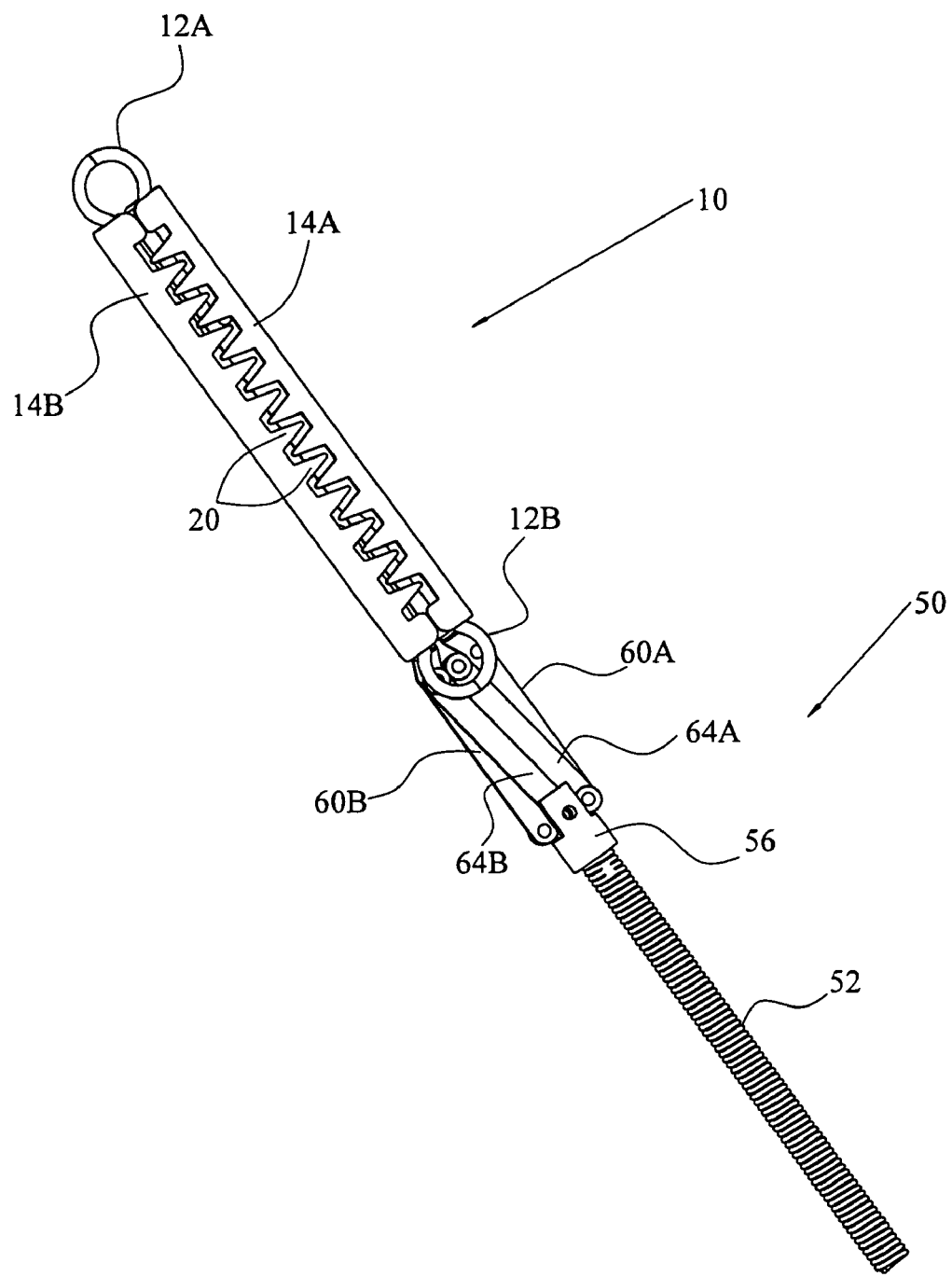
FIG. 12 is an isometric view of the clip applier of FIG. 10, attached to a clip constructed as in FIG. 2, the clip being attached to the applier and in its closed position.
Figure 13:
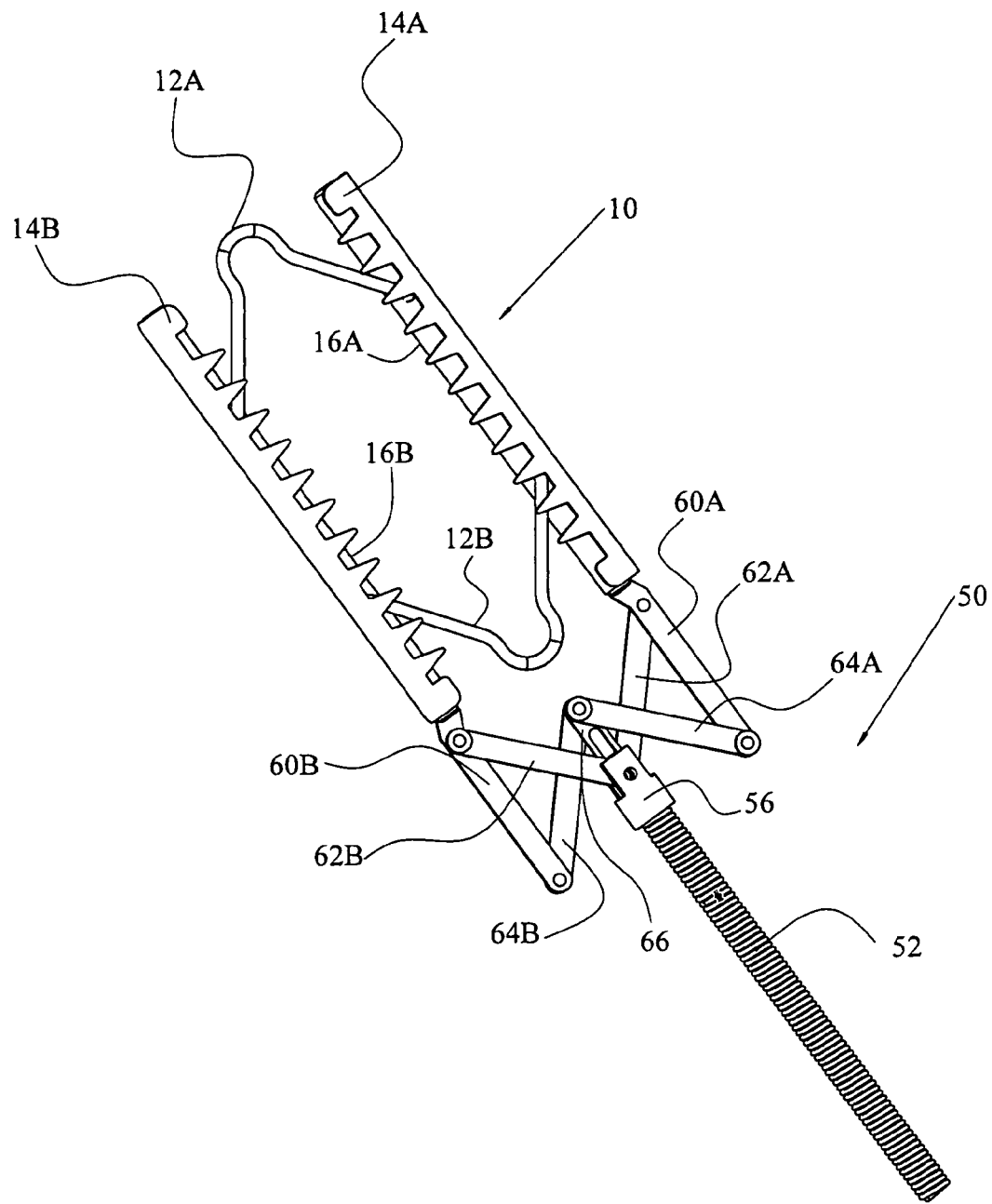
FIG. 13 is an isometric view of the clip applier of FIG. 10, attached to a clip constructed as in FIG. 2, the clip being attached to the applier and in its open position.

Insertion links 60A and 60B each have extensions (not shown) which are positioned on their distal end so that these extensions are insertable into cylindrical elements 58A and 58B. As shown in FIGS. 12 and 13, cylindrical elements 58A and 58B (best seen in FIGS. 10 and 11) are themselves insertable into the ends of compressing elements 16A and 16B of a surgical compression clip similar to clip 10 discussed above in conjunction with FIGS. 2-3B.

Compressing elements 16A and 16B, as shown in FIGS. 2-3B, require a slight modification to be compatible with cylindrical elements 58A and 58B of clip applier 50. To be compatible, at least one of the ends of elements 16A and 16B should be hollow and tubular so that cylindrical elements 58A and 58B of clip applier 50 can be inserted into them.

While in the embodiment shown in FIG. 10 and FIG. 11, cylindrical elements 58A and 58B are separate elements, in other embodiments they may be integrally formed at the ends of insertion links 60A and 60B.

FIGS. 10 and 11 show assembled clip applier 50 in its closed and open positions, respectively. FIGS. 12 and 13 show clip applier 50 inserted into compressing elements 16A and 16B of surgical compression clip 10 when the clip is in its closed and open positions, respectively.

Moving from the open to the closed position of clip applier 50 (or vice versa), and therefore to the open or closed position of clip 10 (or vice versa), can be effected using an operating cable (not shown) joined to, or in other ways in direct communication with, central bar 66 (FIG. 11). The cable passes through spring 52 and out of the proximal end N (FIG. 1A) of the endoscope where it is activated by a user employing an actuator (schematically shown as element 306 of FIG. 1A). The actuator may be any of several types known to those skilled in the art.

Spring 52, in addition to protecting the cable (not shown), serves as a stop sleeve for element 56 while pulling the cable thus enabling the separation of insertion links 60A and 60B. In addition, it allows for greater flexibility of the apparatus as it advances through a lumen of a multi-lumen sleeve (or an endoscopic working channel) from the proximal end of the endoscope toward the suspect lesion near the distal end of the endoscope. Alternatively, the cable can be covered and protected by a flexible tube. The tube may be formed of polytetrafluoroethylene (PTFE), but the choice of this material is exemplary only and it is not intended to be limiting.

To open clip applier 50, central bar 66 is pulled by the operating cable (not shown) in the proximal direction. When that occurs, interconnect links 62A and 62B and 64A and 64B and insertion links 60A and 60B move apart as in FIG. 11 due to the moment exerted on links 64A and 64B. When insertion links 60A and 60B are inserted into clip 10 as in FIG. 12, clip 10 also opens as shown in FIG. 13 because of the force exerted by insertion links 60A and 60B and their attached cylindrical elements 58A and 58B on compressing elements 16A and 16B.

During insertion of clip 10 into a body cavity, the clip is attached to clip applier 50 and both clip 10 and applier 50 are advanced, in their closed positions, through a secondary lumen of a multi-lumen sleeve (or through a working channel of the endoscope shaft). A tension is maintained in the operating cable (not shown) in order to keep clip 10 attached to clip applier 50 during the entire advance from the proximal end of the secondary lumen (or working channel) to its distal end. The tension in the cable or wire, acts against the force of hinge springs 12A and 12B of clip 10. This creates a force between cylindrical elements 58A and 58B of applier 50 and compressing elements 16A and 16B of clip 10 preventing detachment of clip 10 from applier 50. This force is smaller than the force required to open clip applier 50 and clip 10 attached to it.

To close clip applier 50, the tension in the wire/cable (not shown) passing through spring 52 is released. The force of hinge springs 12A and 12B is passed through compressing elements 16A and 16B to insertion links 60A and 60B. This force applies a moment on links 64A and 64B, which is opposite in direction to the moment exerted when pulling the wire/cable passing through spring 52. When that occurs interconnect links 62A and 62B and 64A and 64B and insertion links 60A and 60B move together as in FIG. 10. When they move together with clip 10 attached as in FIG. 12, compressing elements 16A and 16B also move together as shown in FIG. 12.

While completely releasing the tension in the pull wire allows for the applier to fully return to its original closed position, the tissue pulled and held within clip 10 prevents the clip from following the applier and fully returning to its original closed position. When this occurs, cylindrical elements 58A and 58B easily disengage from clip 10 since the hinge springs' 12A and 12B force is acting essentially on the tissue instead of on the applier.

Figure 14:
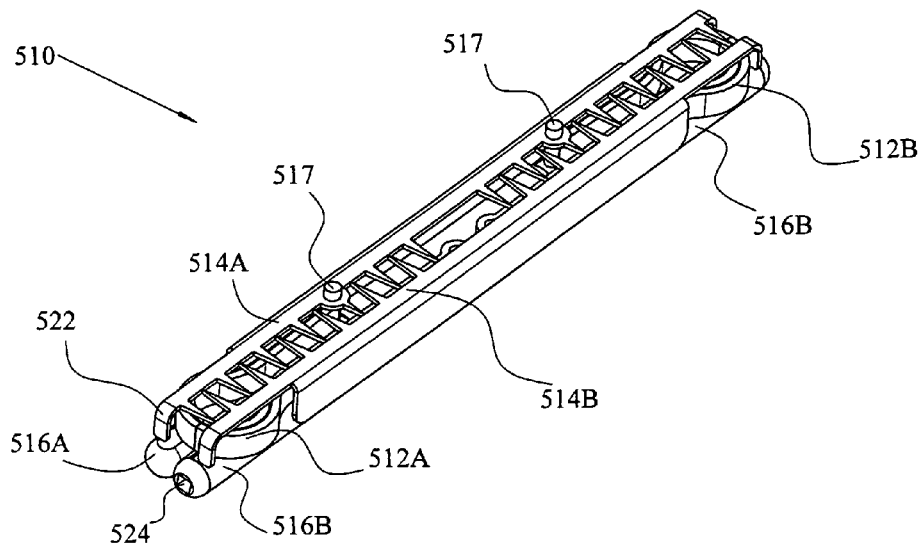
Figure 15:
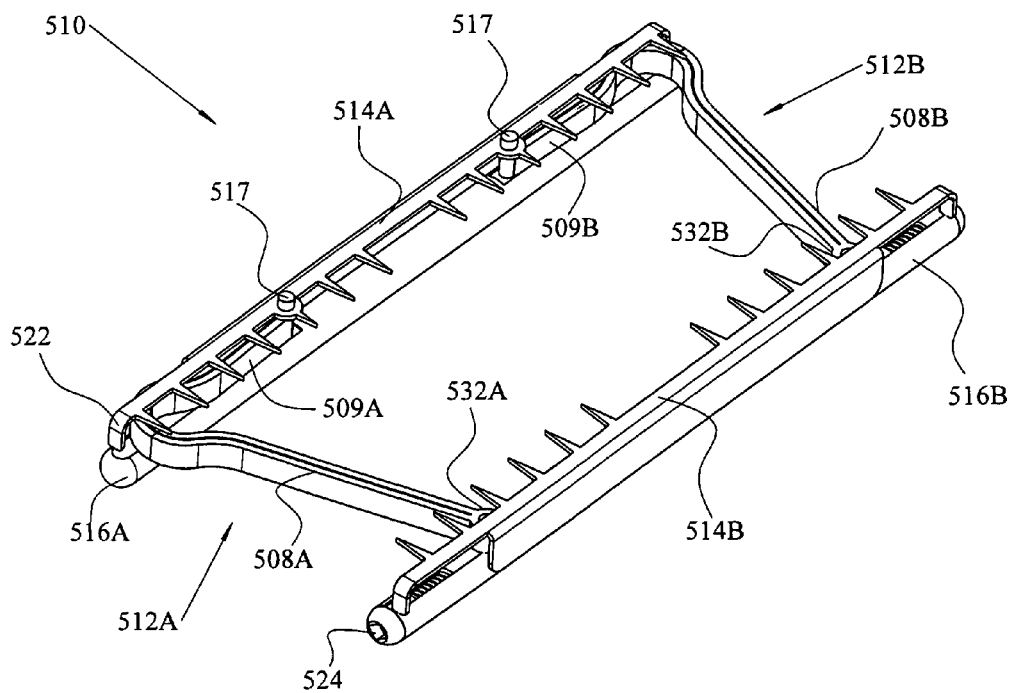
Figure 16:
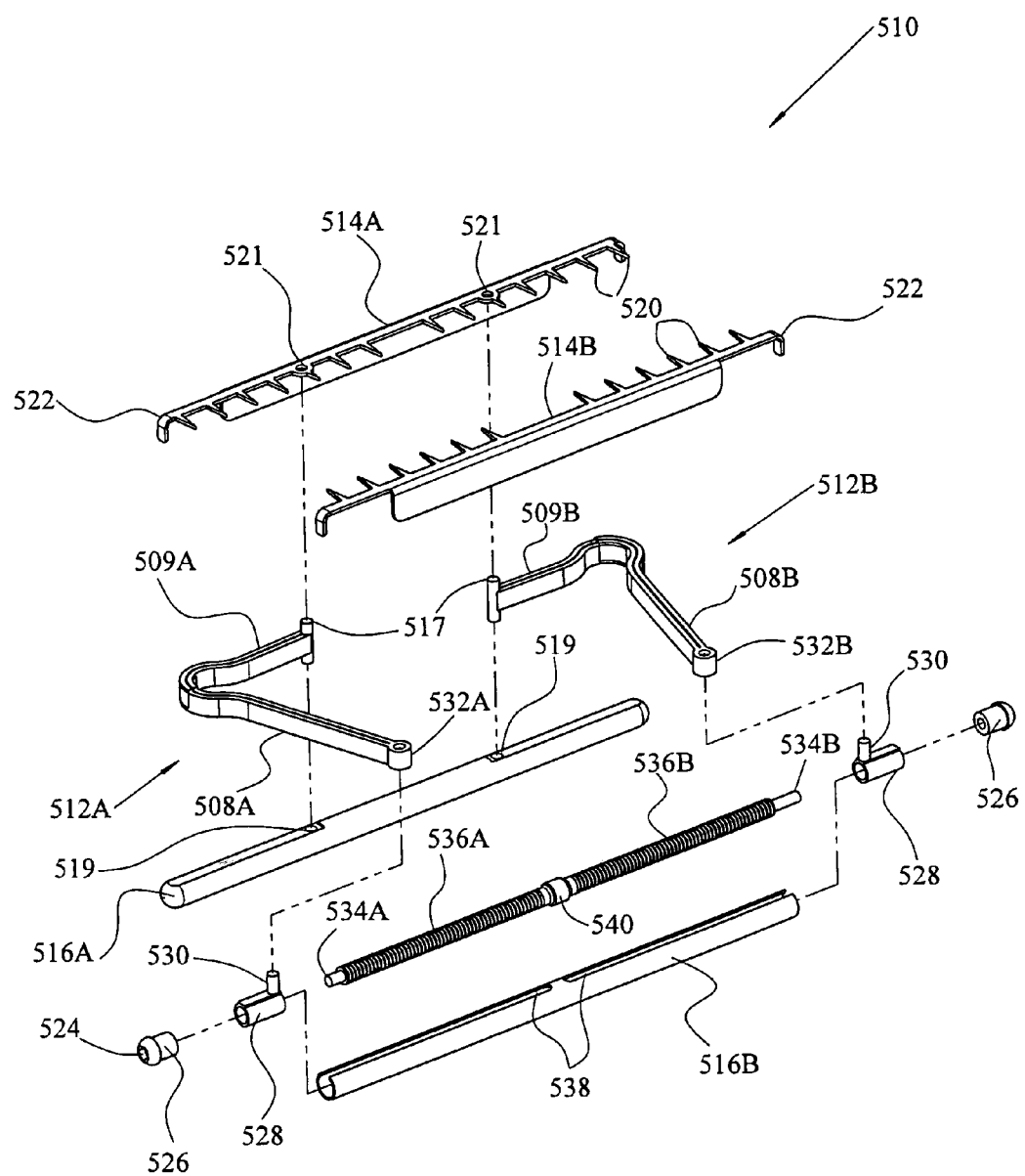
FIG. 16 shows an exploded view of the clip in FIGS. 14 and 15.
Figure 17:
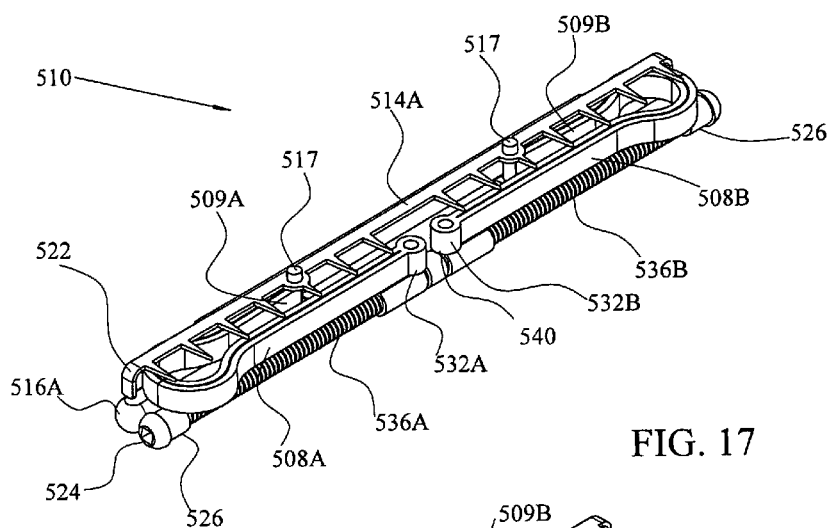
FIGS. 17 and 18 show isometric partially cut-away views of the compression clip shown in FIGS. 14 and 15, respectively.
Figure 18:
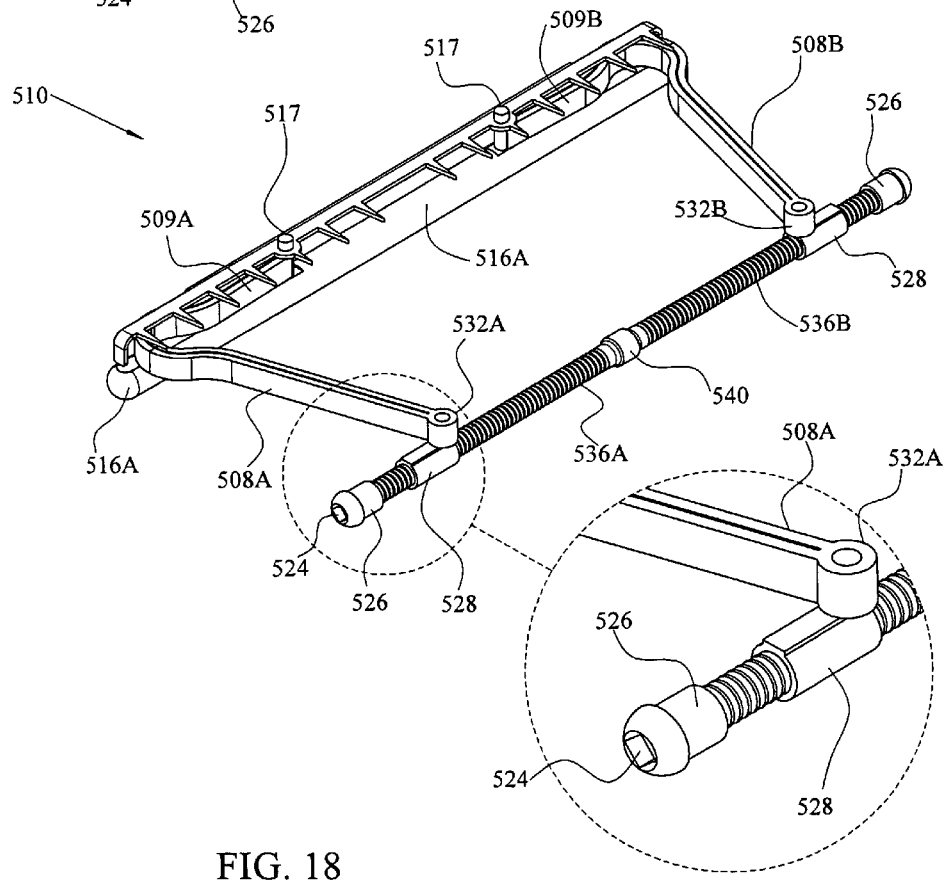

A second embodiment of a compression clip 510 constructed according to the present invention is shown in FIGS. 14-18, to which reference is now made. FIGS. 14 and 15 show clip 510 in its closed and open position, respectively. FIG. 16 is an exploded view of the clip and discussion of the clip will be made in conjunction with that Figure. Most of the elements in FIGS. 14-18 are the same as those discussed in conjunction with the clip embodiments shown in FIGS. 2-3B. Elements that are essentially equivalent in structure and operation will not be discussed again. Only new elements or structural features will be described. Essentially, identical or equivalent elements in the embodiments have been numbered as in clips 10 with the addition of 500 as a prefix.

In clip 510, hinge springs 512A and 512B are not symmetrical, each having legs which are of different lengths. Legs 508A and 508B are longer than legs 509A and 509B. Bi-directional connectors 517 are formed at the end of legs 509A and 509B. These connectors formed substantially transversally to the body of clip 510 are sized and configured to be inserted into holes 521 on securing element 514A and holes 519 on compressing element 516A. At the end of legs 508A and 508B are hollow cylinders 532A and 532B insertable over projections 530, more fully described below.

While compressing element 516A is configured essentially as in FIGS. 2-3B, compressing element 516B is a hollow tubular rod with two slots 538 on its surface proximal to securing element 514B. Inside compressing element 516B, a rod, formed of two connected threaded bolts 536A and 536B, is positioned. The length of each threaded bolt is less than half the length of the rod, with the bolts separated by connector means 540. Threaded bolts 536A and 536B each have different "handedness", that is thread direction. Because the two threaded bolts have different "handedness" they separate when turned in one direction and come closer together when turned in the opposite direction.

Over the ends of threaded bolts 536A and 536B are fitted cylindrical elements 528, the latter having complementary threads on their inner surface. Threaded bolts 536A and 536B have an attachment means 534A and 534B on their ends for insertion and joining with cylindrical elements 528. Cylindrical elements 528 are each formed with a projection 530 protruding substantially transversally to the long axis of cylindrical elements 528. Projections 530 pass through slots 538 preventing fitted cylindrical elements 528 from turning as threaded bolts 536A and 536B are turned. This forces cylinders 528 to move linearly along the long axis of compression element 516B. The threaded rod with cylinders 528 are held to compressing element 516B by plugs 526. Plug 526 on one side of the rod, the proximal side, includes a recess 524, typically, but without being limiting, a square recess, which is configured to receive a screw rotation apparatus (not shown). Projections 530 on cylindrical elements 528 are configured and sized to be inserted into hollow cylinders 532A and 532B formed on the longer legs 508A and 508B of springs 512A and 512B. The placement of legs 508A and 508B of hinge springs 512A and 512B and the relationship between plugs 526, cylindrical elements 528 and threaded bolts 536A and 536B (which when joined form the threaded rod discussed above) are best seen in FIGS. 17 and 18.

Figure 19:
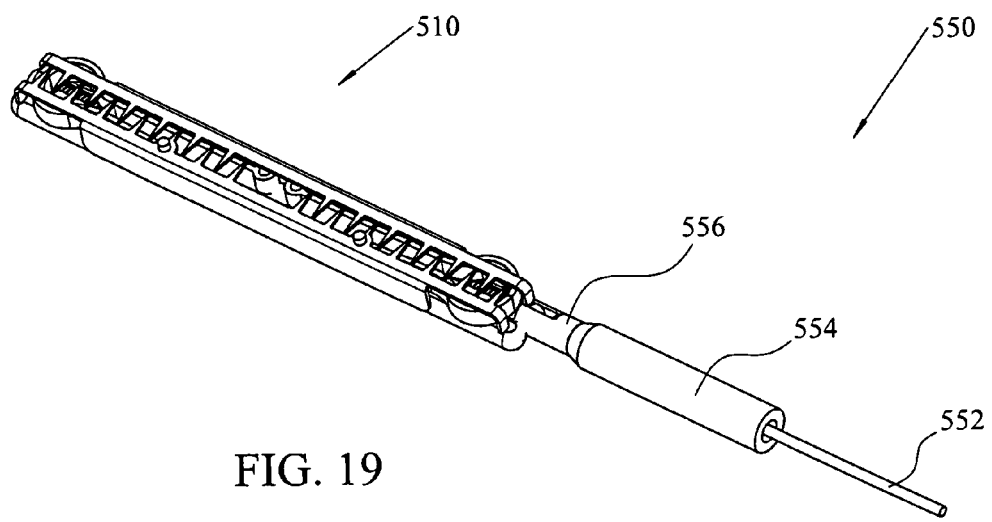
FIGS. 19 and 20 show isometric views of a clip applier used with the clip shown in FIGS. 14-18, FIG. 19 showing the applier engaged to the clip and FIG. 20 disengaged from the clip.
Figure 20:
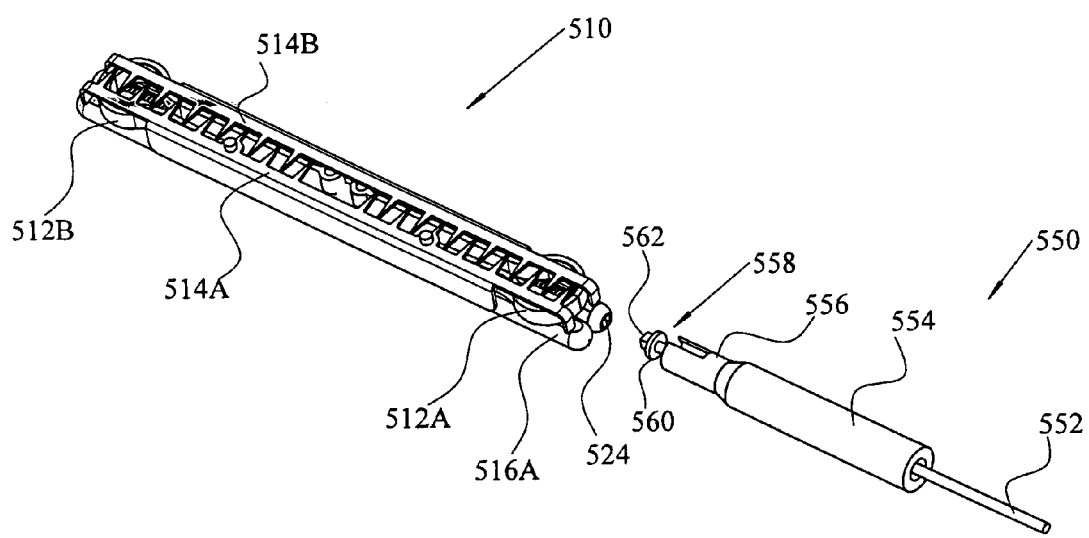

Reference is now made to FIGS. 19-23 which show a clip applier 550 that can be used to operate clip 510, the latter described in conjunction with FIGS. 14-18. FIGS. 19 and 20 show clip applier 550 in its engaged and disengaged position, respectively, with clip 510.

Figure 21:
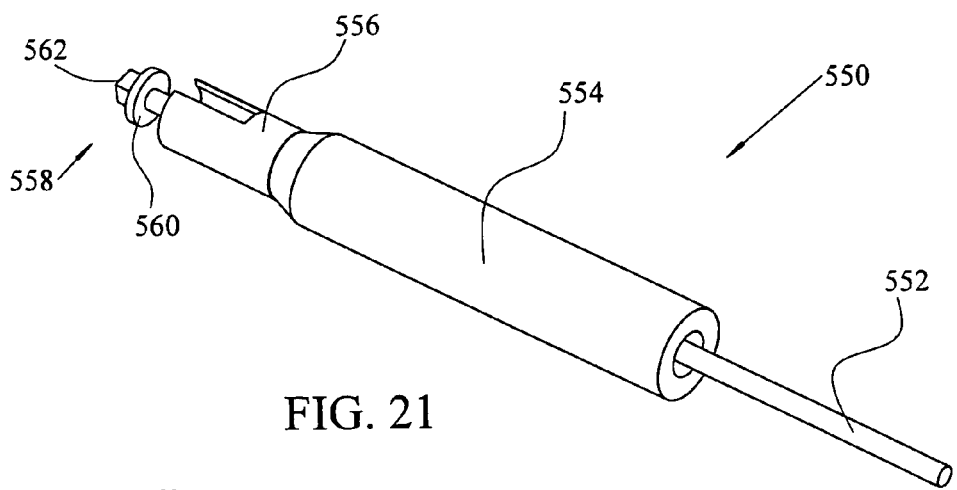
FIG. 21 shows an isometric view of the applier in FIGS. 19 and 20.
Figure 22:
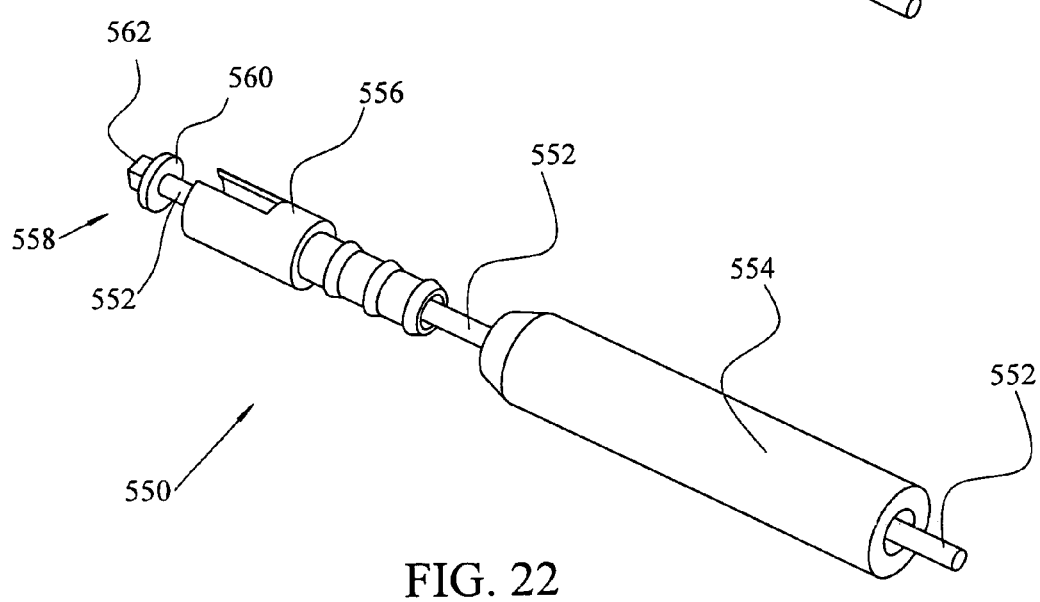
FIG. 22 shows a partially exploded view of the applier in FIGS. 19 and 20.
Figure 23:
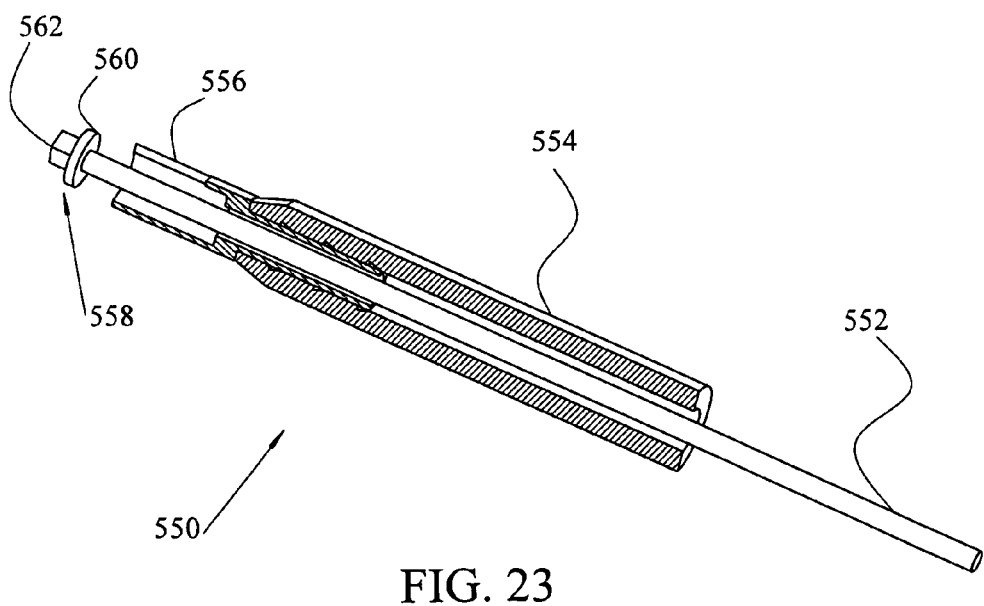
FIG. 23 shows a cross-sectional view of the applier shown in FIGS. 19 and 20.

The structure and operation of clip applier 550 can best be understood by viewing FIGS. 21-23. A cable 552 capable of being rotated is extended through a tube 554, typically a flexible plastic tube capable of advancing the clip to the distal end of an endoscope. Cable 552 ends at rotation head 558 which includes a washer element 560 and a male element 562, the latter sized and configured for insertion into recess 524 of clip 510 (FIGS. 14-18).

In some embodiments, tube 554 may be a spring having sufficient flexibility to advance a clip attached to applier 550 past the distal end of the endoscope.

Clip 510, for example, is inserted into a cup 556 of clip applier 550. Cup 556 typically is made of plastic or metal. Plug 526 with recess 524 (FIGS. 14-18) is positioned proximate to applier 550. Male element 562 is inserted into recess 524 of clip 510. Recess 524 and male element 562 are configured to be mateable. Moving clip 510 forward or backward is effected by pushing or pulling cable 552. Rotating cable 552 opens and closes the clip depending on the direction of rotation and the sequence of the bolts and the "handedness" of the threaded bolt proximate to male element 562.

Pushing forward releases clip 510 from applier 550. First, washer element 560 pushes clip 510 out of cup 556. Then, by pulling cable 552 towards the proximal end of the endoscope, male element 562 is released from recess 524 of clip 510, thereby fully releasing the clip from the applier.

Figure 24A:
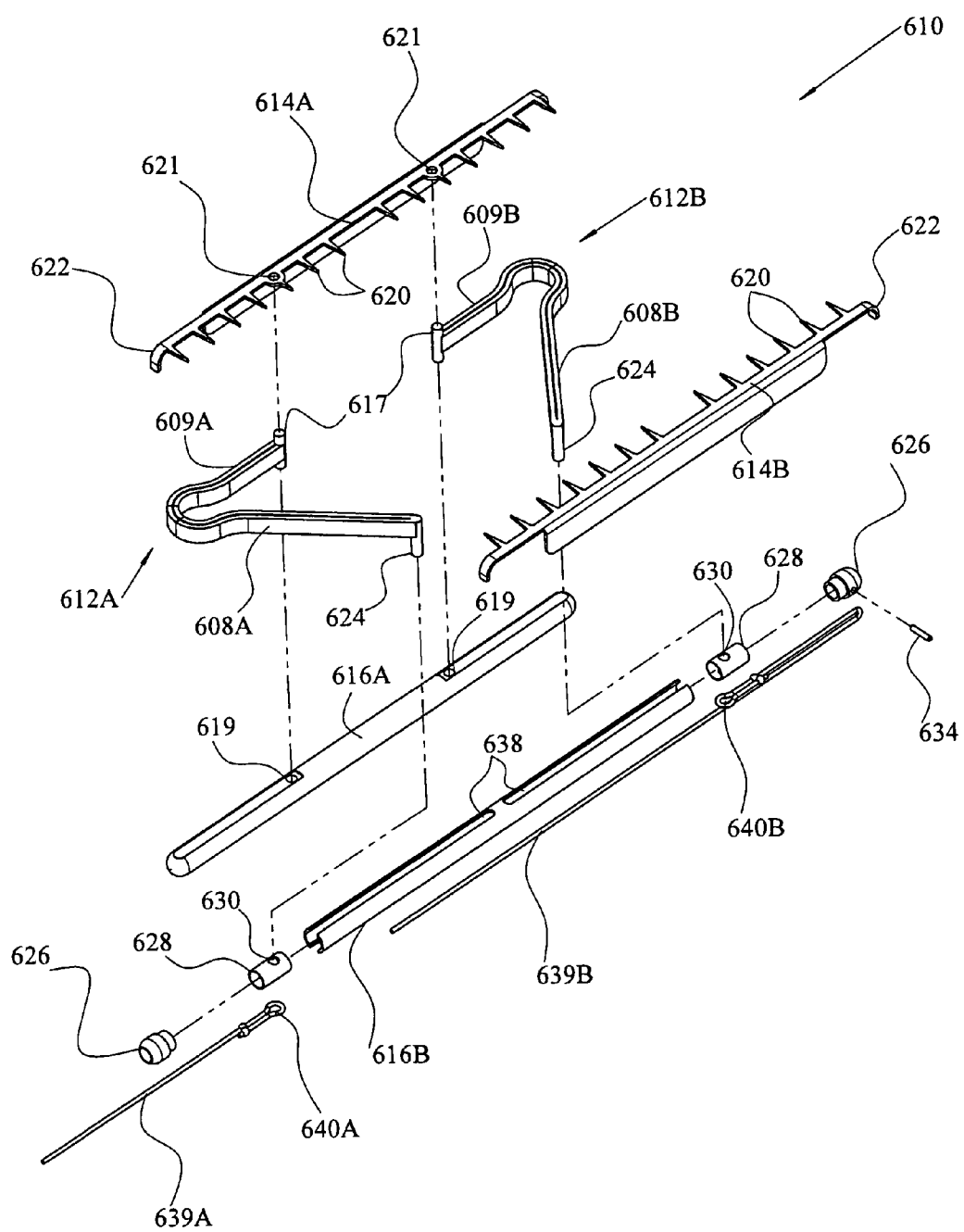
FIG. 24A shows an exploded view of a third embodiment of a compression clip constructed according to the present invention.
Figure 24B:
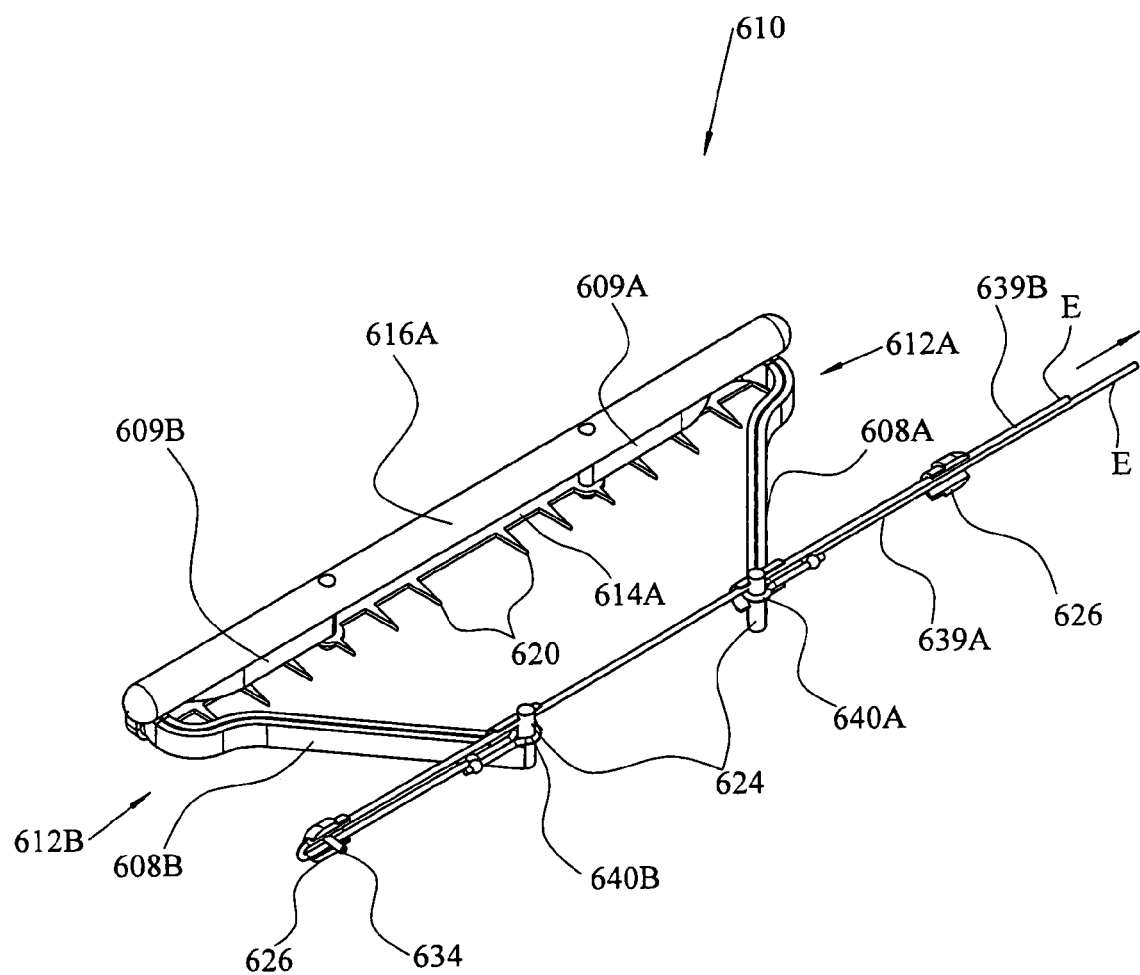
FIG. 24B shows an isometric partially cut-away view of the clip shown in FIG. 24A.

A third embodiment of a compression clip constructed according to the present invention is shown in FIGS. 24A and 24B, to which reference is now made.

From FIG. 24A, which shows an exploded view of clip 610, it is readily apparent that many of the elements presented there have been encountered and described previously in conjunction with previously discussed embodiments of compression clips constructed according to the present invention. Accordingly, elements that are structurally and operationally similar to previously described elements will not be described again here. Essentially identical or equivalent elements to those found in clips 10 and 510 have been numbered as in clips 10 and 510 with the prefix 600.

Securing and compressing elements 614A, 614B and 616A, 616B, respectively, are essentially the same as in clip 510. Hinge springs 612A and 612B are unsymmetrical as in clip 510. Again, there is a bi-directional connector 617 on the shorter legs 609A and 609B of hinge springs 612A and 612B which are inserted into holes 621 in securing element 614A and holes 619 on compressing element 616A. Compressing element 616B is again a hollow tubular member with two slots 638. The longer legs 608A and 608B of hinge springs 612A and 612B include unidirectional connectors 624 at their ends which extend in the direction of compressing element 616B allowing for insertion into preformed holes 630 of cylindrical elements 628, to be discussed below.

Cylindrical elements 628, formed with holes 630, are insertable into and retained in hollow tubular compressing element 616B. Holes 630 of cylindrical elements 628 act as receiving recesses for connectors 624 of springs 612A and 612B. When connectors 624 are inserted into holes 630 they are movable in slots 638 and do so with the opening and closing of springs 612A and 612B. Tubular compressing element 616B is capped by plugs 626. The plug 626 distal to the user has a hole into which pin 634 is inserted.

Passing through tubular compressing member 616B are wires 639A and 639B. These wires have loops 640A and 640B at their ends configured to fit over connectors 624.

Upon viewing FIG. 24B, the arrangement of the various elements of clip 610 and their operation becomes evident. In FIG. 24B, clip 610 has been flipped vis-a-vis the view shown in FIG. 24A and compressing element 616B and securing element 614B are not presented. By pulling the ends E of wires 639A and 639B in the direction of the arrow shown, legs 608A and 608B of springs 612A and 612B separate as do securing elements 614A and 614B (the latter not shown) and compressing elements 616A and 616B (the latter not shown). One of the wires in the Figure, wire 639B, passes around pin 634 when pulled. When wires 639A and 639B are released, or pushed in a direction opposite to that shown by the arrow, the clip's elements—its securing elements, compressing elements, and the legs of its springs—move to a position adjacent to each other with the tissue to be resected held between the securing and compressing elements.

After severance of the suspect tissue is effected, excess wire is cut and withdrawn from the endoscope and body.

A fourth embodiment of a surgical compression clip constructed according to the present invention is shown in FIGS. 25A-26B, to which reference is now made.

This embodiment is very similar to the embodiment shown in FIGS. 2-3B and elements are numbered similarly with the inclusion of a prefix digit 7. Similar elements are constructed and operative as in the embodiment presented in FIGS. 2-3B and, accordingly, will not be discussed again.

The present embodiment is different from the embodiment of FIGS. 2-3B in that the bi-directional hinge spring connectors 717 are now joined on the inside of hinge spring arms 708 of spring elements 712A and 712B (best seen in FIG. 4C) and not at the ends of hinge spring arms 8 of hinge spring elements 12A and 12B as in FIGS. 2-3B and FIGS. 4A and 4B. Additionally, and as a direct result of the new positioning of hinge spring connectors 717, spaces 725 must be formed in lateral walls 727 of securing elements 714A and 714B. These spaces are absent in walls 27 of securing elements 14A and 14B as seen and labeled in FIG. 3B. Its necessity with the present clip embodiment is readily seen in FIGS. 25A, 25B, 26A and 26B where hinge spring arms project, at least partially, through spaces 725. It should be noted that securing elements 714A and 714B may be a single integral structure or elements made from several parts joined together by any process known to those skilled in the art, such as by welding. This is true as well for the securing elements shown in previous embodiments and discussed elsewhere herein.

The positioning of connectors 717 on the inside of arms 708 of hinge spring elements 712A and 712B effectively creates a preload that allows the clip to open wider while still applying the forces needed for the necrotic process. An alternative, or additional, technique to achieve preloading is to heat hinge spring elements 712A and 712B and shape them during manufacture.

Figure 25A:
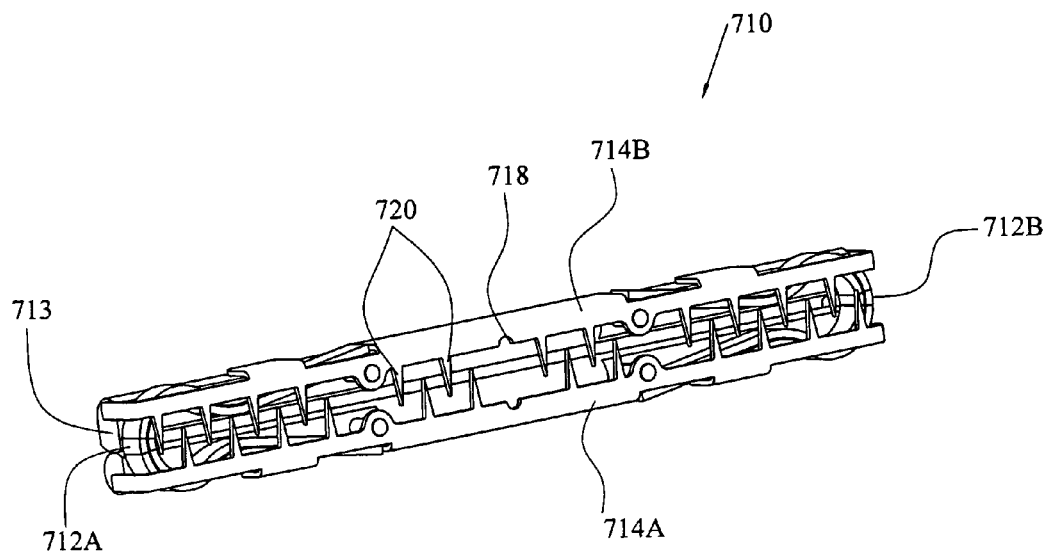
FIGS. 25A and 25B are an isometric top and bottom view of a clip constructed according to a fourth embodiment of the present invention, the clip being in its closed position.
Figure 25B:
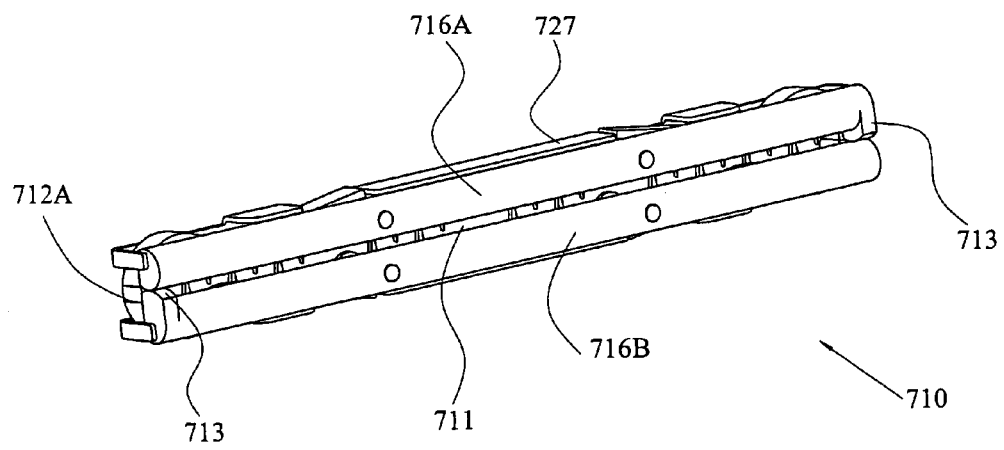

As best seen in FIGS. 25A and 25B, top and bottom views respectively of clip 710, hinge spring elements 712A and 712B exert a force on compressing elements 716A and 716B even when clip 710 is in its closed position.

Clip 710 is effectively preloaded and a gap 711 (best seen in FIG. 25B) exists between securing elements 714A and 714B even when clip 710 is in its closed position. This gap typically, but without intending to be limiting, is in the range of 0.7 to 0.9 mm, which ensures that the force exerted by clip 710 falls to zero before it has a chance to cut through the healing tissue. It should be remembered that when the necrotic process is in an advanced stage, tissue thickness is reduced significantly.

Gap 711, can be formed in one of many ways. Without intending to be limiting, one of these ways is by forming gap forming projections 713 (best seen in FIGS. 25B, 26A and 26B) at the end of one or both ends of compressing elements 716A and 716B.

Figure 27A:
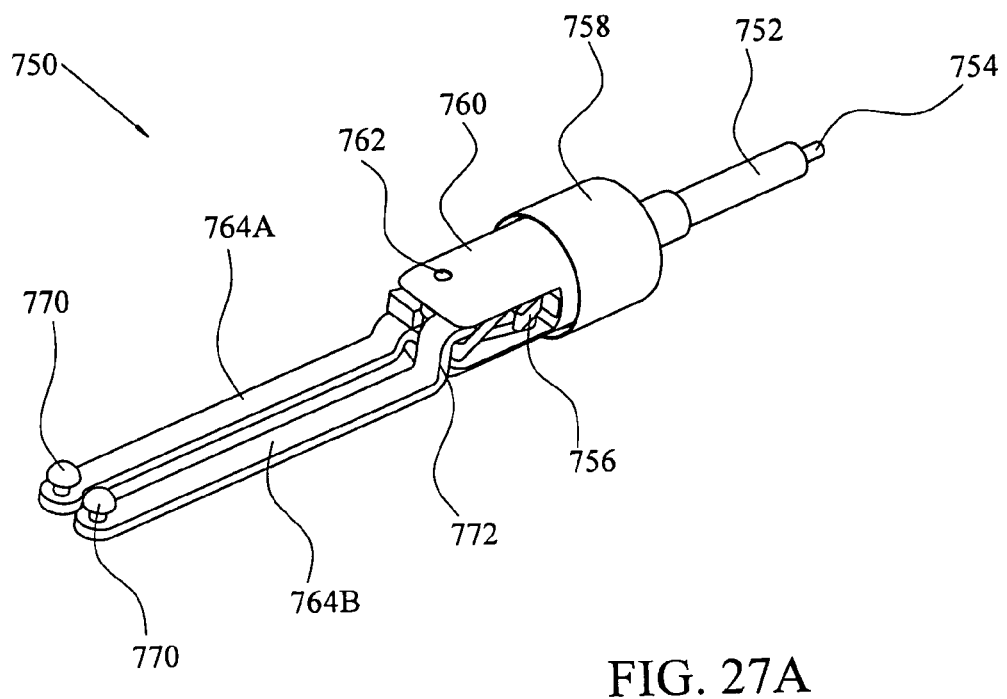
FIGS. 27A and 27B are isometric views of a clip applier constructed according to another embodiment of the present invention, the applier shown in its closed and open position, respectively.
Figure 27B:
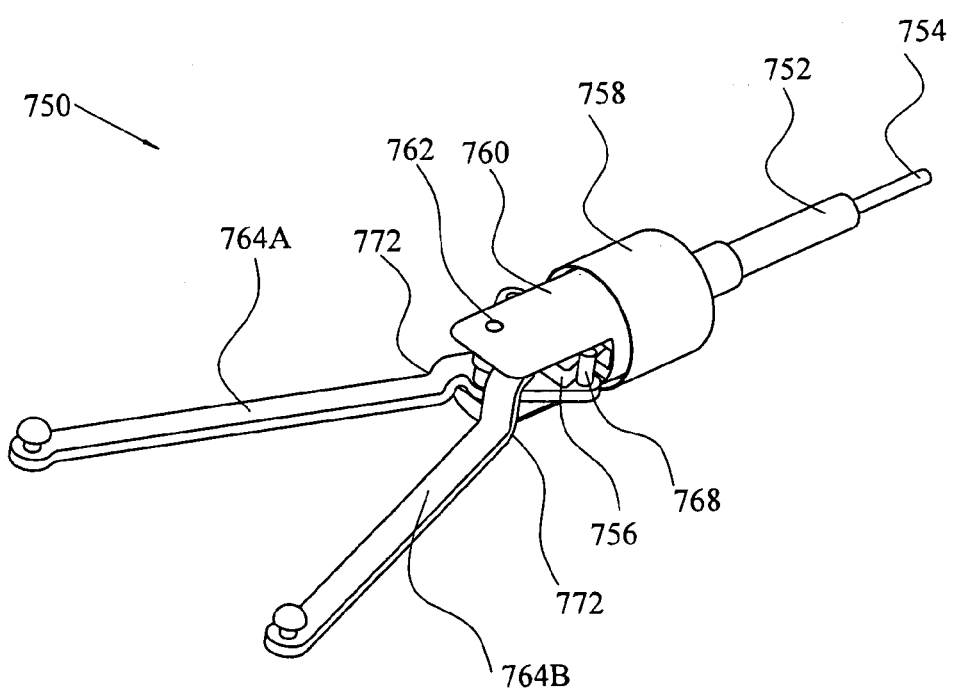
Figure 27C:
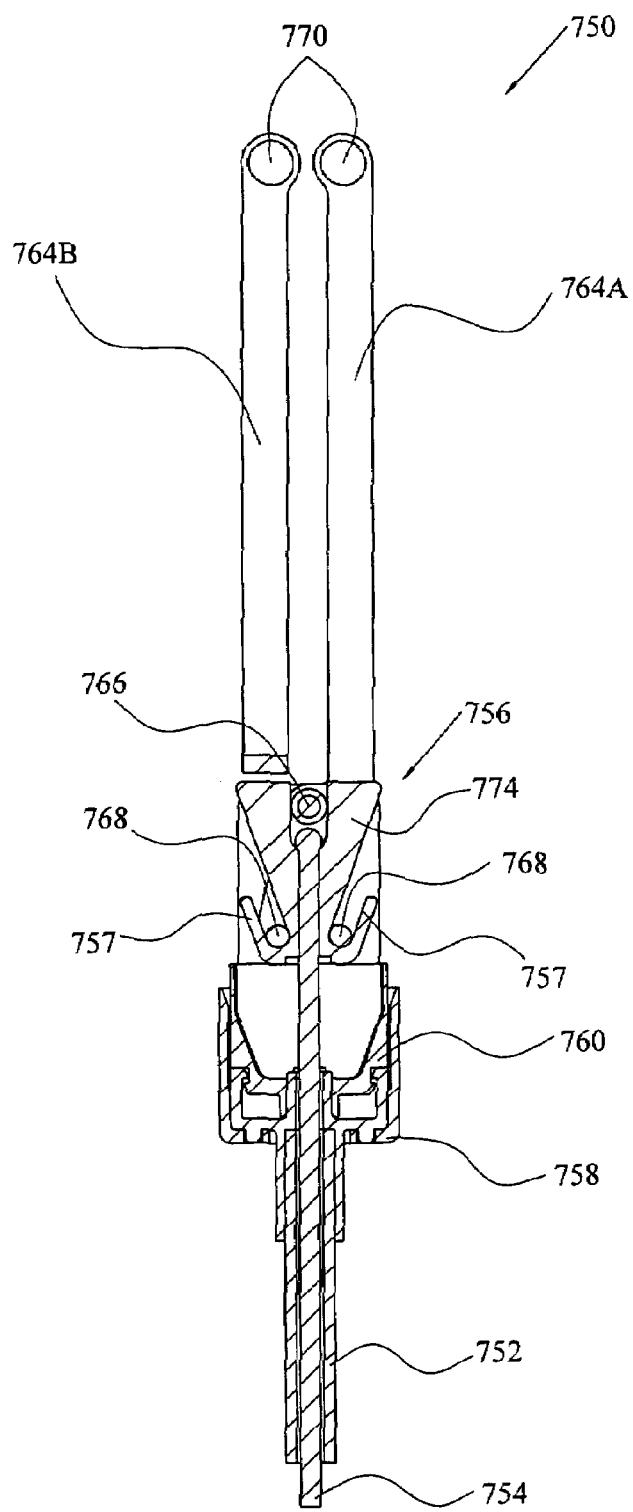
FIGS. 27C and 27D are cross-sectional views of the clip applier shown in FIGS. 27A and 27B, the applier shown in its closed and open position, respectively.
Figure 27D:
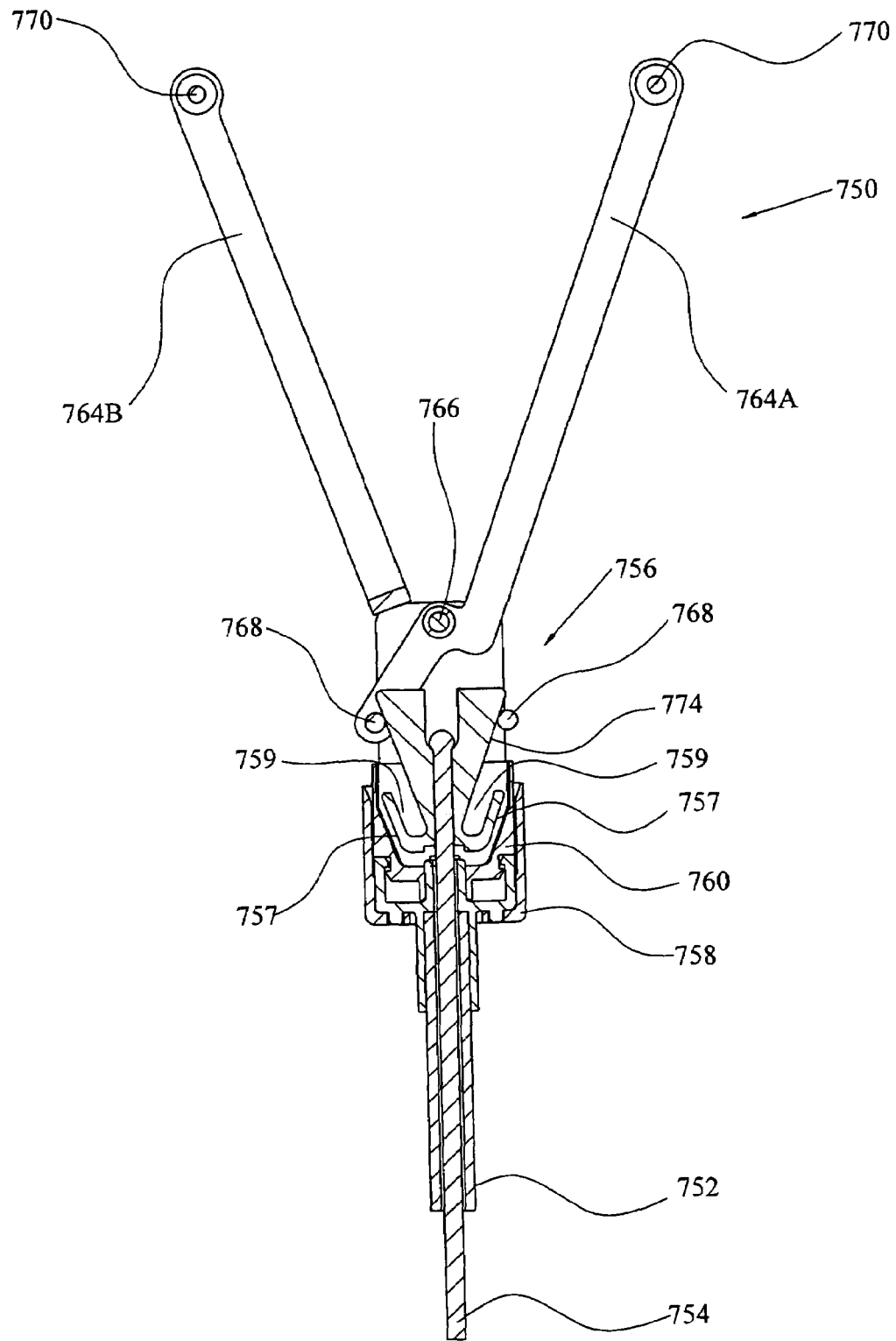
Figure 28A:
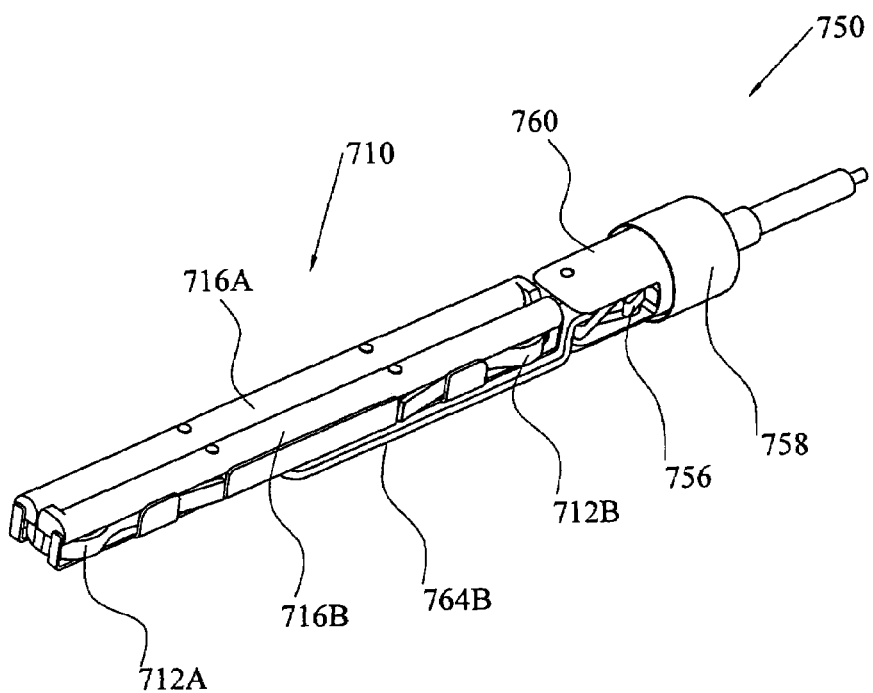
FIGS. 28A and 28B are isometric views of the clip applier shown in FIGS. 27A and 27B constructed in its closed and open position, respectively, when attached to and operating the clip shown in FIGS. 25A-26B.
Figure 28B:
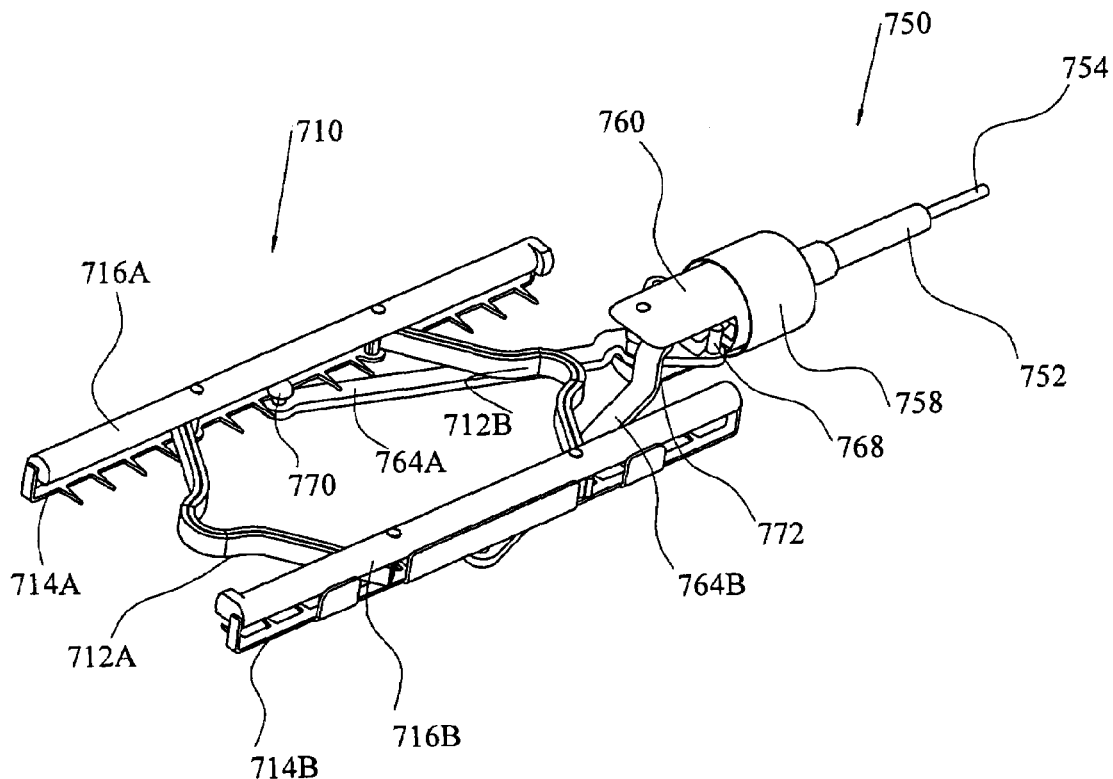

An embodiment of a clip applier 750 that can be used with clip 710 of FIGS. 25A-26B is shown in FIGS. 27A-28B. While discussed in terms of its use with the clip shown in FIGS. 25A-26B, it should readily be understood that applier 750, with little or no modification, may be used with other clip embodiments discussed above. FIGS. 27A and 27B are isometric views of clip applier 750, the applier shown in its closed and open position, respectively. FIGS. 27C and 27D are cross-sectional views of the applier in FIGS. 27A and 27B, respectively. FIGS. 28A and 28B are isometric views of the clip applier shown in FIGS. 27A-27B in its closed and open position, respectively, when attached to and operating the clip shown in FIGS. 25A-26B.

FIGS. 27A-27D, to which reference is now made, shows a wire or cable 754 encased in a sheath 752 which extends toward, and exits from, the body cavity so that it can be operated by a user. Wire (or cable) 754 is attached to a cam 756 which is positioned inside applier body 760, the later covered by applier body cover 758. Applier body 760 at its distal end includes a hole 762 on each of two opposing walls. Applier 750 includes two arms 764A and 764B each having a projection 768 at their proximal end and attachment projections 770 at their distal end. Attachment projections 770 attach to clip 710 (FIG. 25A) at its indentations 718 (FIG. 25A). Arms 764A and 764B each have an aperture (not shown) to receive a pin 766 (FIGS. 27C and 27D) which also passes through holes 762 of applier body 760. Pin 766 serves as an axis around which arms 764A and 764B rotate. Arms 764A and 764B each have a bend 772 in them which allows the positioning of projections 768 on arms 774 of cam 756.

Referring now to FIG. 27C, applier 750 is shown in its closed position. Wire or cable 754 has been pushed in the distal direction, i.e. away from the user, causing attached cam 756 to also move in the distal direction within applier body 760. Due to the force applied by open clip 710 on applier arms 764A and 764B, projections 768 of arms 764A and 764B rotate towards each other around pin 766, towards the center and into the space 759, best seen in FIG. 27D. Space 759 is formed between cam arms 774 and cam flanges 757. This results in applier arms 764A and 764B moving to a position where they are adjacent to each other. When applier arms 764A and 764B are brought together, clip 710 is brought to its closed position as best seen in FIG. 28A.

Referring now to FIG. 27D, applier 750 is shown in its open position. Wire 754 has been pulled in the proximal direction, i.e. toward the user, causing attached cam 756 to also move in the proximal direction in applier body 760. This forces projections 768 of applier arms 764A and 764B to rotate in the outward direction. This causes applier arms 764A and 764B to move to a position where they are spaced apart from each other and where projections 768 of applier arms 764A and 764B are pushed and held apart by the wider distal portion of cam arms 774. When arms 764A and 764B separate from each other as just described, clip 710 is brought to its open position as best seen in FIG. 28B.

Figure 29:
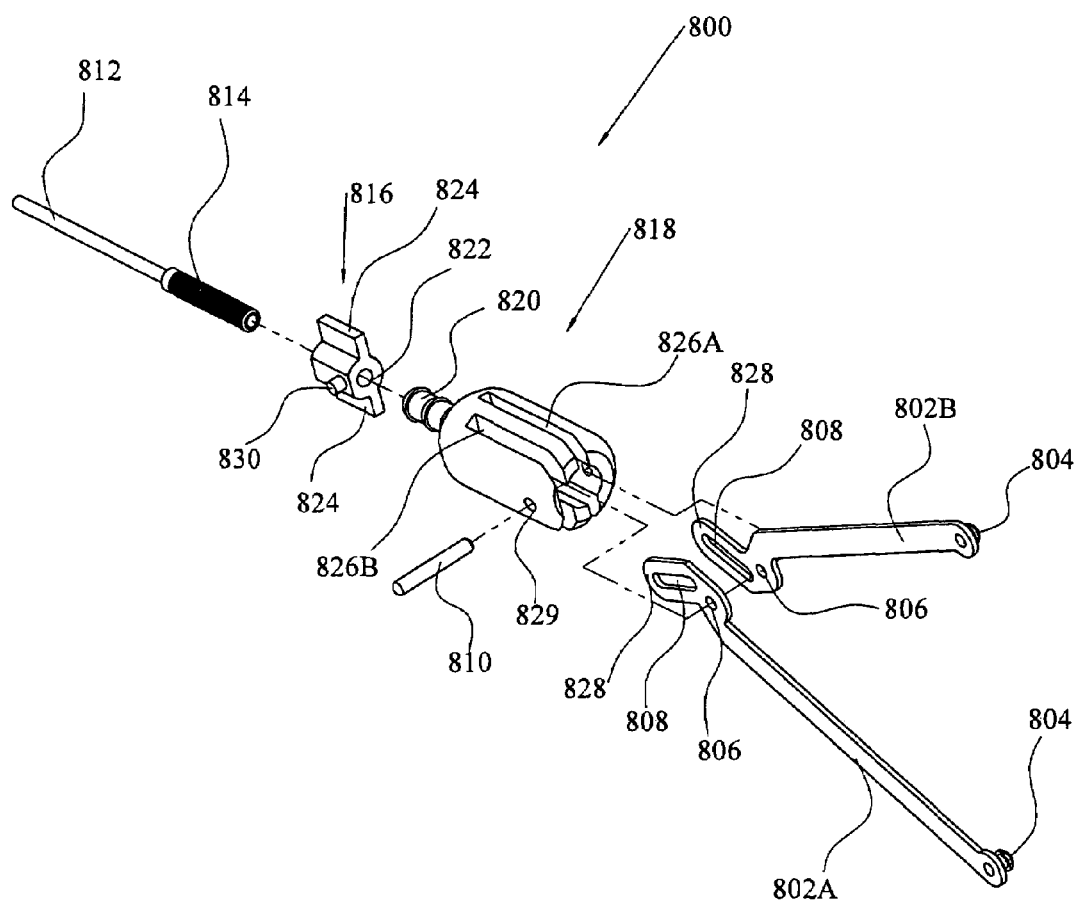
FIG. 29 is an exploded view of another embodiment of a clip applier for use with the clips in the specification herein.
Figure 30A:
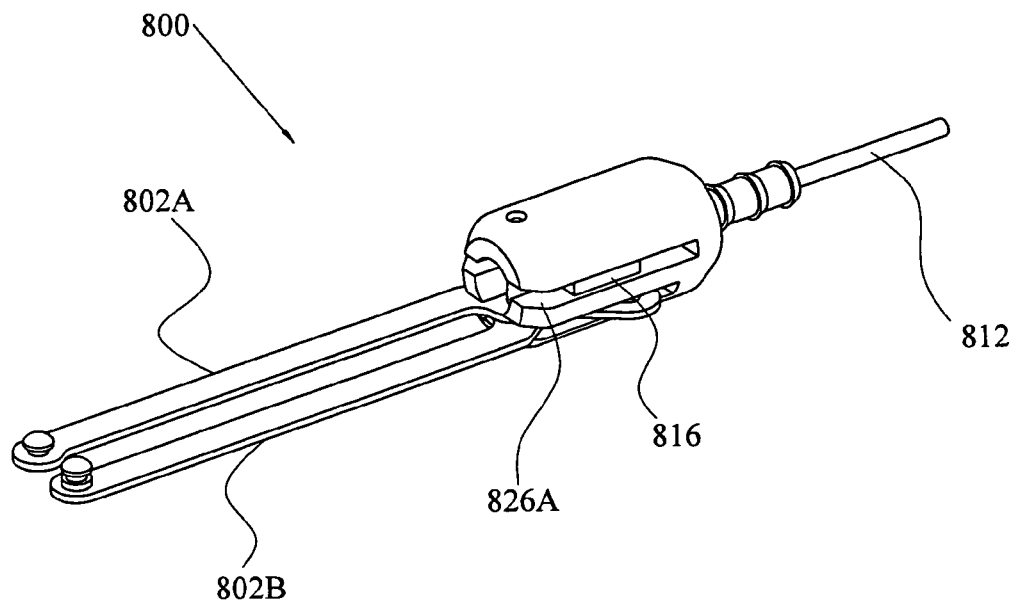
FIGS. 30A and 30B are isometric views of the clip applier shown in FIG. 29 in its closed and open position, respectively.
Figure 30B:
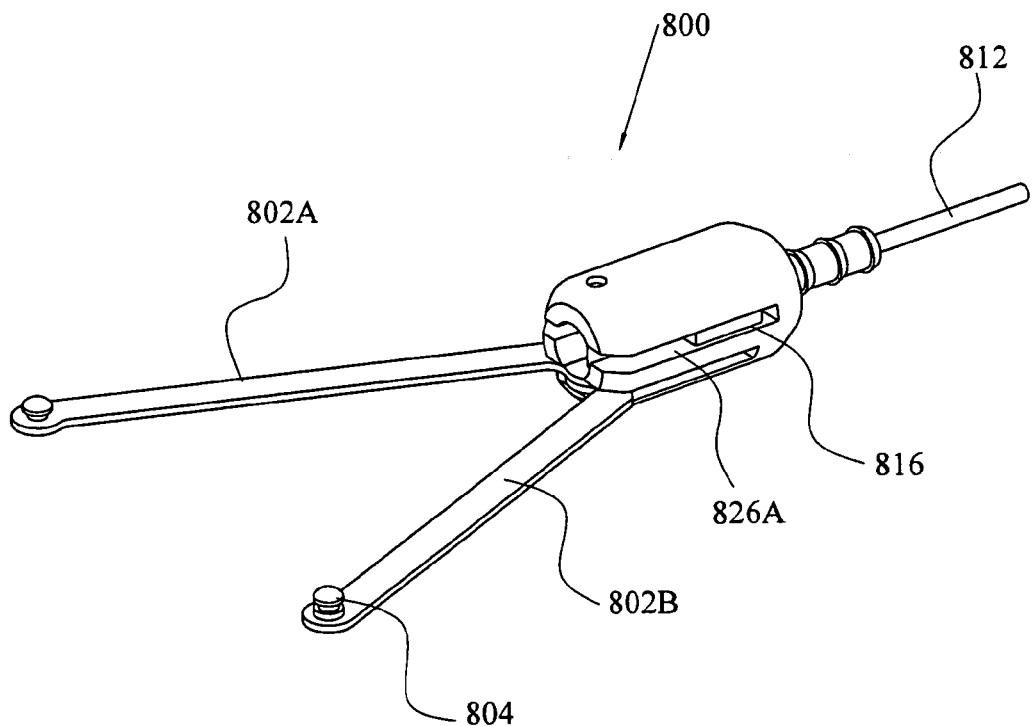
Figure 30C:
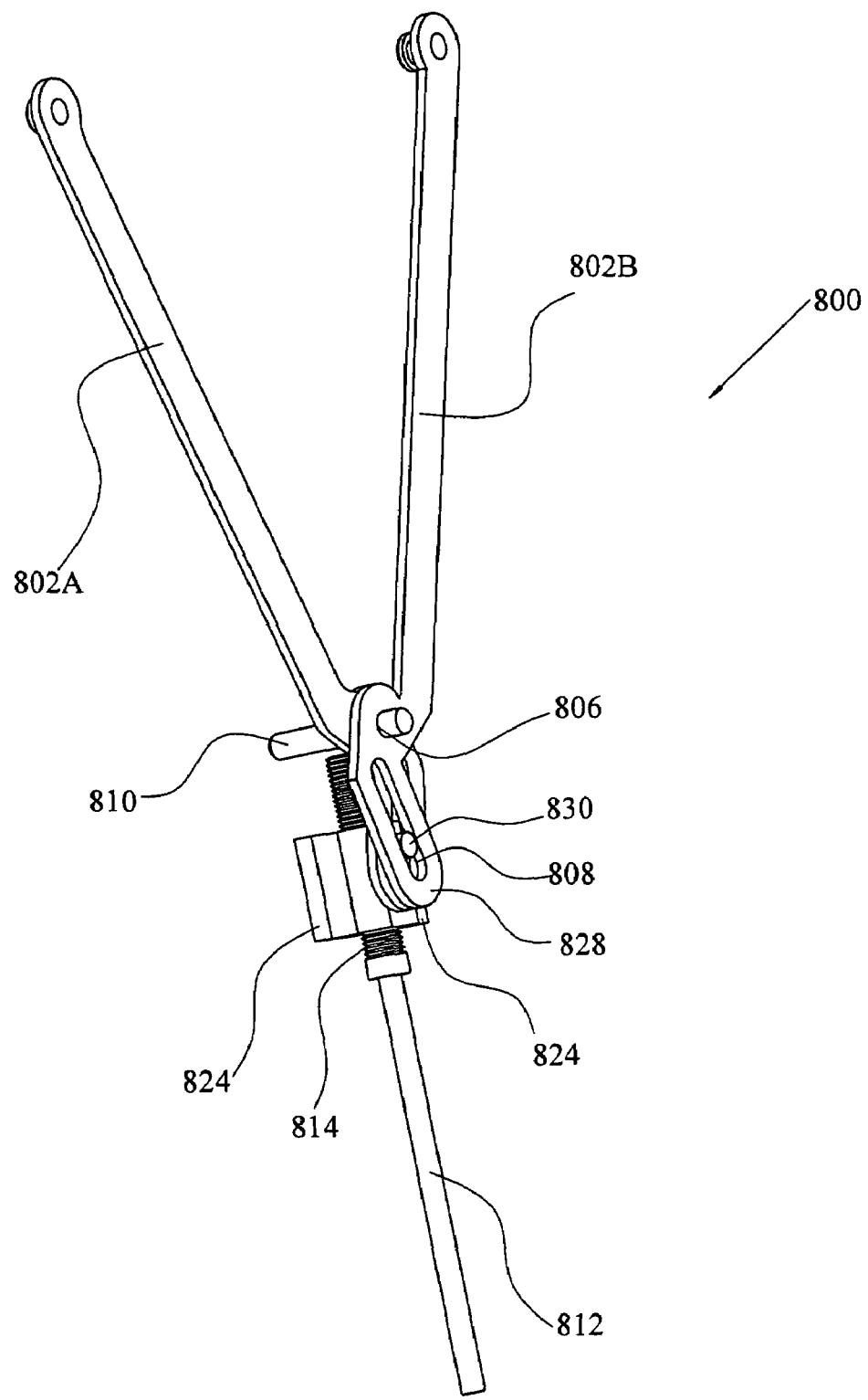
FIG. 30C is a revealed inner view of FIG. 30B.

FIG. 29 through FIG. 30C, to which reference is now made, show various views of another embodiment of a clip applier 800 which may be used with many of the surgical clips discussed herein. FIG. 29 is an exploded view of clip applier 800. FIGS. 30A and 30B are isometric views of clip applier 800 shown in FIG. 29 in its closed and open position, respectively. FIG. 30C is an inner, totally cut-away view of FIG. 30B.

In FIG. 29, there is a wire or cable 812 with a threaded end 814. Wire or cable 812 extends to and exits from the body cavity so that it can be operated by a user. Threaded end 814 of wire or cable 812 is inserted into jagged entry 820 of applier body 818. A casing (not shown) of wire or cable 812 is caught on the jagged surface of entry 820. The threaded end 814 of wire or cable 812 is threaded into a threaded bolt 822 of configuration controller 816 when controller 816 is positioned in guide slot 826A (discussed below), of applier body 818. Configuration controller 816 is formed to also include two wing elements 824 and a projection 830.

Applier body 818 includes a first and a second guide slot 826A and 826B, respectively, and configuration controller 816 is positioned so that it rides in first guide slot 826A. Wing elements 824 of configuration controller 816 move freely in first guide slot 826A. Proximal ends 828 of applier arms 802A and 802B are positioned in and move in second guide slot 826B.

Applier arms 802A and 802B each include an attachment projection 804, a hole 806 and an arm guide slot 808. Projection 804 connects to the surgical clips in a manner similar to that shown elsewhere herein. When the proximal ends 828 of applier arms 802A and 802B are inserted in second guide slot 826B, a pin 810 is inserted through hole 829 of applier body 818 and through holes 806 in applier arms 802A and 802B. This pin acts as an axis of rotation when arms 802A and 802B are brought proximate to or spaced apart from each other. When arms 802A and 802B are inserted into guide slot 826B, projection 830 of configuration controller 816 passes through arm guide slots 808 of applier arms 802A and 802B.

Now referring additionally to FIGS. 30A and 30B, when wire or cable 812 is rotated in one direction configuration controller 816 advances in the distal direction of guide slot 826A with projrvtion 830 (FIG. 29) moving towards the distal end of arm slots 808 (FIG. 29). This causes applier arms 802A and 802B to rotate towards each other and attain their closed position. When wire or cable 812 is rotated in the other direction, configuration controller 816 moves in the proximal direction in guide slot 826A and projection 830 moves towards the proximal end of arm slots 808 causing applier arms 802A and 802B to rotate away from each other and attain their open position (FIGS. 30B and 30C). Wing elements 824 of configuration controller 816 prevent turning of controller 816 when rotated by the threaded end 814 (FIG. 29) of wire/cable 812, thereby allowing for the conversion of rotational motion into translational motion.

A fifth embodiment of a surgical compression clip constructed according to the present invention is shown in FIGS. 31A-44, to which reference is now made.

Figure 31A:
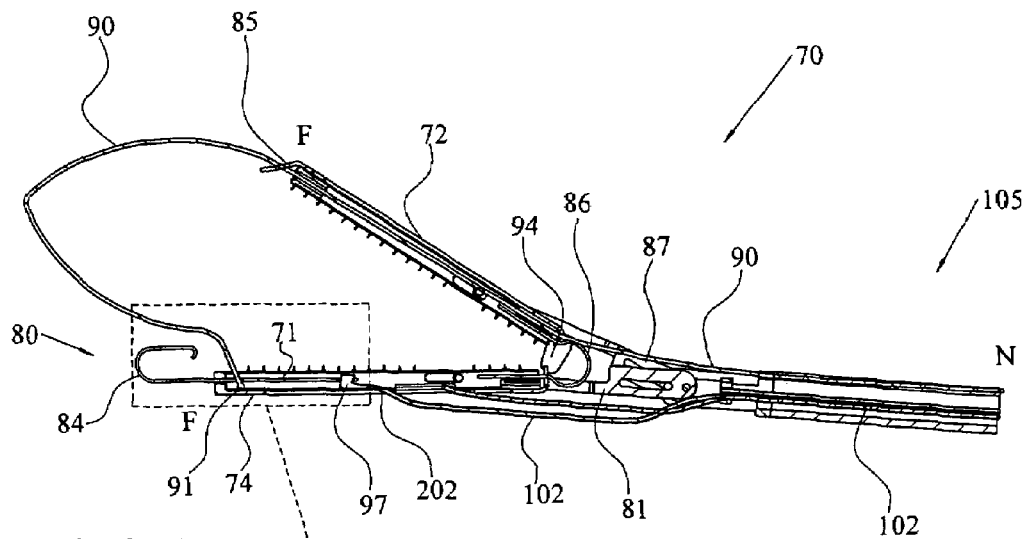
FIG. 31A is a cross-sectional view of a surgical compression clip constructed according to a fifth clip embodiment of the present invention, the clip being in its open position and attached to its associated applier.
Figure 31B:
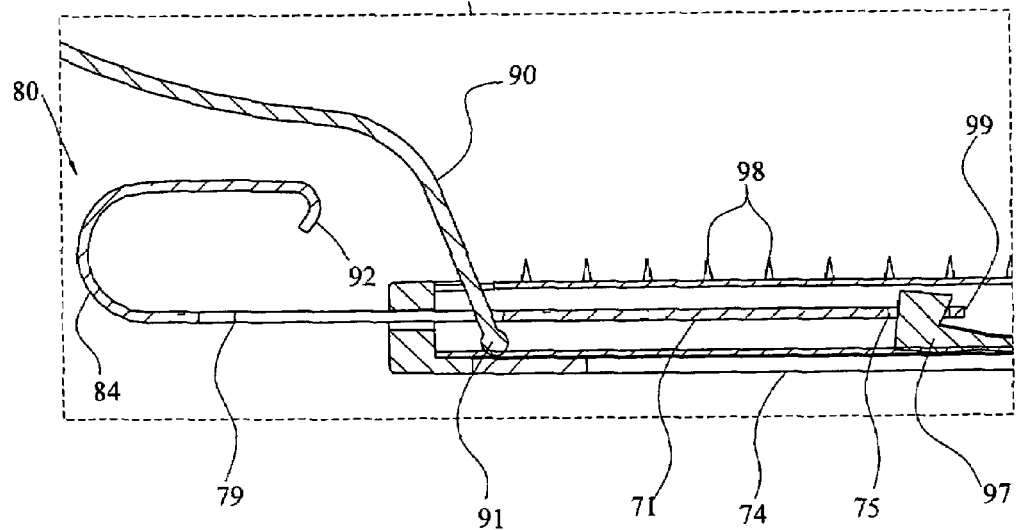
FIG. 31B is an enlarged view of a portion of the distal end of the clip shown in FIG. 31A.

FIG. 31A presents a side cross-sectional view of a surgical compression clip 70, constructed according to a fifth embodiment of the present invention, together with its associated applier 105. FIG. 31B is an enlarged view of the distal end F of a first arm 74 of clip 70, including the clip's latch 80 mechanism.

Clip 70 is formed of a first arm 74 and a second arm 72 which are held apart from each other by a force exerted by a hinge spring 86 (force applier). Hinge spring 86 is made of a shape-memory material, typically, but without intending to be limiting, a Ni—Ti alloy. Arms 72 and 74 are formed having teeth 98 on their faces which lie opposite each other. The teeth are positioned so that they mesh when the arms are brought proximate to each other. The teeth can be formed as an integral part of arms 72 and 74. Alternatively, they can be formed as separate elements and connected to arms 72 and 74 by, for example, welding or by any one of many other techniques known to those skilled in the art.

Figure 40:
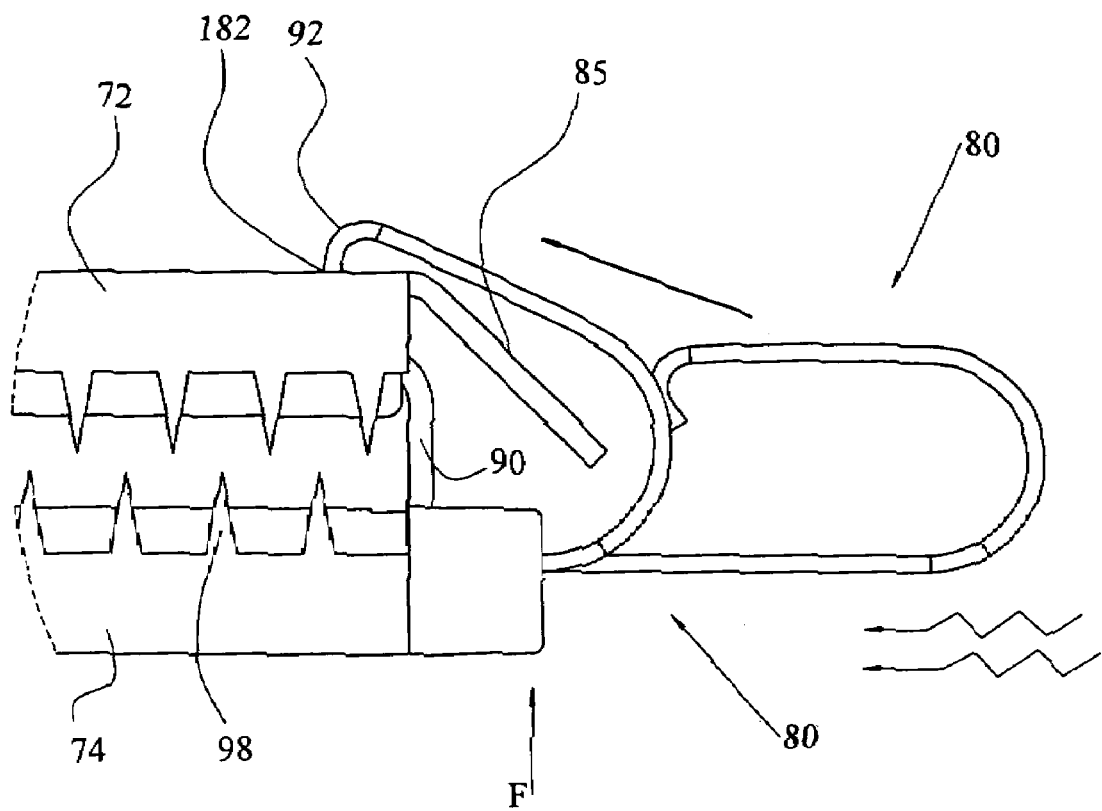
FIG. 40 shows an enlarged view of the clip shown in FIG. 31A including the clip's distal end and its locking process.

Second arm 72 has a slant-shaped guide 85 attached to its distal end F. Guide 85 helps lift latch 80 so that it can snap into place as shown in FIG. 40 to be discussed below. Arms 72 and 74 are typically constructed of metal, e.g. stainless steel or other medical grade metals. However, without being limiting, it may also be constructed of plastic by ejection molding. Arms 72 and 74 are formed so that one end of each arm receives the ends of hinge spring 86.

Restrictor element 94 (best seen in FIGS. 37 and 38) extends from the proximal end of arm 72, and is positioned on the proximal side of the most proximal tooth 98. The function of restrictor element 94 is to prevent tissue from entering into the region occupied by hinge spring 86. This is essential to ensure that all of the tissue grasped will be compressed; tissue that is not compressed will not undergo the required necrotic process.

A latch 80 is inserted in first arm 74 of surgical clip 70. Latch 80 has a crook-shaped end 84 and includes a straight portion 71. Crook-shaped end 84 is also described herein as an engageable end. This is intended to indicate that any construction, not necessarily a crook-shaped construction, capable of engaging with a catch as described below would also be acceptable. Latch 80 is connected to an anchor element 97 which lies inside a rectangular hole 75 (best seen in FIG. 35) positioned at the latch's non-crook shaped end 99. This is best seen in FIG. 31B. Latch 80 is typically formed of a Ni—Ti alloy, but other shape memory materials may also be used. Additionally, other materials having some elasticity may also be satisfactory for use.

Shown in FIG. 31A is a wire 90 which runs from the distal end F of arm 72 to the distal end F of arm 74. One end 91 of wire 90 is ball-shaped and is attached to latch 80 through first arm 74. The second end of wire 90 extends all the way through second arm 72 reaching past proximal end N of clip applier 105, to the proximal, i.e. user, end of an endoscope (not shown). Wire 90 may also be described herein as a cable without any intent at differentiating between the two descriptions.

Attached to anchor element 97 at the non-crooked shaped end 99 of latch 80 is a cable 102 which extends through clip applier 105 past its proximal end N to the proximal end of the endoscope N (FIG. 1A) where an applier actuator (e.g. 306 or 308 in FIG. 1A) is located.

Arms 72 and 74 may be considered to consist of both compressing elements and securing elements and in this way be subsumed into the overall rubric of the other clips discussed herein. In the Figures, each arm appears as a single piece but essentially it consists of a bar, typically but without intending to be limiting, with a rounded cross section having teeth joined to it. The toothed portion (securing element) may by welded to the round bars (compressing elements) or otherwise joined or produced as an integral part of the round bars. The round elements are typically hollow and they can be considered cylindrical. The hollow arms allow insertion therein of hinge spring 86, latch 80, and wires 90 and 102 used to operate clip 70.

Figure 32:
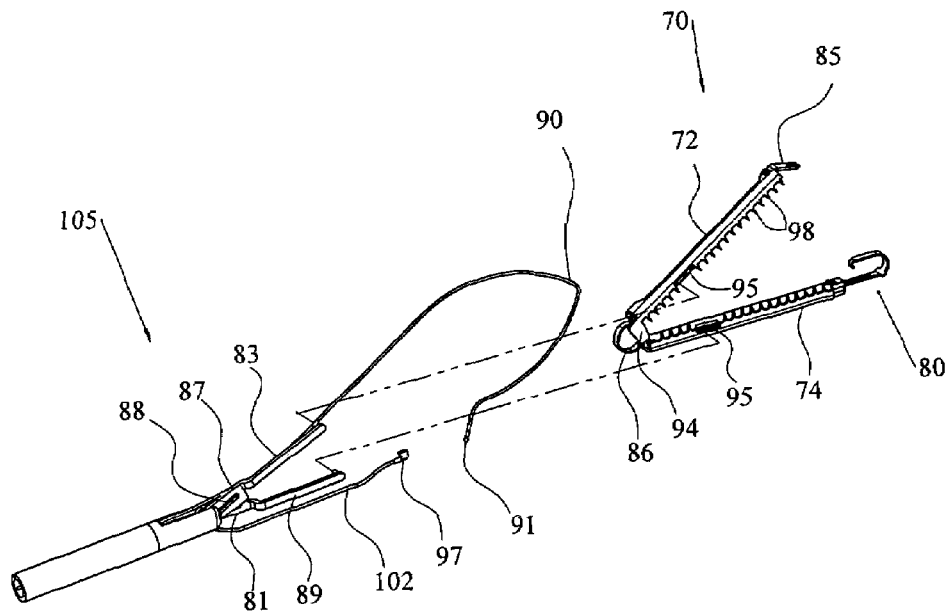
FIGS. 32 and 33 are different partially exploded views of the surgical compression clip and applier in FIG. 31A.
Figure 33:
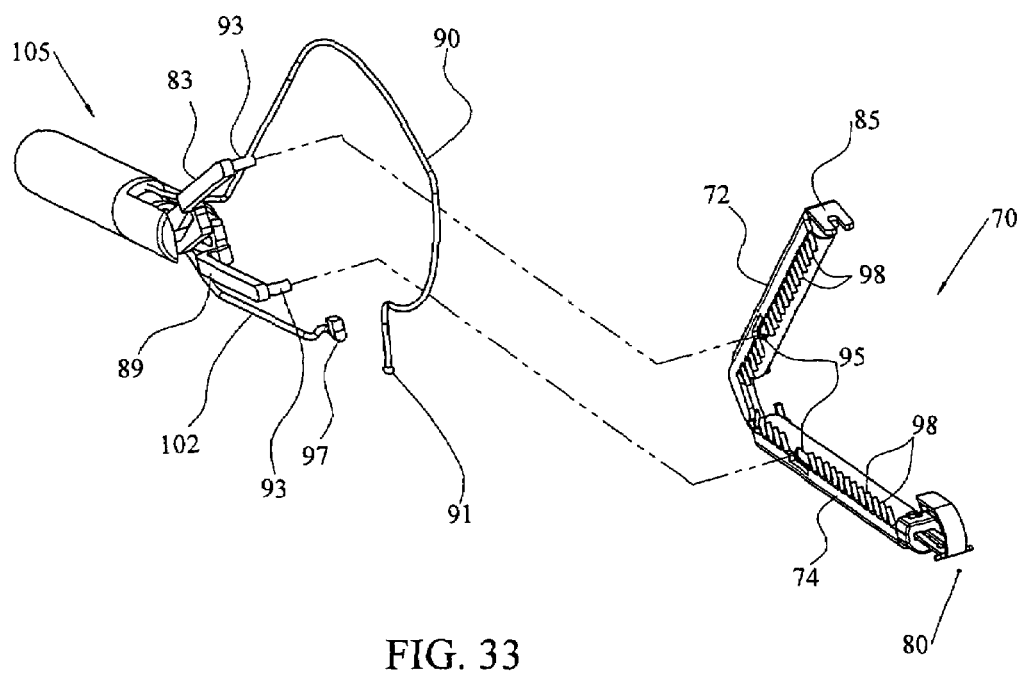

FIGS. 32 and 33 are partially exploded views of the elements of surgical clip 70 and clip applier 105 shown in and discussed in conjunction with FIGS. 31A and 31B. FIGS. 32 and 33 also show applier arms 83 and 89 of applier 105 to which first and second arms 72 and 74, respectively, of clip 70 are joined. Attachment is effected by applier arm projections 93; projections 93 extend substantially transversally from the ends of applier arms 83 and 89. Applier arm projections 93 are positioned in projection receptor spacings 95 on arms 72 and 74 when applier 105 is engaged to clip 70.

Figure 34:
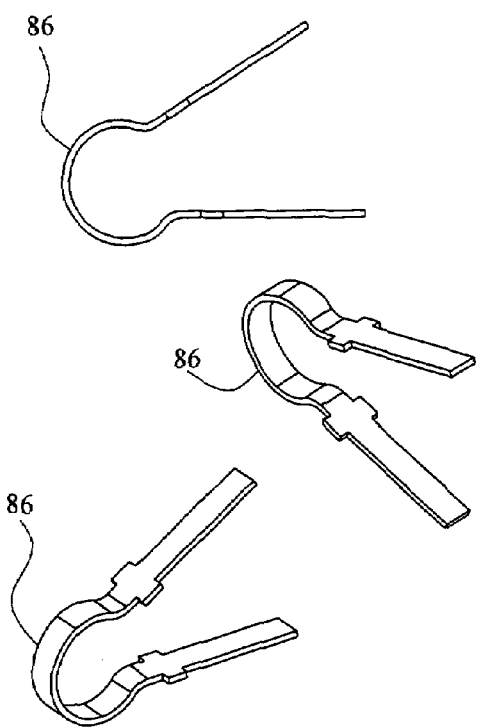
FIG. 34 shows different views of the shape-memory spring element of the clip in FIG. 31A.

FIG. 34 shows several isometric and side views of a typical, but non-limiting, hinge spring 86 design.

Figure 35:
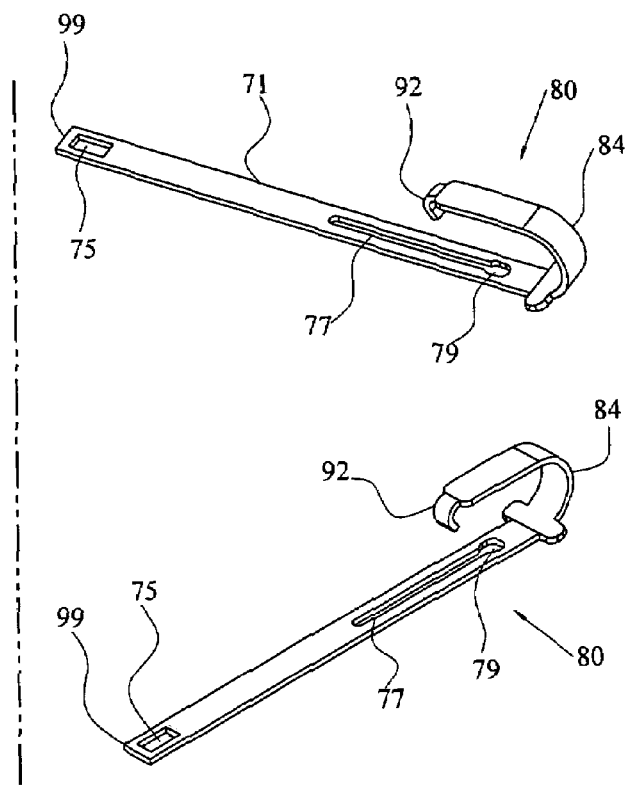
FIG. 35 shows different views of the latch arm of the clip presented in FIG. 31A.
Figure 43:
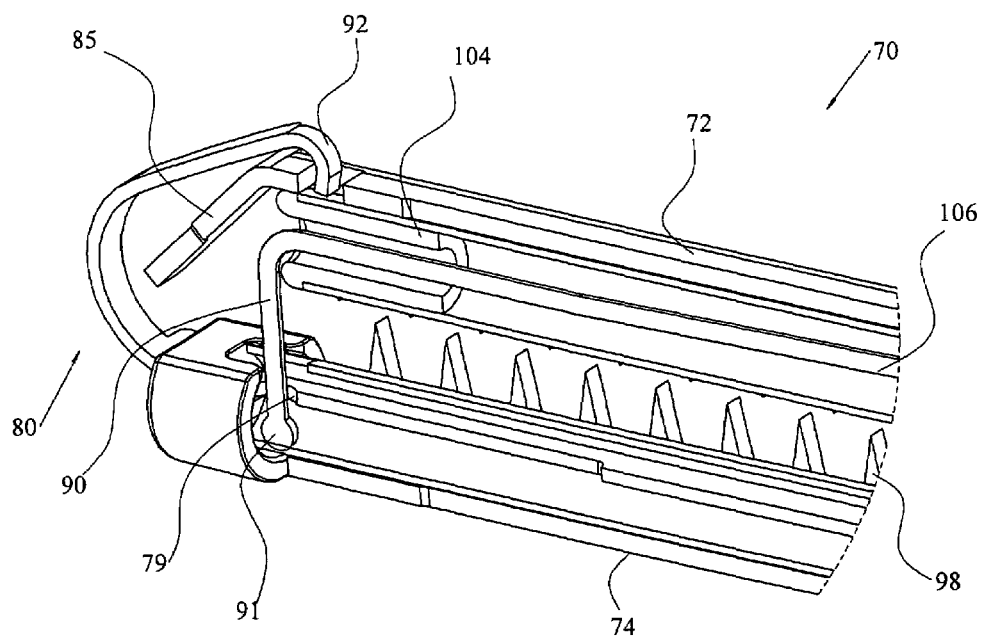

FIG. 35 shows the details of latch 80. The straight section 71 of latch 80 includes a straight slot 77 with a round hole 79 at its distal end. The end 91 of wire 90 (FIG. 31B) is inserted and held in slot 77, the diameter of end 91 being greater than the width of slot 77. When clip 70 is completely positioned around the tissue to be resected, latch 80 is snapped into place, as discussed in greater detail below. As latch 80 snaps into place, wire 90 is then detached naturally from latch 80 and from clip 70 through hole 79 (FIGS. 35 and 43). After wire 90 is freed from latch 80, wire 90 is pulled entirely through second arm 72 toward the proximal end of the endoscope where it exits the endoscope and the body. A rectangular hole 75 at the end 99 of straight section 71 of latch 80 is used to anchor latch 80 to anchor element 97 (FIG. 31B) which is used by the user to pull latch 80.

FIG. 35 also shows that at the end of crook-shaped end 84 of latch 80 is a curved latch snout 92. Curved snout 92 is intended to catch in latch hole 182 discussed below in conjunction with FIGS. 38 and 40. This ensures that latch 80 snaps into place when clip 70 is in its closed position, thereby ensuring compression of the tissue between arms 72 and 74.

Figure 36:
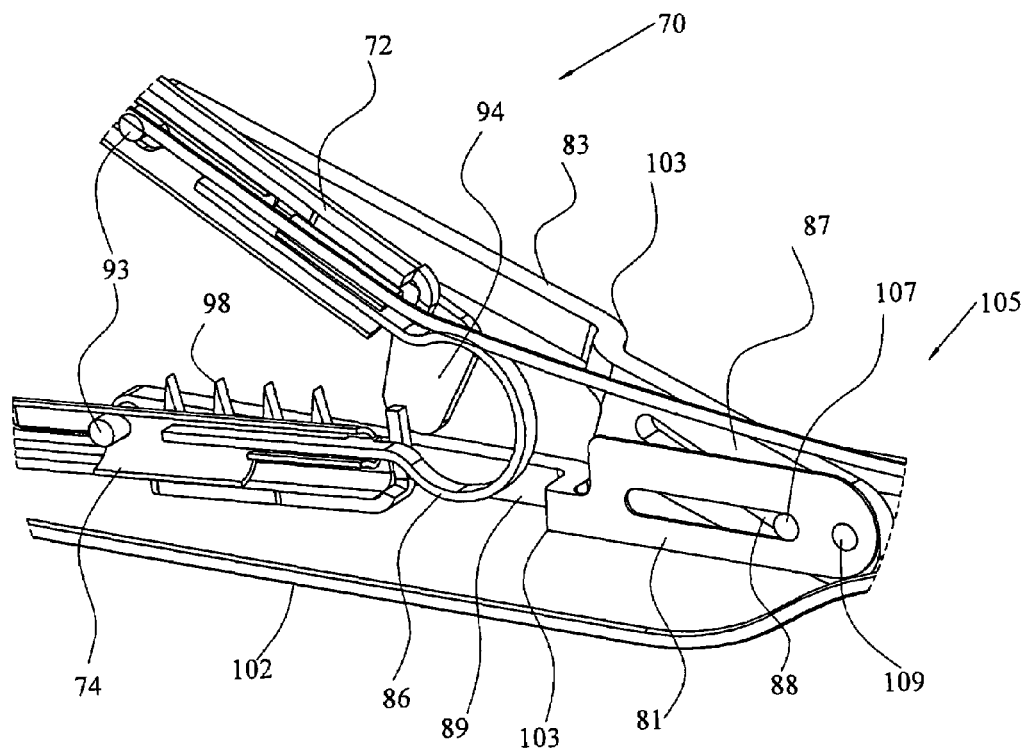
FIG. 36 shows an isometric view of the clip's spring element at the hinge region of the clip shown in FIG. 31A.
Figure 37:
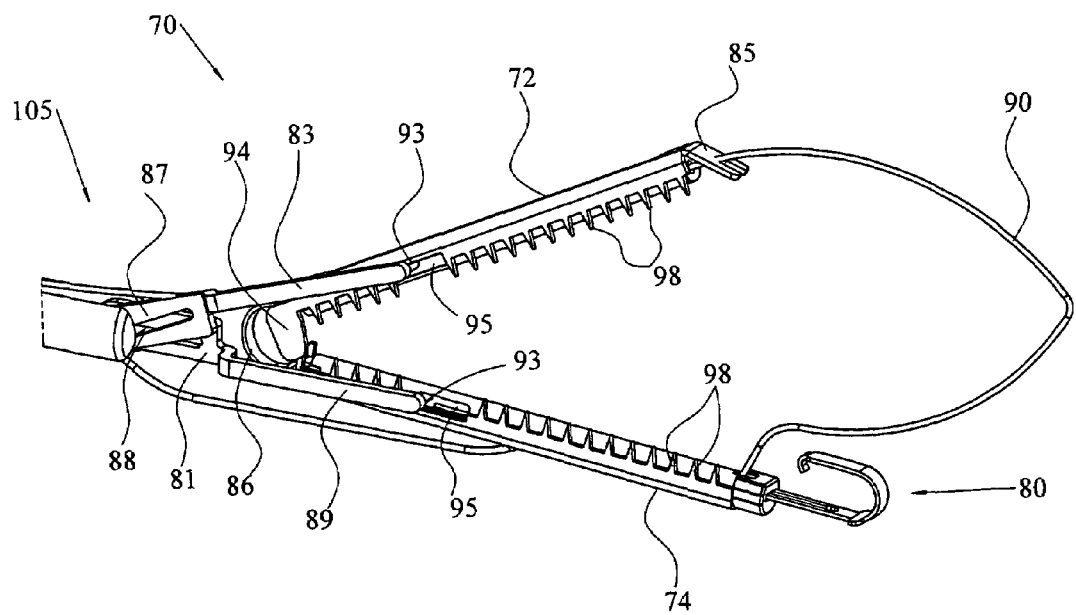
FIG. 37 shows an isometric front side view of the clip in FIG. 31A, the clip in its open position.

FIG. 36 shows an expanded isometric side view of the hinge spring 86 section of clip 70 and the section of clip applier 105 proximate to this section of clip 70. FIG. 37 shows an isometric front side view of clip 70, wire 90 and the distal end of applier 105. Both FIGS. 36 and 37 show clip 70 in its open position.

FIG. 36 shows hinge spring 86 as being inserted into arms 72 and 74 of clip 70. FIG. 37 shows the attachment of applier arms 83 and 89 which close clip arms 72 and 74 by exerting a force counter to the force exerted by hinge spring 86. The latter tends to force clip 70 open. Applier arms 83 and 89 are attached to arms 72 and 74, respectively, by applier arm projections 93, the latter being inserted into the clip's projection receptor spacings 95. Projections 93 and spacings 95 are also shown in FIG. 33. FIG. 36 also shows that applier arms 83 and 89 are integrally formed with pushing attachments 87 and 81, respectively. These are typically, but not necessarily, single piece elements, that is elements 89 and 81 form a single integral piece and elements 83 and 87 form another single integral piece. Alternatively, elements 83 and 87 (and 89 and 81) can be welded together from two or more separate structures.

Figure 38:
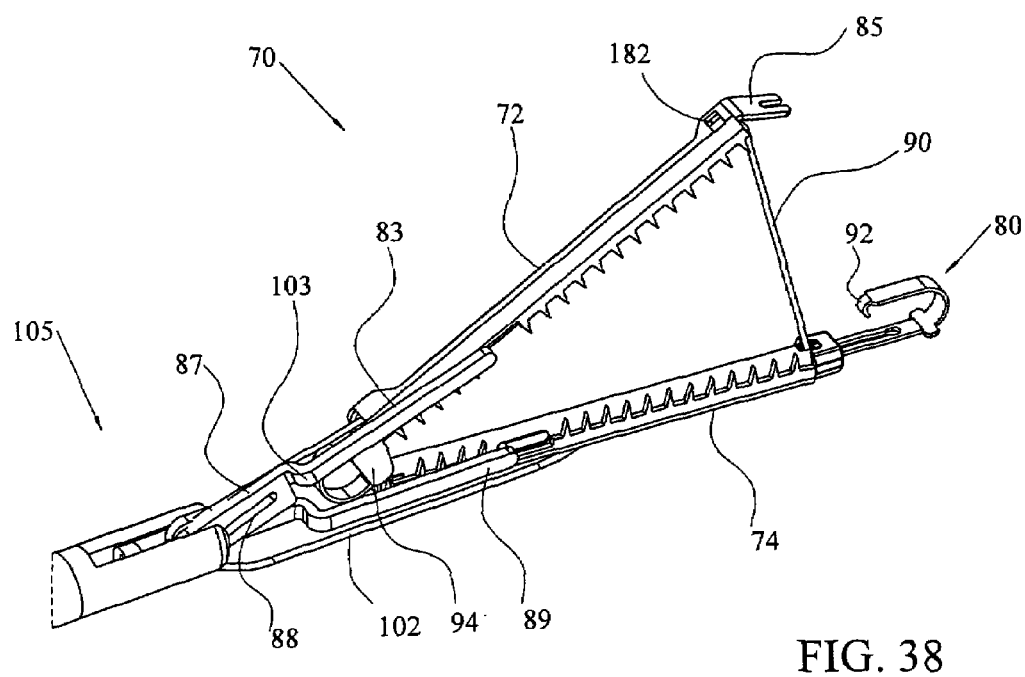
FIGS. 38 and 39 show different views of the clip in FIG. 31A where the wire of the clip has been drawn taut.

These pieces include a bend 103 readily recognizable in FIGS. 36 and 38; bend 103 is required to ensure planarity of the pushing device.

Pushing attachments 87 and 81 each has an applier arm slot 88 in which a pushing attachment pin 107 moves when rotating pushing attachments 81 and 87 around pin 109 (FIGS. 31A and 36).

Figure 39:
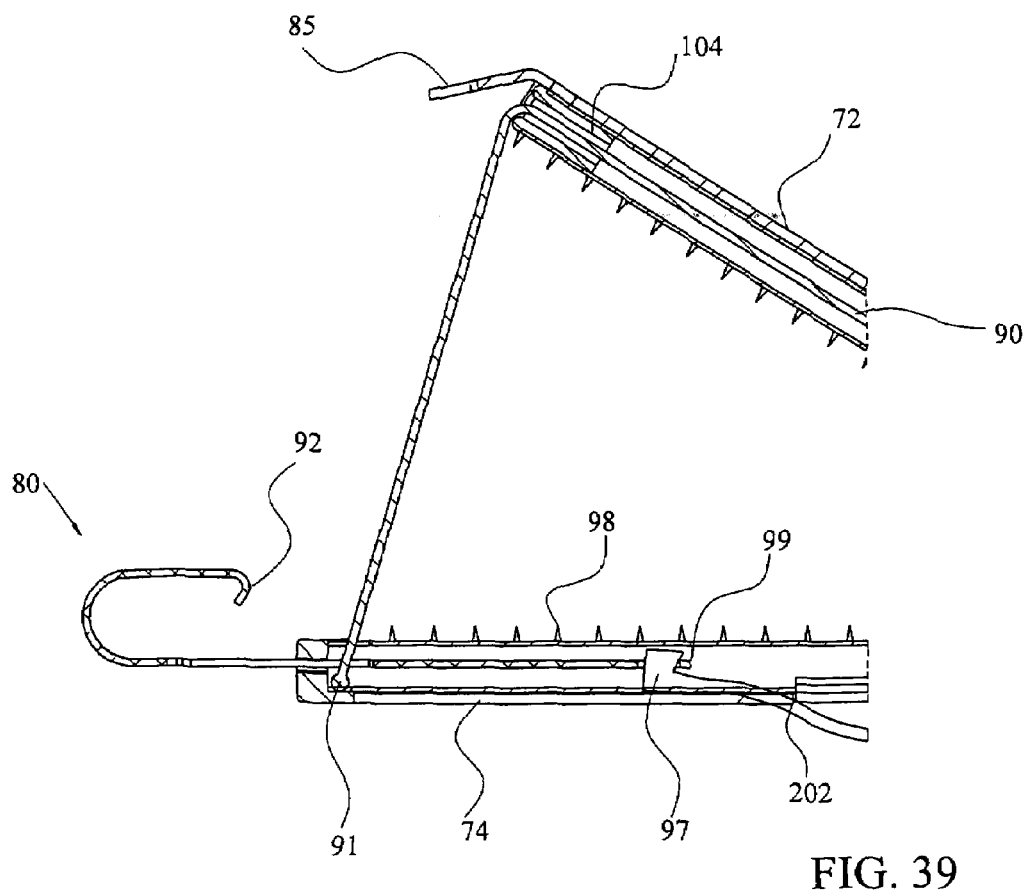

FIGS. 38-39 show different views of clip 70 and the distal end of clip applier 105 when wire 90 is pulled taut as a first step in closing applier 105. The taut wire keeps tissue (not shown) from slipping out when positioned between arms 72 and 74 as these arms move toward each other in a scissor-like or clamp-like fashion.

The wire is pulled taut after the tissue has been brought completely into clip 70 in its open position; the tissue is grasped and held between arms 72 and 74 and wire 90. Continuing to pull wire 90 brings distal end F (FIG. 31A) of arm 72 close to distal end F (FIG. 31A) of arm 74 until arm 72 is pressed against the tissue situated between arm 72 and arm 74. At this stage, latch 80 is brought to its locking position as will be described below. Wire 90 enters arm 72 through wire aperture 104. Wire section 106, best seen in FIG. 41, extends to the proximal end of the endoscope (not shown) and is pulled at that end when it is desired to bring wire 90 to its taut position between arms 72 and 74 of the clip.

Figure 42:
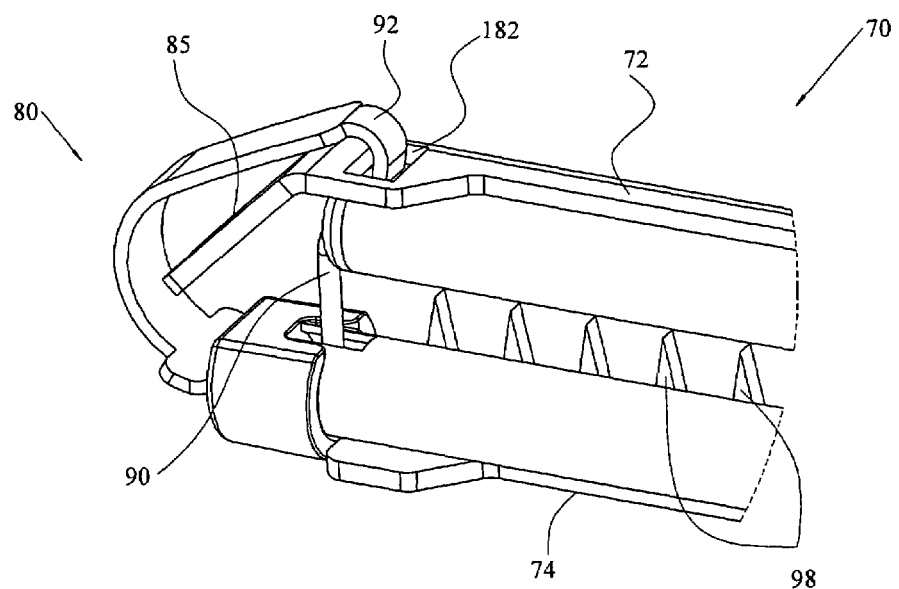
FIGS. 42 and 43 show additional enlarged views of the distal end of the clip shown in FIG. 31A, the clip being in its closed position.

FIG. 40 shows the distal end F of clip 70 and the locking action of latch 80. Between arms 72 and 74, tissue (not shown) is positioned and wire 90 is pulled taut. At that point, the distance between clip arms 72 and 74 is small. When arms 72 and 74 are in apposition, latch 80 is pulled by cable 102 (see FIGS. 31A and 37 for example) in a proximal direction indicated by the wavy double arrows. As latch 80 moves in the direction of those arrows, the rounded latch head slips (indicated by the single solid arrow) over slanted guide 85 until it contacts arm 72. It then latches when latch snout 92 (FIGS. 35 and 38) enters latch hole 182 (FIGS. 38 and 42). When in that position, latch 80, in concert with hinge spring 86 (force applier), exert a compressive force which acts in a line between arms 72 and 74. In the latched stage, arms 72 and 74 are separated somewhat, the gap between them arising from the thickness of the gripped tissue.

It should readily be understood that any other suitable catch structure can be used in place of latch hole 182. The choice of a hole here, functioning as a latch catch, should be considered as exemplary only. A protrusion with which latch 80 can engage would work equally as well. In fact, any engagement means that can engage and hold latch snout 92 of latch 80 is contemplated by the present invention.

The tissue situated between arms 72 and 74 of clip 70 prevents the clip from fully tracking clip applier 105 and returning to its completely closed position. As a result of this lack of complete tracking, applier arm projections 93 disengage from projection receptor spacings 95 by themselves and applier 105 falls away from clip 70.

As noted above, the shape-memory elements used to effect opening or closing of the compression clips described herein are typically described as hinge springs. However, these elements can more generally be classified as and called force appliers. Latch 80, because it is typically formed of shape memory materials, acts as a force applier that holds compression clip 70 closed.

Figure 41:
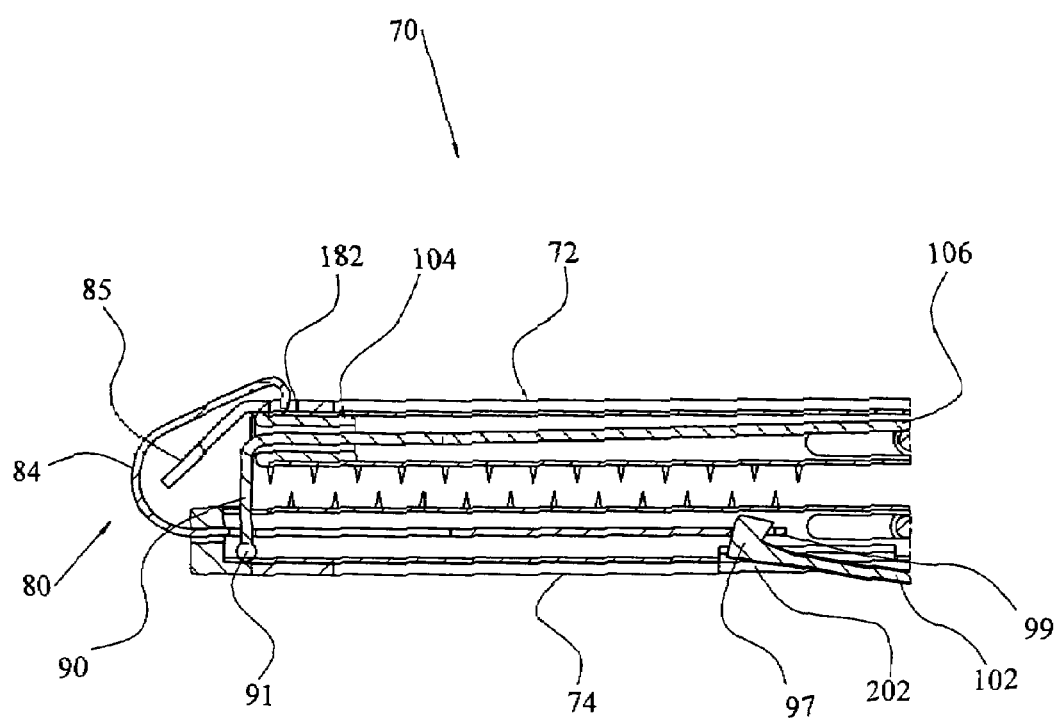
FIG. 41 shows an enlarged cross-sectional view of the distal end of the clip shown in FIG. 31A, the clip in its latched position.

FIGS. 41-43 show three different views of surgical compression clip 70 after latching as described above in conjunction with FIG. 40. FIG. 41 best shows exit hole 202 through which cable 102 is attached. Compression clip 70, by anchoring latch 80 to latch hole 182, brings anchor element 97 to exit hole 202, allowing anchor element 97 to naturally exit through hole 202. Both cable 102 and anchor element 97 are then pulled toward and through applier 105. From there they are pulled toward the proximal end of the endoscope and withdrawn from the body.

Figure 44:
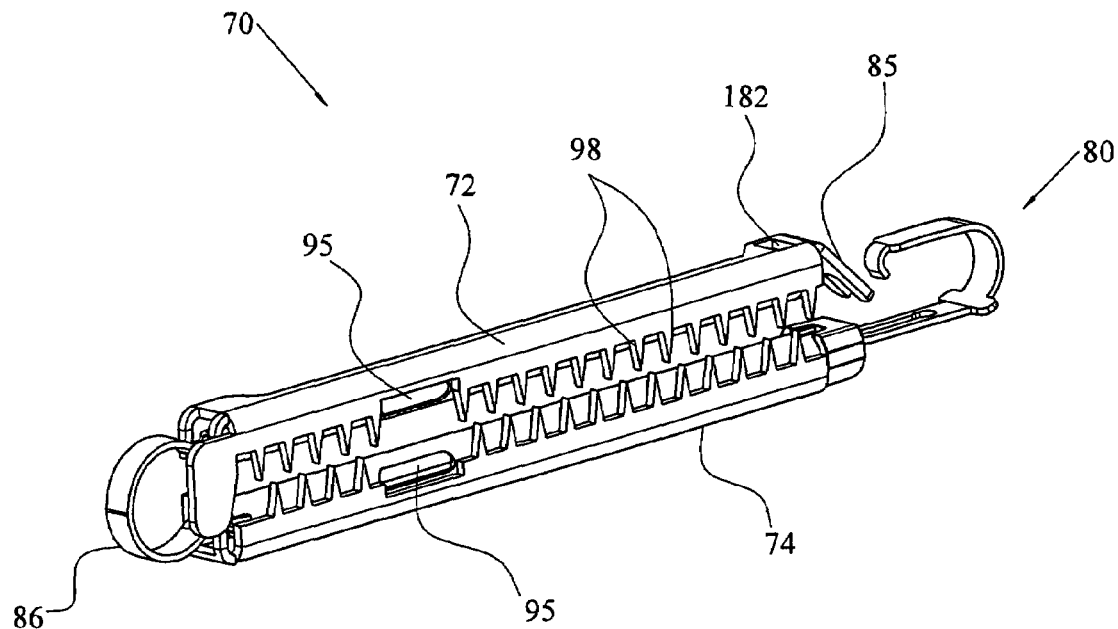
FIG. 44 shows an isometric view of the clip shown in FIG. 31A, the clip in its closed position and ready for insertion into a clip applier.

FIG. 44 shows an isometric view of a closed, but unlatched, surgical compression clip 70 constructed according to the embodiment shown in FIGS. 31A-43. FIG. 44 reflects the position of clip 70 as it is delivered to the site of a lesion by applier 105 via a working channel of an endoscope or via a secondary lumen of a multi-lumen sleeve encasing an endoscope. The use of multi-lumen sleeves is discussed below in conjunction with FIGS. 45-53.

Applier 105 is attached to clip 70 via applier arm projections 93 of applier arms 83 and 89 (see for example FIG. 33) at receptor spacings 95 on arms 72 and 74. In the closed but unlocked position of FIG. 44, the force exerted by applier arms 83 and 89 is counter to the force exerted by hinge spring 86. The force provided by applier 105 exerts a force which holds arms 72 and 74 adjacent to each other while clip 70 is being advanced within the endoscope (or sleeve lumen) to the lesion. At the site of the lesion, the force exerted by applier 105 is released and the clip opens.

Tissue is brought between the clip arms, the clip is closed, the lesion is severed and the site of the severed lesion is compressed between arms 72 and 74 of the clip 70 until necrosis and healing occurs. The entire process is discussed in greater detail below.

It should be noted that wire 90 is pushed forward once clip 70 approaches the suspect lesion. This relaxes wire 90 and enables the user to place it over, and/or around, the lesion. The relaxed, extended wire has a loop with an increased area through which the lesion can be pulled. With clip 70, the open arms 72 and 74 of the clip may be slid from the side of the pulled tissue after the polyp is positioned in the area between arms 72 and 74 and wire 90; this is unlike with clips 10 and 710 (FIGS. 2-3B and FIGS. 25A-26B), for example, where the polyp must be pulled through the arms of these latter clips using a grasper (discussed further below). Because of the use of wire 90, larger polyps may be treated.

The multi-lumen sleeve element of the present invention is shown in FIGS. 45-53, to which reference is now made.

Figure 45:
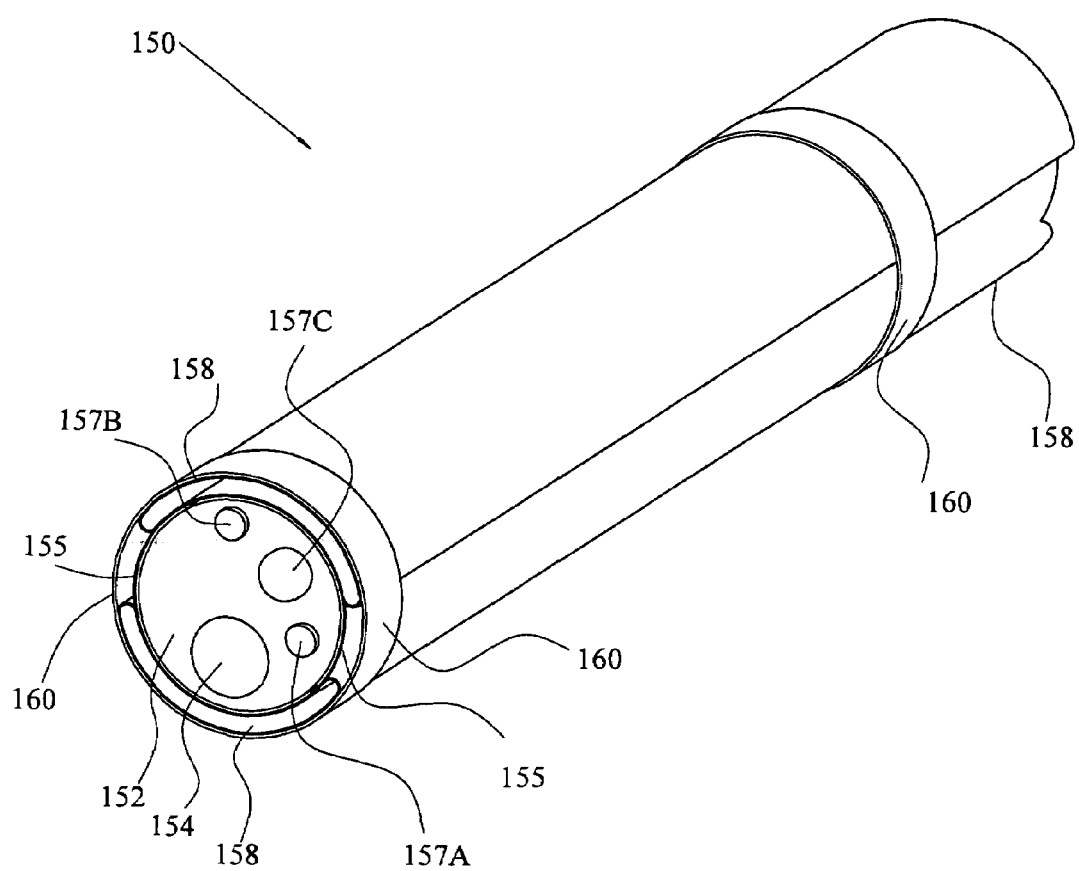
FIG. 45 is an isometric view of an endoscope body encased in a multi-lumen sleeve, the sleeve having collapsed secondary lumens.
Figure 46:
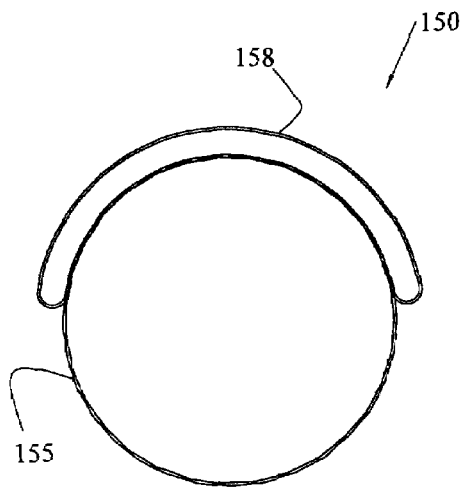
FIGS. 46-49 show various configurations of multi-lumen sleeves with collapsed secondary lumens.
Figure 47:
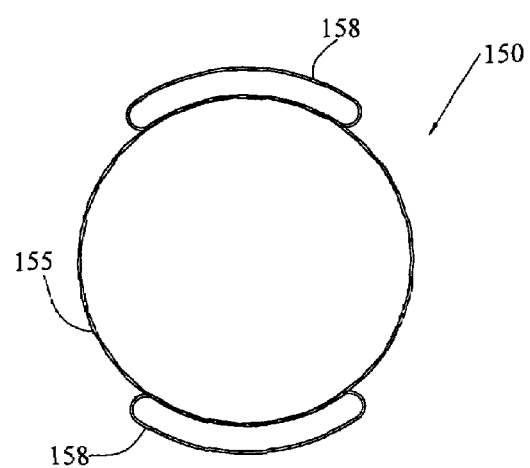
Figure 48:
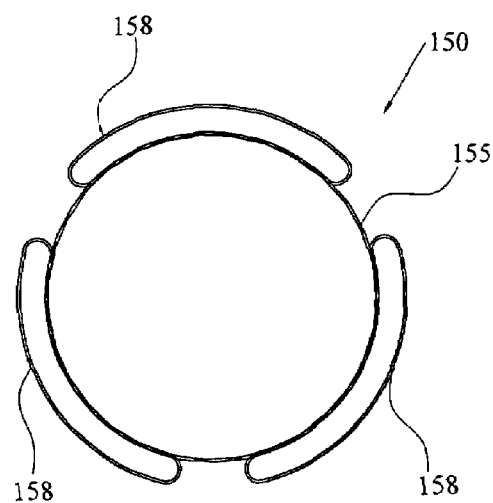
Figure 49:
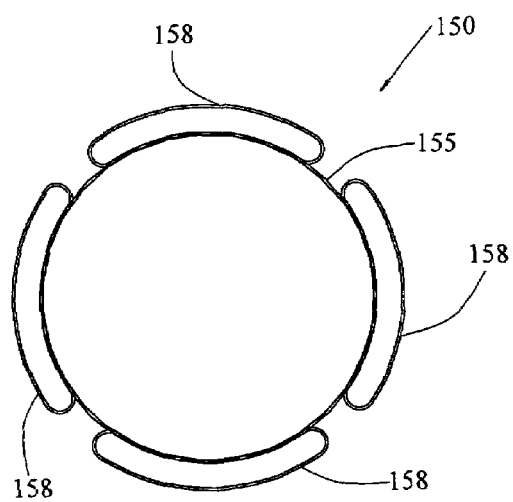
Figure 50:
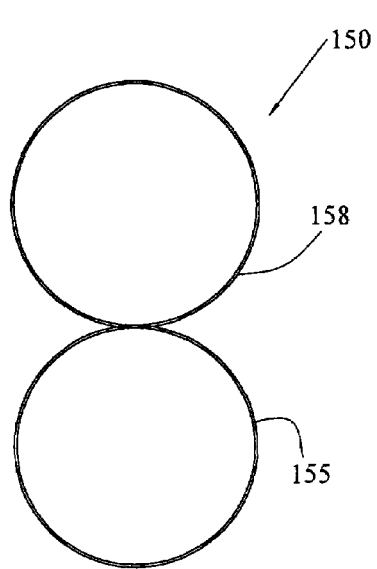
FIGS. 50-53 show several configurations of the multi-lumen sleeves in FIGS. 46-49 with their secondary lumens distended.
Figure 52:
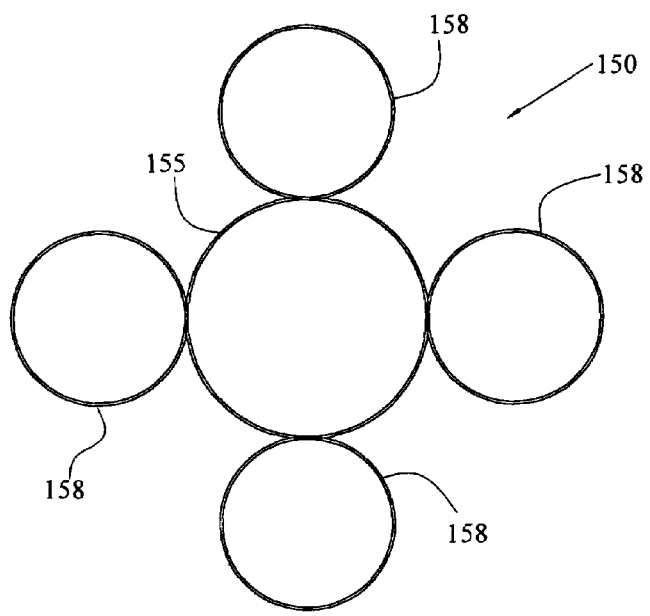
Figure 51:
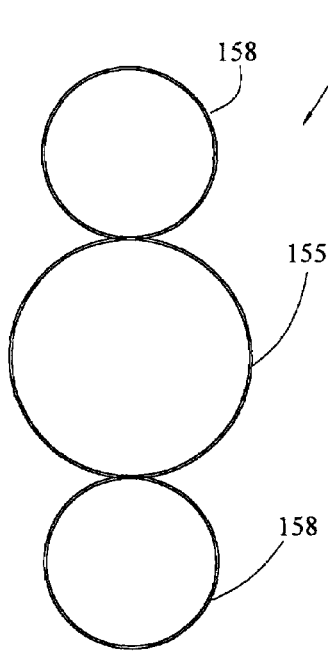
Figure 53:
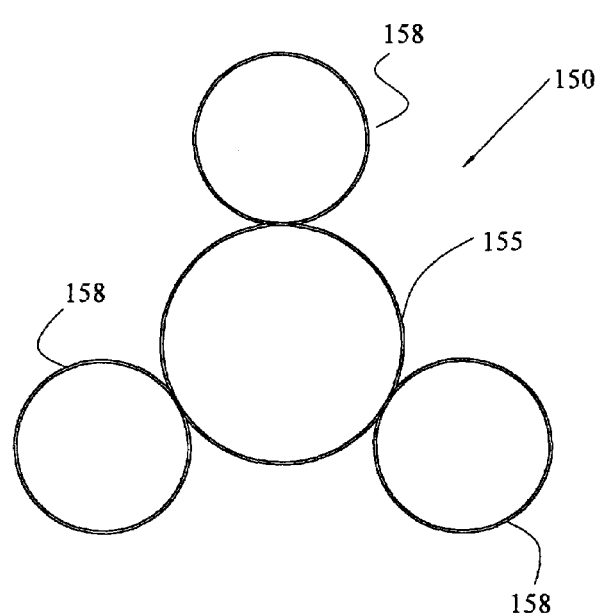

FIG. 45 shows an isometric view of the distal end 152 of the insertion shaft of an endoscope positioned in a primary lumen 155 of a multi-lumen sleeve 150. The sleeve 150 has a primary lumen 155 and at least one secondary lumen 158. Both the distal end and the proximal ends of the sleeve may be open.

The distal end 152 of the insertion shaft of the endoscope includes a working channel 154, and at least one auxiliary element 157, such as optics, illumination, irrigation etc. In FIG. 45, three such auxiliary elements 157A-157C are present, but more or fewer auxiliary elements may be present in other embodiments.

When inserting the sleeve-encased endoscope into a patient, the secondary lumens 158 typically but without being limiting, are collapsed. Keeping the secondary lumens collapsed allows for a smaller profile as the endoscope is inserted into a body cavity, wending its way toward a lesion. One method of keeping the secondary lumens collapsed and substantially adjacent to the primary lumen 155 is by using bands 160, typically, but without intending to be limiting, bands made of silicone.

The multi-lumen sleeve 150 can be made of any of many different types of flexible plastics. Without intending to limit the choice of flexible plastics or elastomers, these may include polyethylene, polyurethane, polyvinyl chloride and almost any other medical grade plastic.

Secondary lumens 158 may be formed using any of several known methods for working sheet plastics; most typically the secondary lumens 158 are formed integrally with the primary lumen. The secondary lumens can be kept collapsed by directly extruding the multi-lumen sleeve with the secondary lumens in their collapsed positions. Secondary lumen(s) may also be attached to a primary lumen using one of many techniques known to those skilled in the art such as by using a suitable medical grade glue or solvent, by employing soldering, by heat treatment, or by using high frequency welding.

When using high frequency plastic welding, the secondary lumens, in their collapsed shape, are welded directly to the primary lumen. High frequency plastic welding, also known as floating welding, may be used to gently weld multiple single secondary lumens to the primary lumen producing sleeve shapes shown in FIGS. 46-49. The sleeve can also be welded from a single plastic sheet, after first doubling back the sleeve one or more times so that portions of the sleeve are positioned to be adjacent to each other.

FIGS. 46-53 show various configurations of multi-lumen sleeves 150 usable with the present invention. As noted above, the secondary lumens 158 may be integrally formed with the primary lumen 155 by extrusion or by any of a number of plastic sheet processing techniques, such as by hot welding or high frequency (HF) welding or solvent gluing. The attachment should be effected so that it allows expansion of the secondary lumen(s) 158 when surgical instruments pass through them. The number of secondary lumens 158 is different in each of the configurations shown and the secondary lumens 158 are shown in their collapsed state (FIGS. 46-49). FIGS. 50-53 show various configurations of integrally formed multi-lumen sleeves 150 with the number of secondary lumens 158 different in each configuration. In FIGS. 50-53 the secondary lumens 158 are distended as is the case when surgical working tools are positioned inside them.

While in the embodiments described above the primary lumen is continuous, in other embodiments it need not be. In these other embodiments, the primary lumen may include holes, be net-like, etc.

Figure 54:
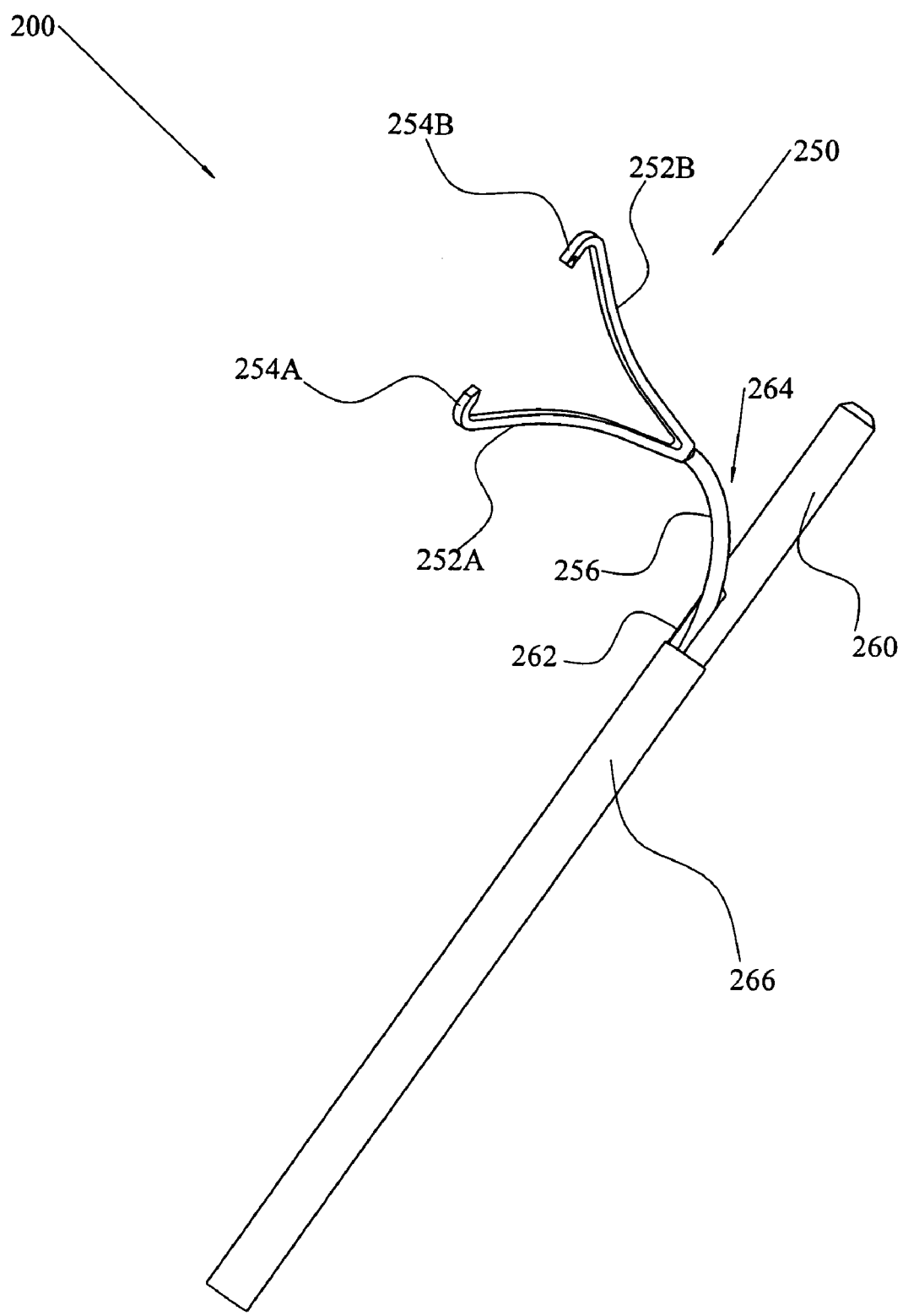
FIG. 54 shows a grasper assembly constructed according to one embodiment of the present invention, the assembly being in its open position.
Figure 55:
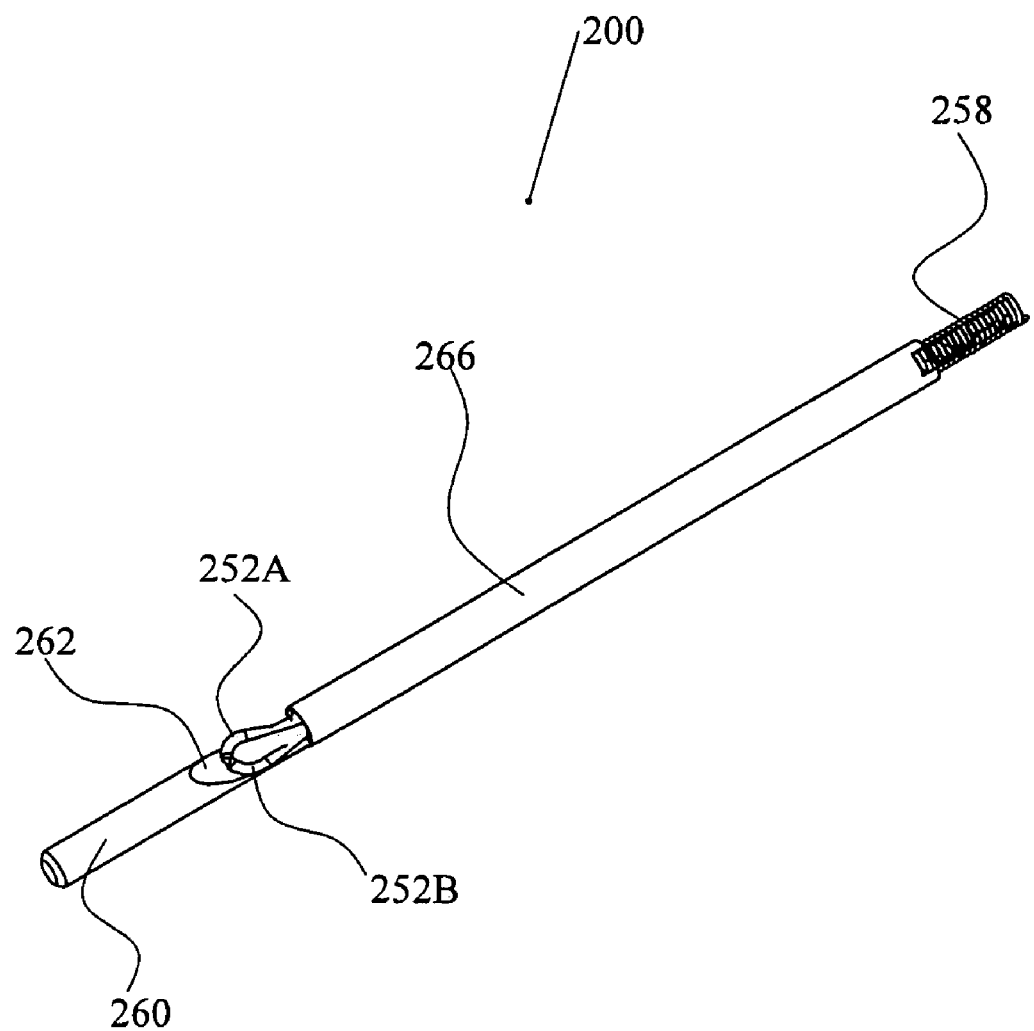
FIG. 55 shows a grasper assembly constructed according to another embodiment and in its closed position.
Figure 56:
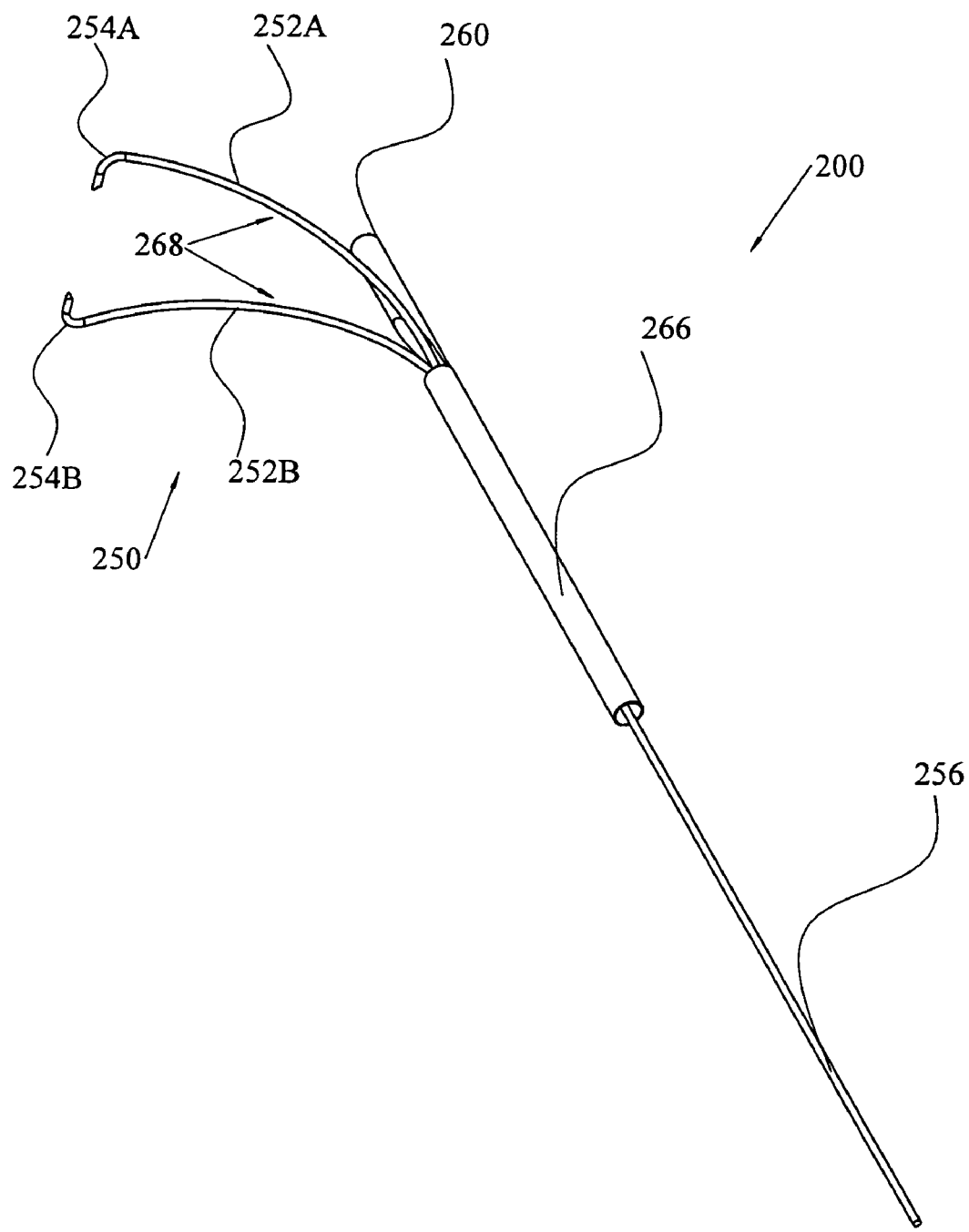
FIG. 56 shows additional details of the grasper assembly in FIG. 55 in its partially opened position.

Reference is now made to FIGS. 54-56 wherein a grasper assembly 200 constructed according to the present invention is shown.

FIG. 54 shows the grasper assembly 200 in its open position. The assembly includes a grasper 250, a grasper transporting element 260, and a spring (not shown) situated within a spring cover 266. Grasper transporting element 260 has a side window 262 through which grasper 250 is ejected when grasper assembly 200 has been brought proximate to the tissue to be resected. Grasper transporting element 260 may be made of Ni—Ti alloys or other alloys; in some embodiments it may be made of plastic.

Grasper 250 is made up of forceps arms 252A and 252B joined to a cable 256, the cable passing through the spring (not shown) in spring cover 266. Forceps arms 252A and 252B have at their ends forceps tips, 254A and 254B, respectively. These tips can take different shapes, e.g. tooth-shaped, ball-shaped, etc. In FIG. 54, cable 256 has a bend 264 or curve in it. In other embodiments, the bend is situated in forceps arms 252A and 252B. See for example bend 268 in FIG. 56.

Cable 256 should be made of a torsion resistant material such as, but not limited to, Ni—Ti alloys, while forceps arms 252A and 252B may also be made of Ni—Ti alloys. A superelastic and/or shape memory material is preferred because the cable and forceps need to straighten when they are pulled into the grasper transporting element prior to insertion. Similarly, they are also needed to straighten when pulling the grasped tissue into an opened surgical compression clip and rotating it over and around grasper transporting element 260. Since cable 256 must be rotated, a torsion resistant cable, such as a Ni—Ti cable is important. Ni—Ti alloys typically provide better twist resistance since they possess significant torsional stability. Additionally, Ni—Ti alloys have high elasticity which makes it easier to straighten curves with large radii of curvature. This is the situation when keeping the bent forceps or bent cable inside grasper transporting element 260.

While the above has been discussed in terms of Ni—Ti alloys, it is readily apparent to one skilled in the art that other shape-memory materials having properties similar to Ni—Ti alloys may be used as well.

Turning to FIG. 55, grasper assembly 200 is shown in its closed position with grasper 250 and forceps arms 252A and 252B positioned and lying inside grasper transporting element 260. Grasper 250 is partially visible through window 262. Grasper 250 remains in its encased closed position while grasper assembly 200 is advanced through a working channel of the endoscope or through a secondary lumen of a multi-lumen sleeve such as those discussed previously. Spring 258 is visible in this Figure.

FIG. 56 shows an additional view of grasper assembly 200 again with bend 268 in forceps arms 252A and 252B and not in cable 256 as in FIG. 54. Bends are required because grasper 250 must move through the clip to grasp and pull a polyp. A distance must be traversed which depends inter alia on whether grasper assembly 200 has been advanced to the polyp through a working channel of the endoscope or through a secondary lumen of the multi-lumen sleeve. This secondary lumen may be the same lumen as the one through which a clip and clip applier has been advanced or a different secondary lumen. A bend in the forceps arms is more advantageous then a bend in the cable. A bend in the forceps arms is more compact; in such a case, the length of metal that needs to be pushed out of, or pulled back into, the grasper transporting element 260 is shorter than the equivalent length of metal when the bend is in the cable. In the former case, the bend exists only in the forceps arms while in the latter case both the forceps arms as well as the bend in the wire must be pushed out of, or pulled back into, the grasper transporting element 260.

Grasper assembly 200 is activated by an actuator (not shown) situated outside the proximal end of the endoscope (see for example element 308 in FIG. 1A). The actuator is in communication with grasper 250 through cable 256, the latter an operating cable. The actuator may be of any of many types known to those skilled in the art of endoscopy. The actuator typically includes a stopper to prevent forceps arms 252A and 252B which are grasping the pulled tissue from fully retracting into window 262. By fully retracting forceps arms 252A and 252B with the grasped tissue into window 262, there would be a chance that the tissue would fully disengage from forceps arms 252A and 252B and be left behind in the body cavity.

In another embodiment of grasper assembly 200, the assembly can include a plastic tube instead of a spring and spring cover 266. The tube should be flexible enough to be inserted into the GI tract through an endoscope's working channel or through one of the secondary lumens of a multi-lumen sleeve. The plastic tube needs to have relatively good resistance to torsion.

In this last embodiment, the plastic tube can be extended to include an integrally formed grasper transporting element 260 obviating the need for a separate grasper transporting element 260. A side window 262 can be formed in the plastic tube. In this embodiment, therefore, the grasper assembly includes two elements, grasper 250 and a plastic tube with a side window 262 close to its distal end.

A method for effecting full transmural resection is contemplated as part of the present invention and is illustrated in FIGS. 57-74B to which reference is now made.

Figure 57:
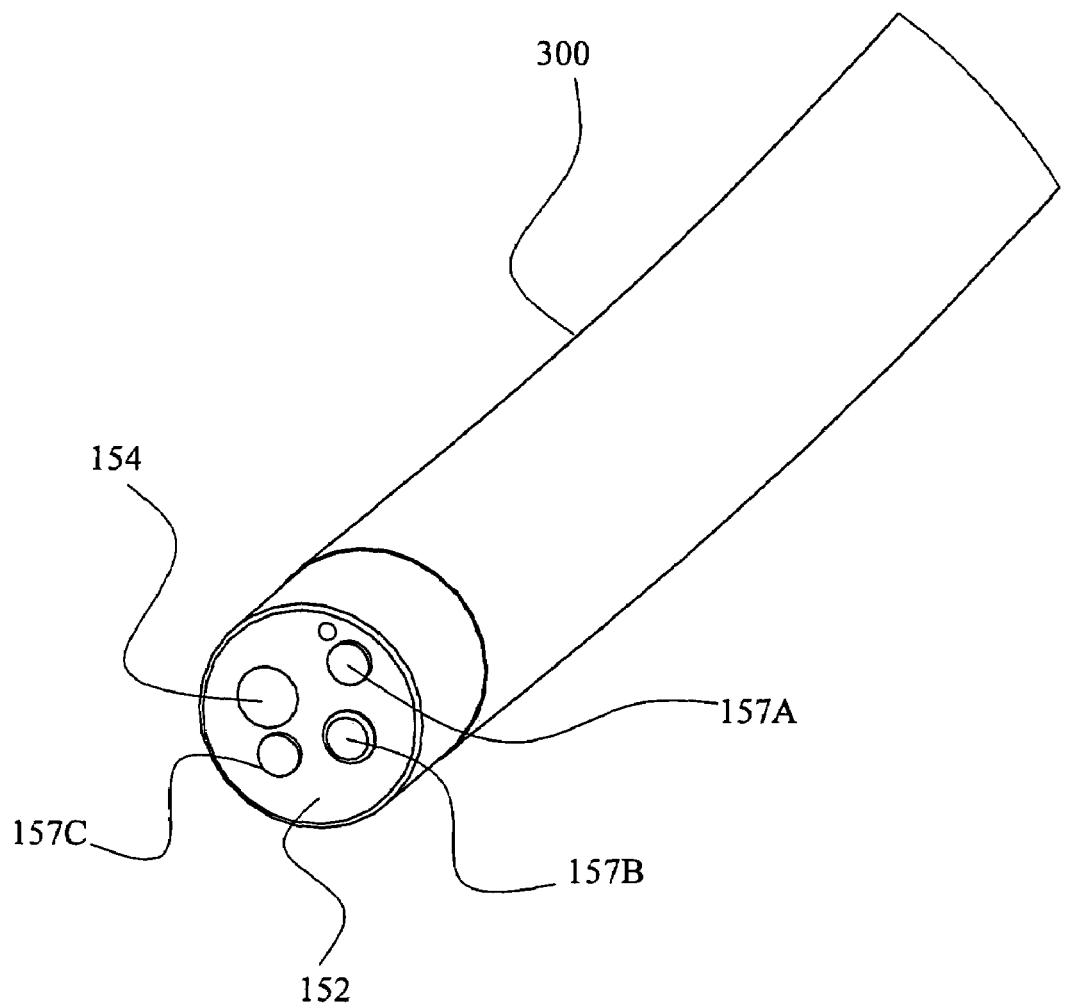
FIG. 57 shows an endoscope prior to insertion into a multi-lumen sleeve.
Figure 58:
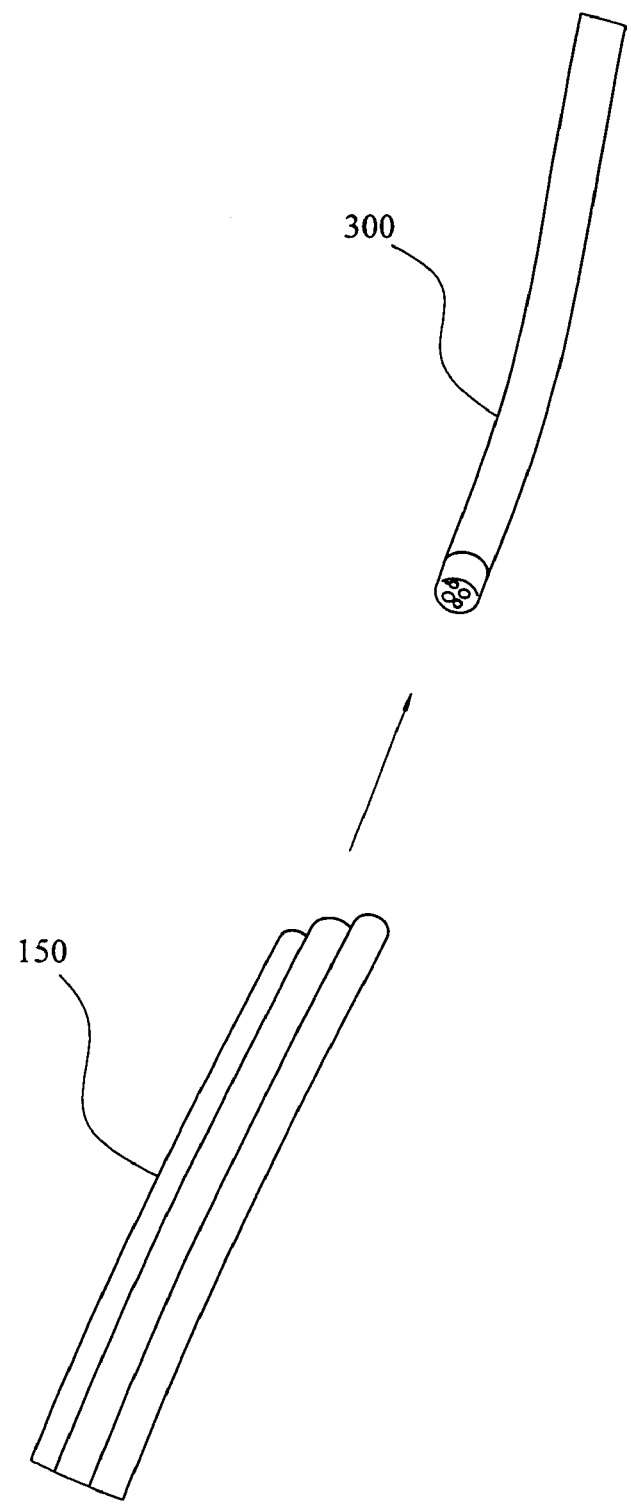
FIG. 58 shows the endoscope of FIG. 57 being inserted into a multi-lumen sleeve.
Figures 59A, 59B:
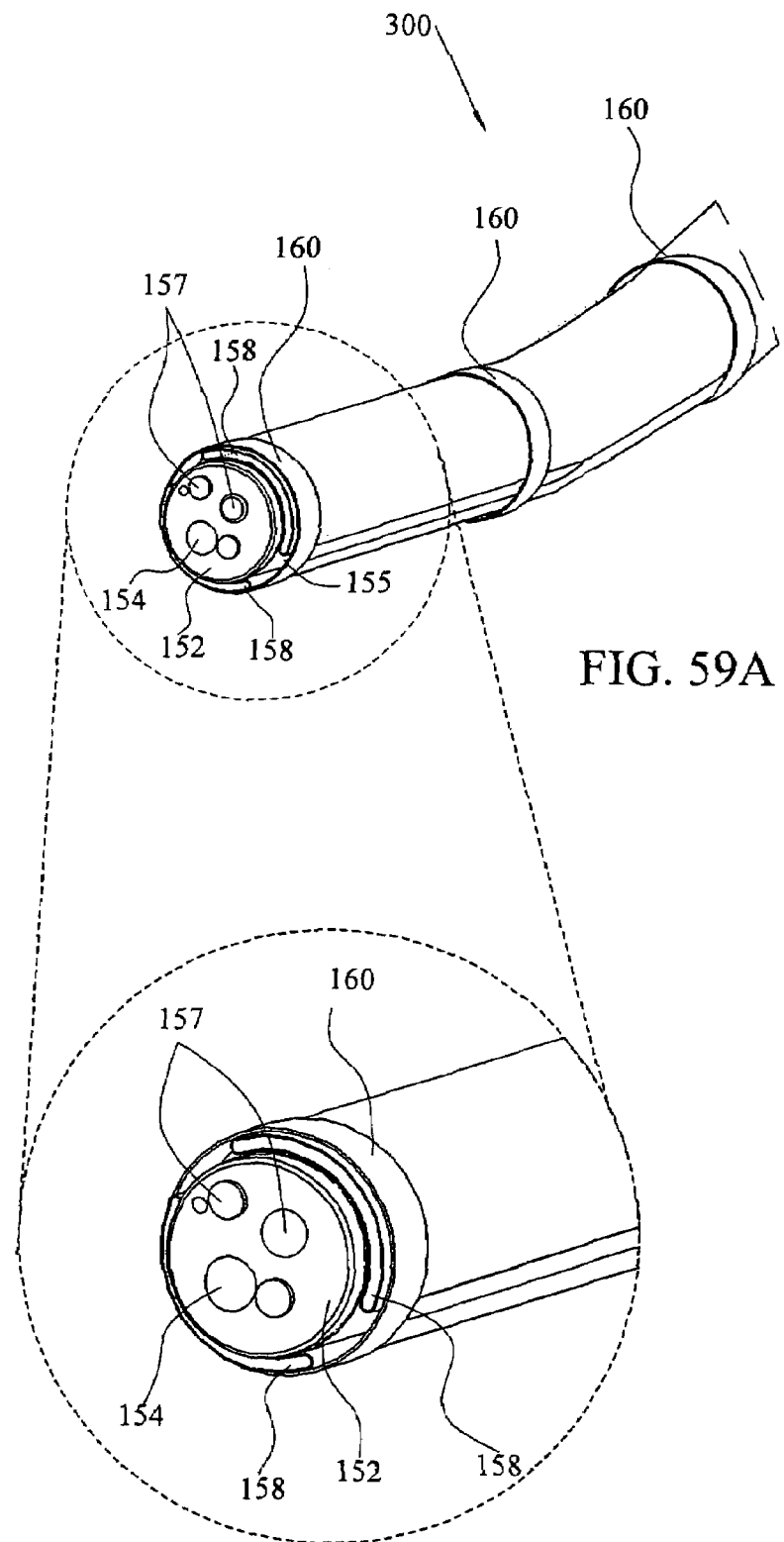
FIG. 59A shows the endoscope after insertion into the multi-lumen sleeve.
FIG. 59B shows an enlarged view of the distal end of the endoscope in FIG. 59A.

FIG. 57 shows an endoscope insertion shaft 300 with a working channel 154. It also contains several auxiliary elements, here three, denoted as 157A-157C. The number of working and auxiliary channels may be more or less in other embodiments of shaft 300. A multi-lumen plastic sleeve 150 is brought to and over endoscope insertion shaft 300 (FIG. 58). The endoscope insertion shaft 300 is encased in the primary lumen 155 of the multi-lumen sleeve 150 and the one or more secondary lumens 158 of sleeve 150 are typically collapsed and, if needed, held by bands 160 (FIG. 59A). The bands 160 are expandable when working instruments are inserted into the collapsed secondary lumens 158. Insertion of these instruments occurs after the distal end 152 of the endoscope shaft 300 is positioned proximate to the suspect lesion. Bands may not be required in some embodiments, if the secondary lumens 158 remain collapsed by themselves while the encased endoscope insertion shaft 300 (FIG. 59A) is inserted into a body organ or if not required by the physician. It is to be understood that means or methods other than bands may be used to ensure that the secondary lumens remain collapsed while the encased endoscope shaft is inserted into the body and positioned near the suspect lesion.

Figure 60:
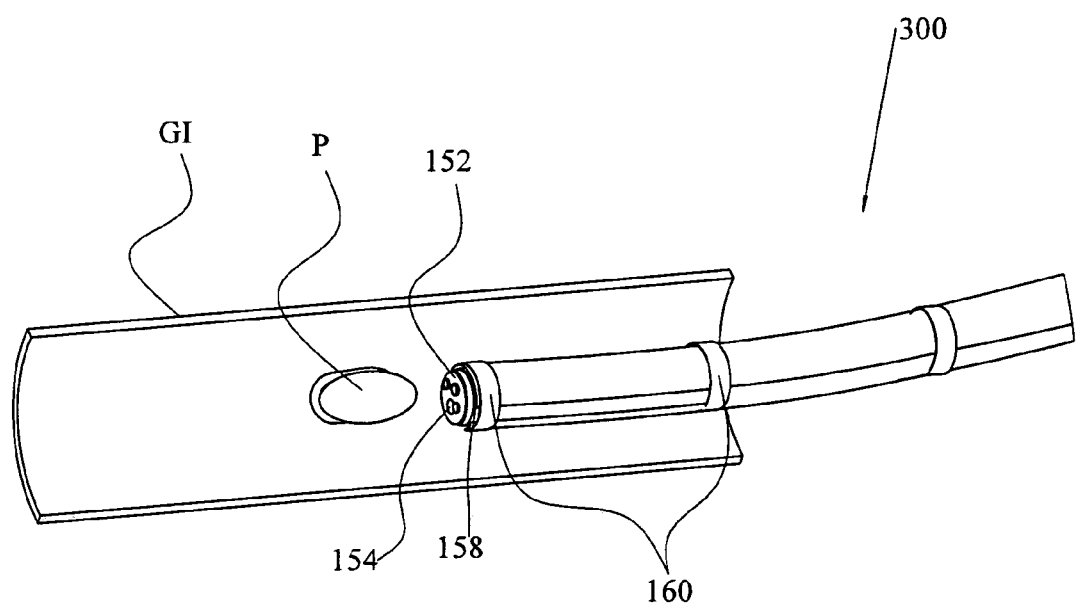
FIG. 60 shows the sleeve-encased endoscope as it approaches a polyp in the gastrointestinal tract.

The encased endoscope insertion shaft 300 is advanced within the body lumen until it is near the lesion, herein taken to be a polyp P in the gastrointestinal (GI) tract. (FIG. 60).

Figure 61:
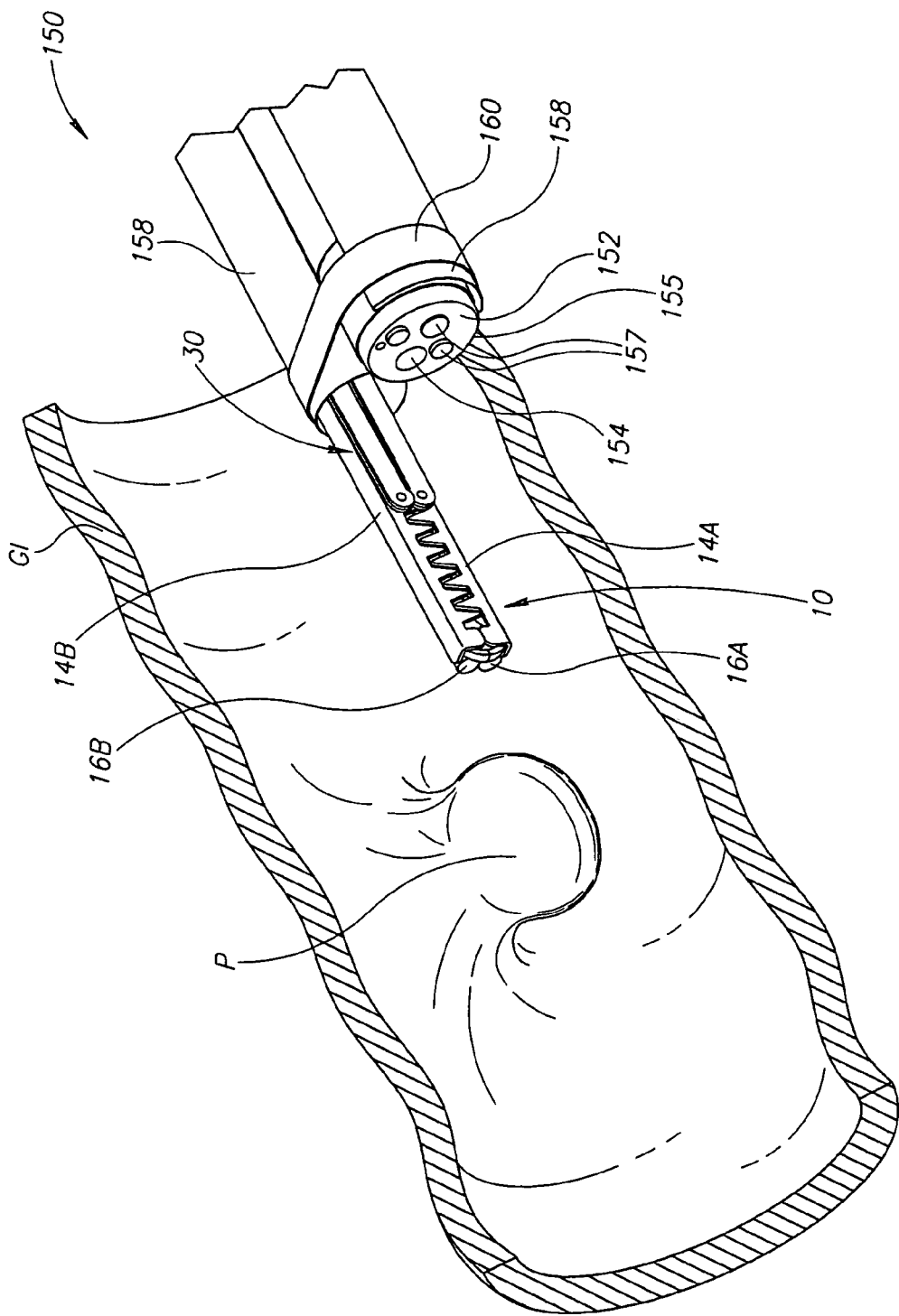
FIG. 61 shows a view of a surgical clip attached to an applier being advanced to the site of the polyp through a secondary lumen of the sleeve.

At that point a surgical compression clip 10, and its attached applier 30, both in their closed positions, are advanced through a secondary lumen 158 of the sleeve 150 to polyp P. Clip 10 exits the secondary lumen 158 still in its closed position (FIG. 61).

Figure 62:
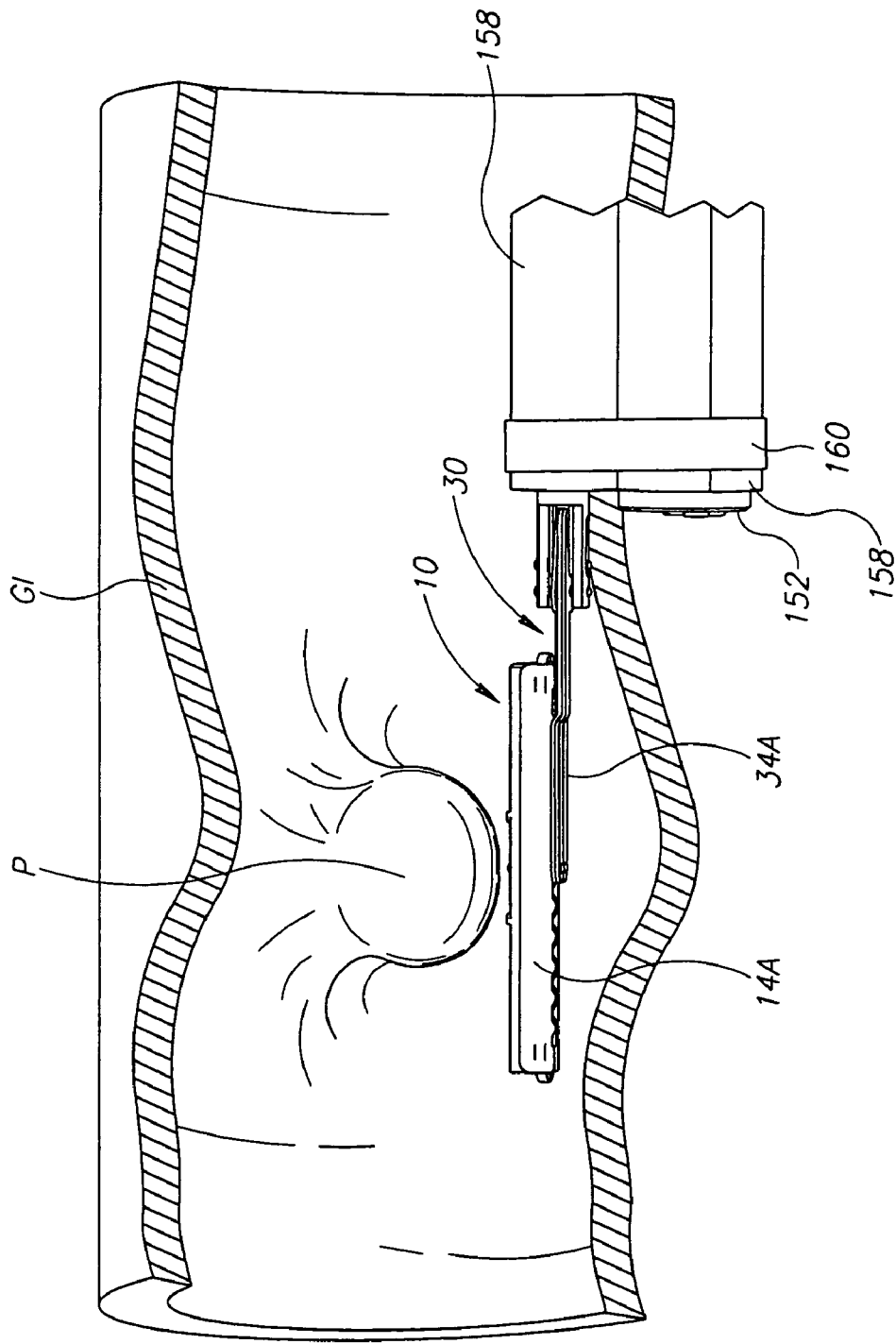
FIG. 62 shows a top side view of the surgical clip attached to an applier being positioned proximate to the polyp.

Clip 10, still in its closed position, is brought to its final position adjacent to polyp P (FIG. 62).

Figure 63:
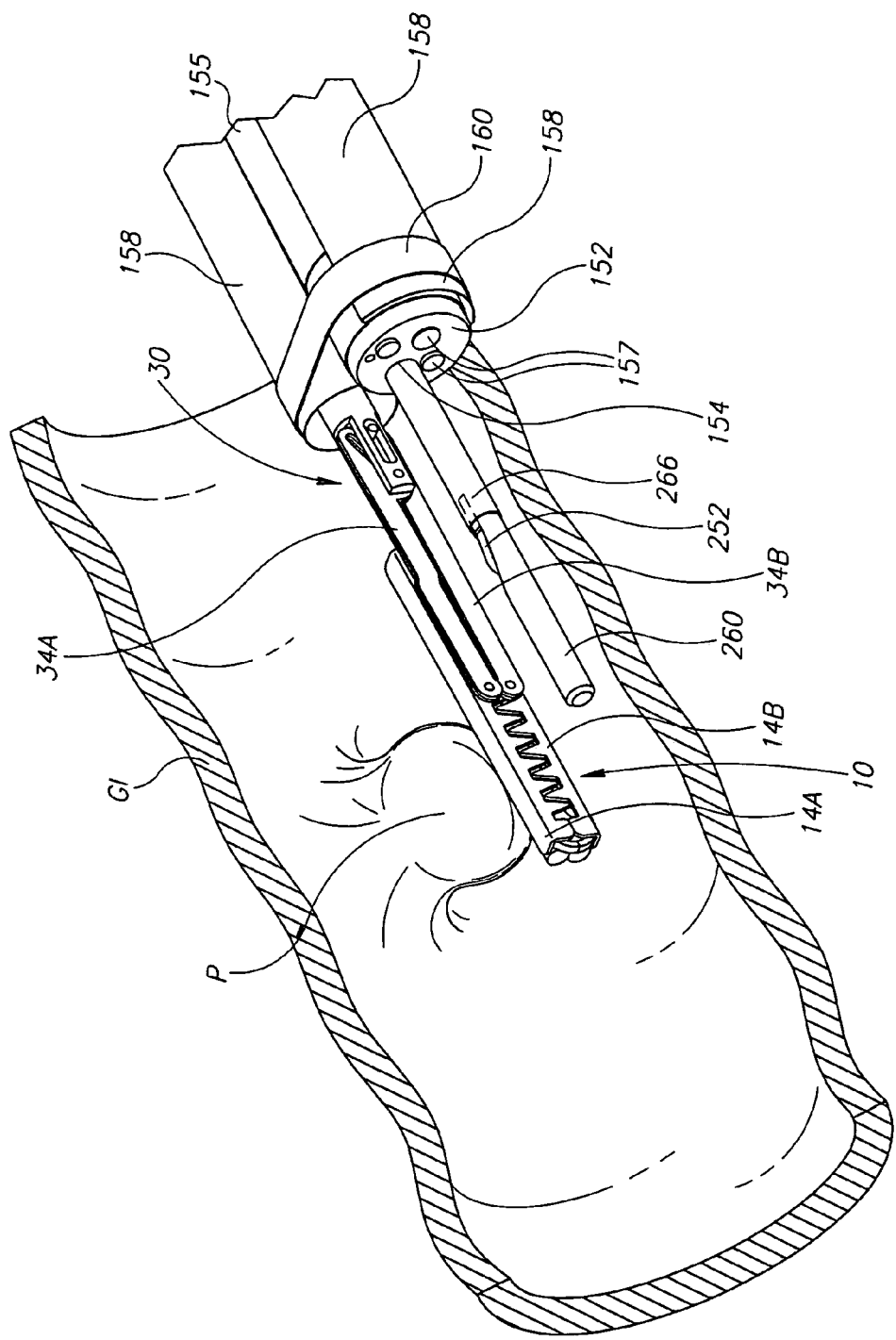
FIG. 63 shows a top side view of a surgical clip and applier positioned proximate to a polyp and a grasper assembly being positioned proximate to the polyp after advancing through a working channel of the endoscope.

A grasper assembly is then inserted into a working channel 154 of the endoscope insertion shaft 300, advanced through the shaft, and then advanced out of the distal end 152 of endoscope insertion shaft 300 to the region adjacent to polyp P (FIG. 63).

In other embodiments, the grasper assembly, i.e. grasper (not shown) and grasper transporting element 260, is introduced via a secondary lumen 158 of the multi-lumen sleeve 150 and not through a working channel 154 of the endoscope shaft. From an operational point of view, this has no significant effect on the method described.

In yet another embodiment, the grasper assembly, clip 10 and clip applier 30 may be advanced through the same secondary lumen 158 from the proximal end of the endoscope shaft to the suspect lesion.

In yet another embodiment, the grasper assembly may be inserted into and advanced through a second working channel of the endoscopic insertion shaft.

Figure 64:
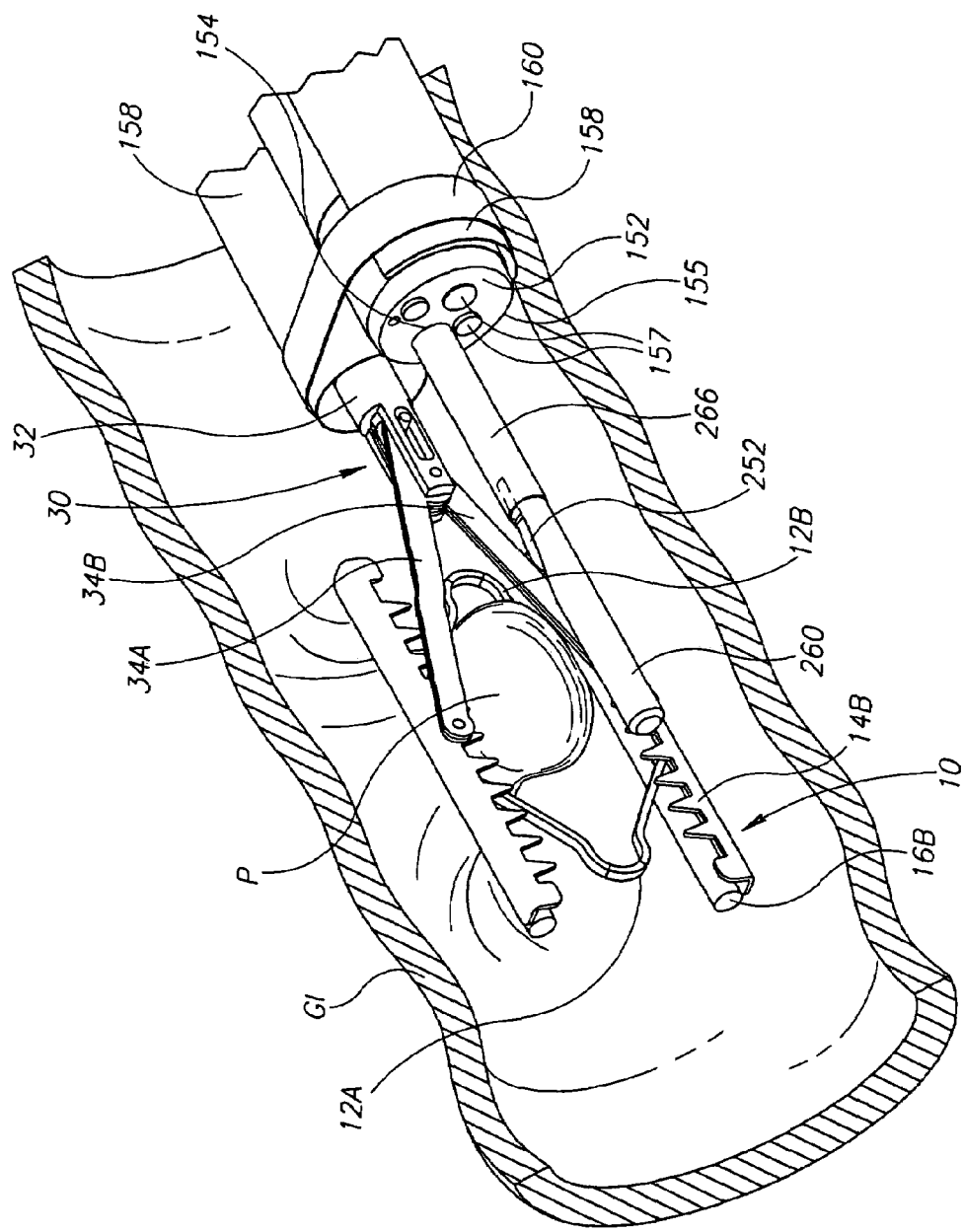
FIG. 64 shows a top side view of the opened clip proximate to the polyp.

Clip 10 is then opened by applier 30. The opened clip is positioned so as to bound polyp P so that the lesion can be pulled through the clip. FIG. 64 shows an isometric view of this step.

Figure 65:
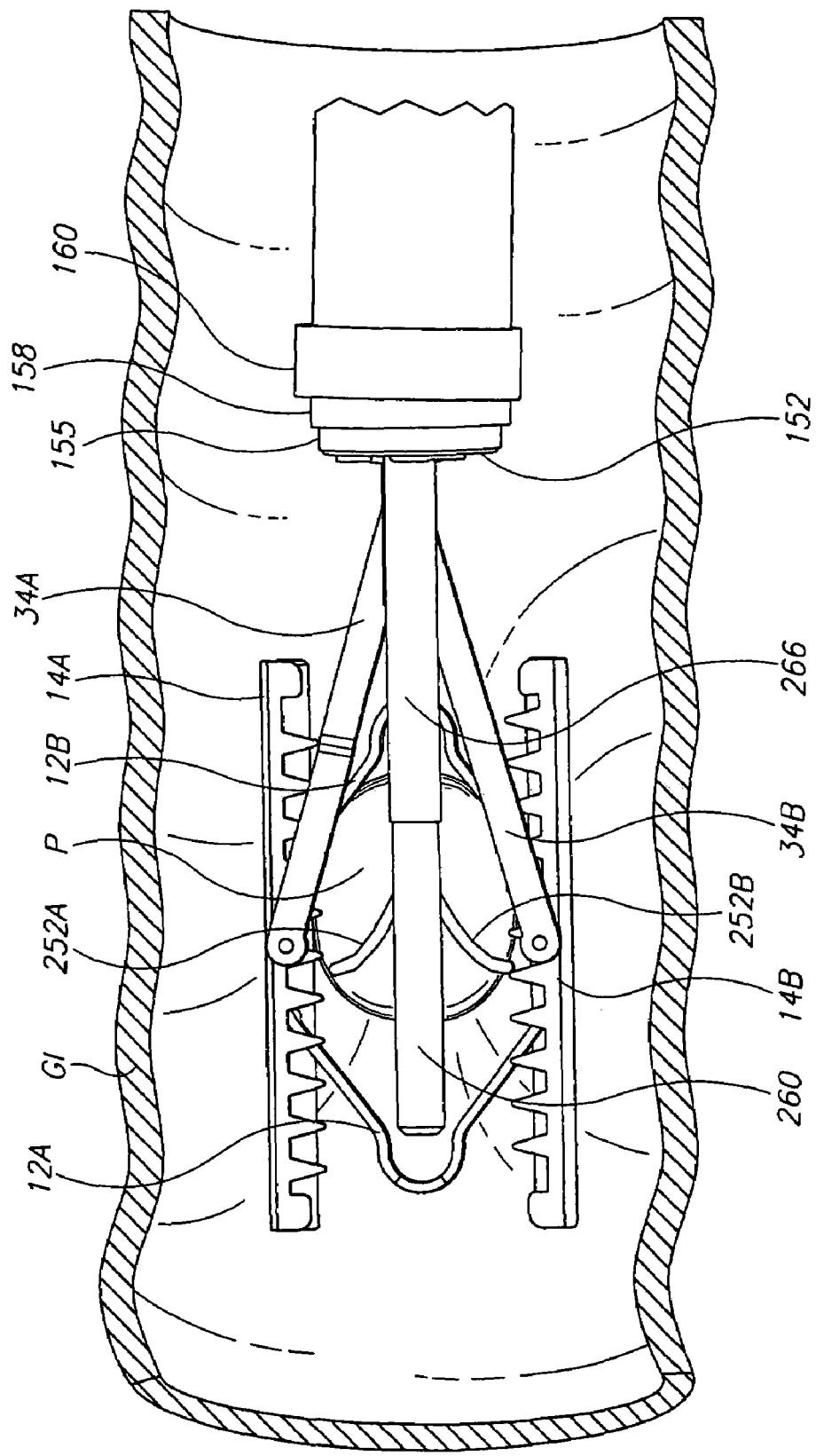
FIG. 65 shows a top view of the grasper of the grasper assembly beginning to pull the polyp through the opened clip shown in FIG. 64.
Figure 66:
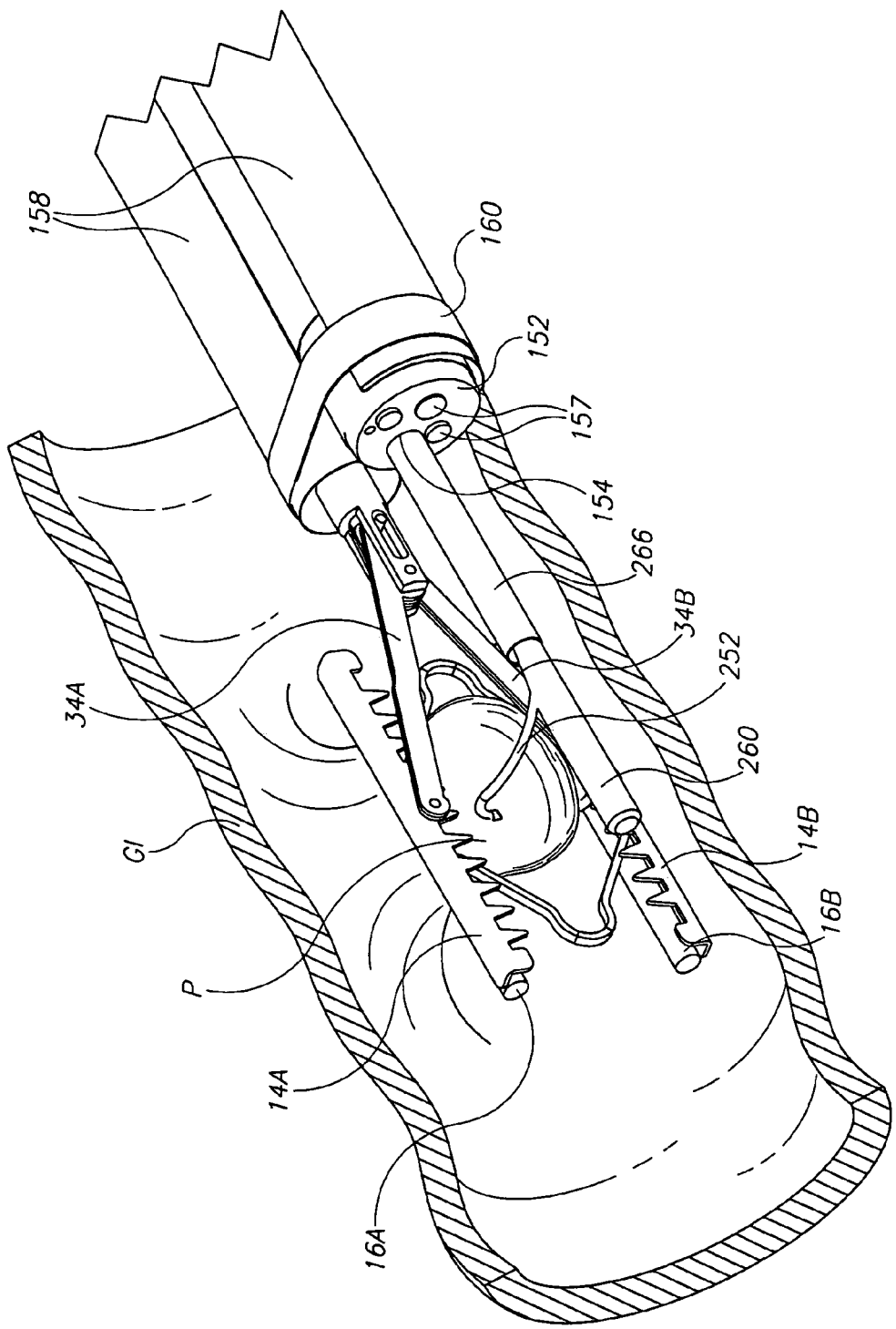
FIG. 66 shows a top side view of the grasper of the grasper assembly grasping the polyp.
Figure 67:
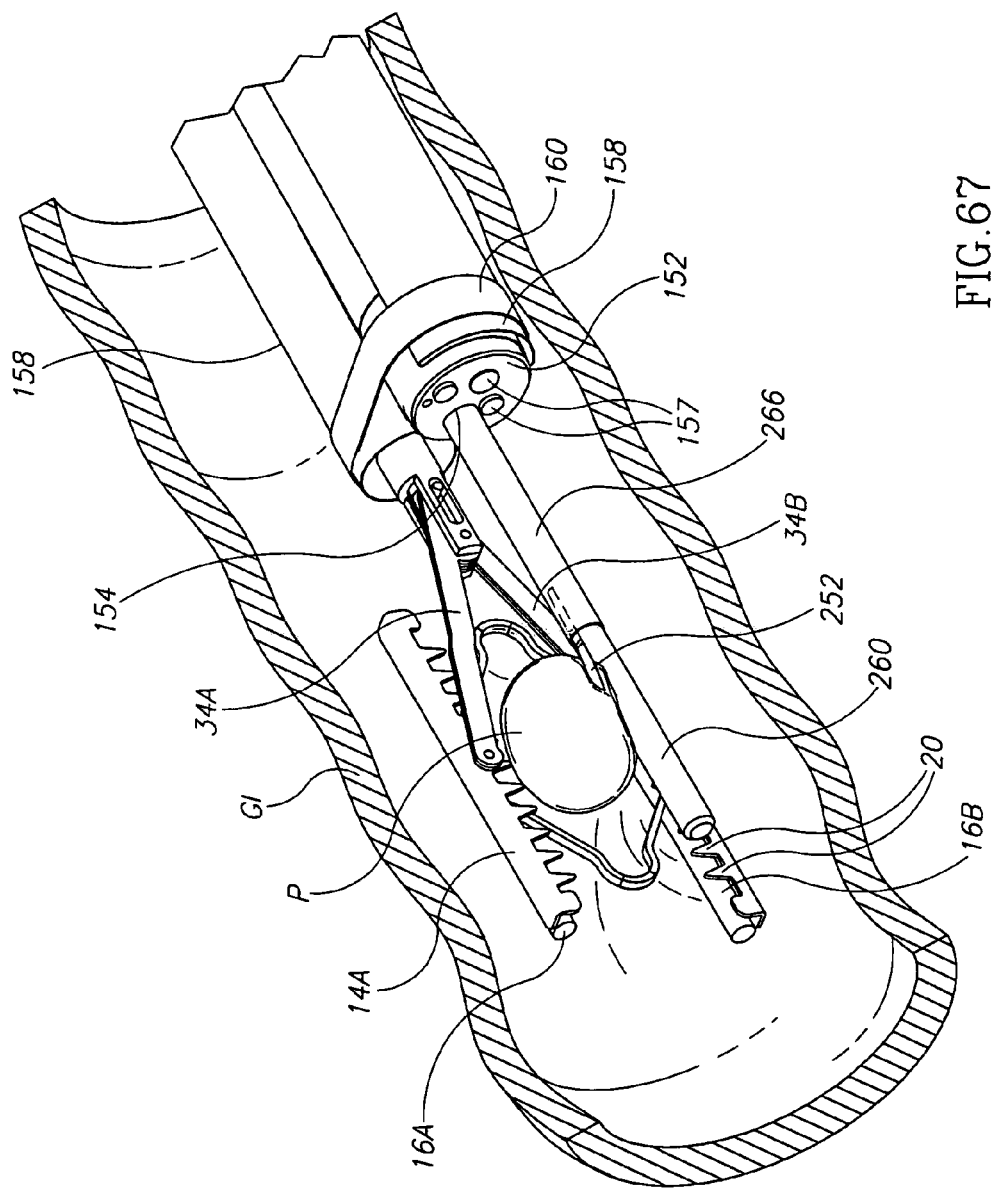
FIG. 67 shows a top side view of the grasper continuing to pull the polyp through the opened surgical clip.
Figure 68:
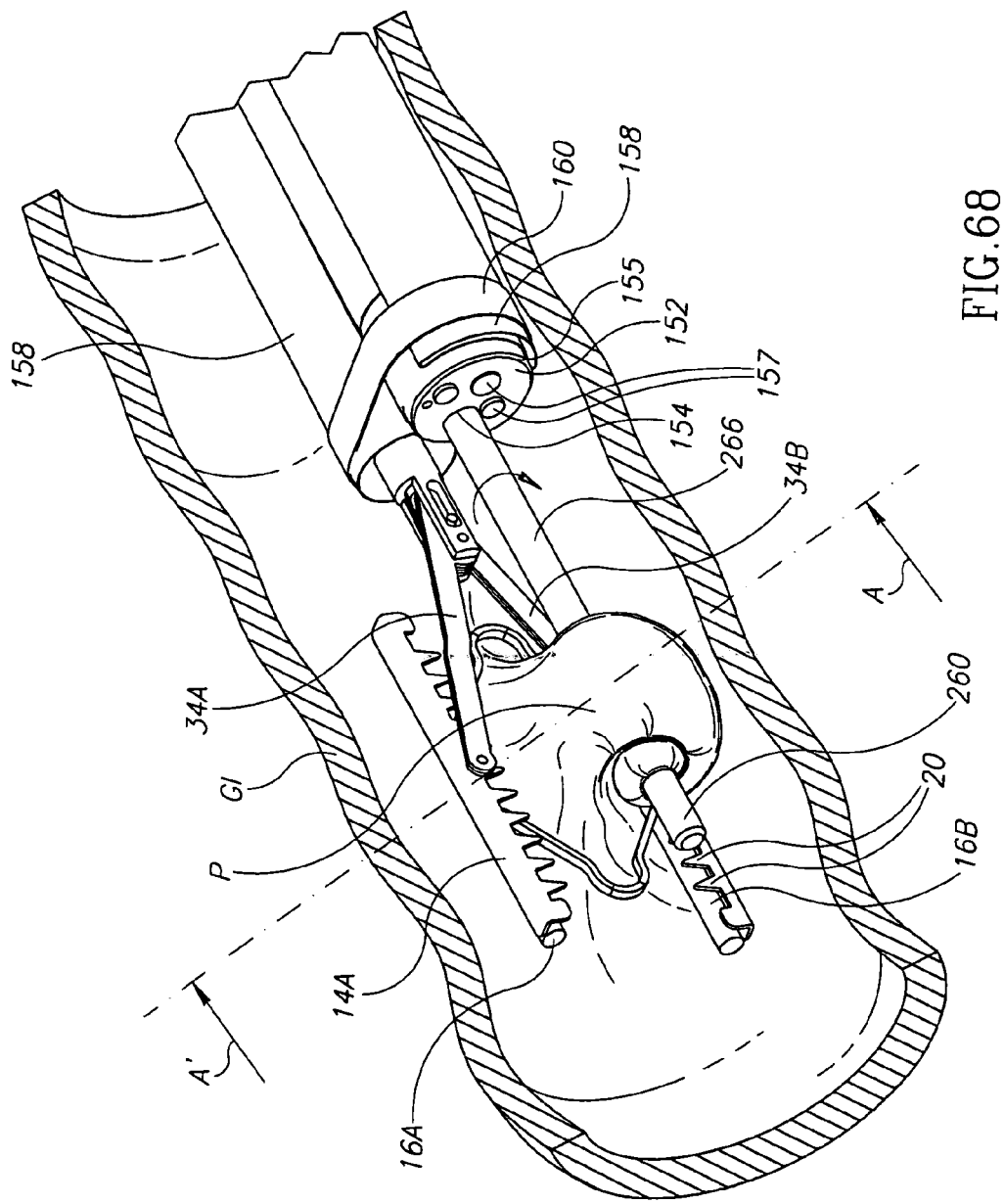
FIG. 68 shows a top side view of the grasper and grasper transporting element rotating and wrapping the pulled polyp around the grasper transporting element.
Figure 69:
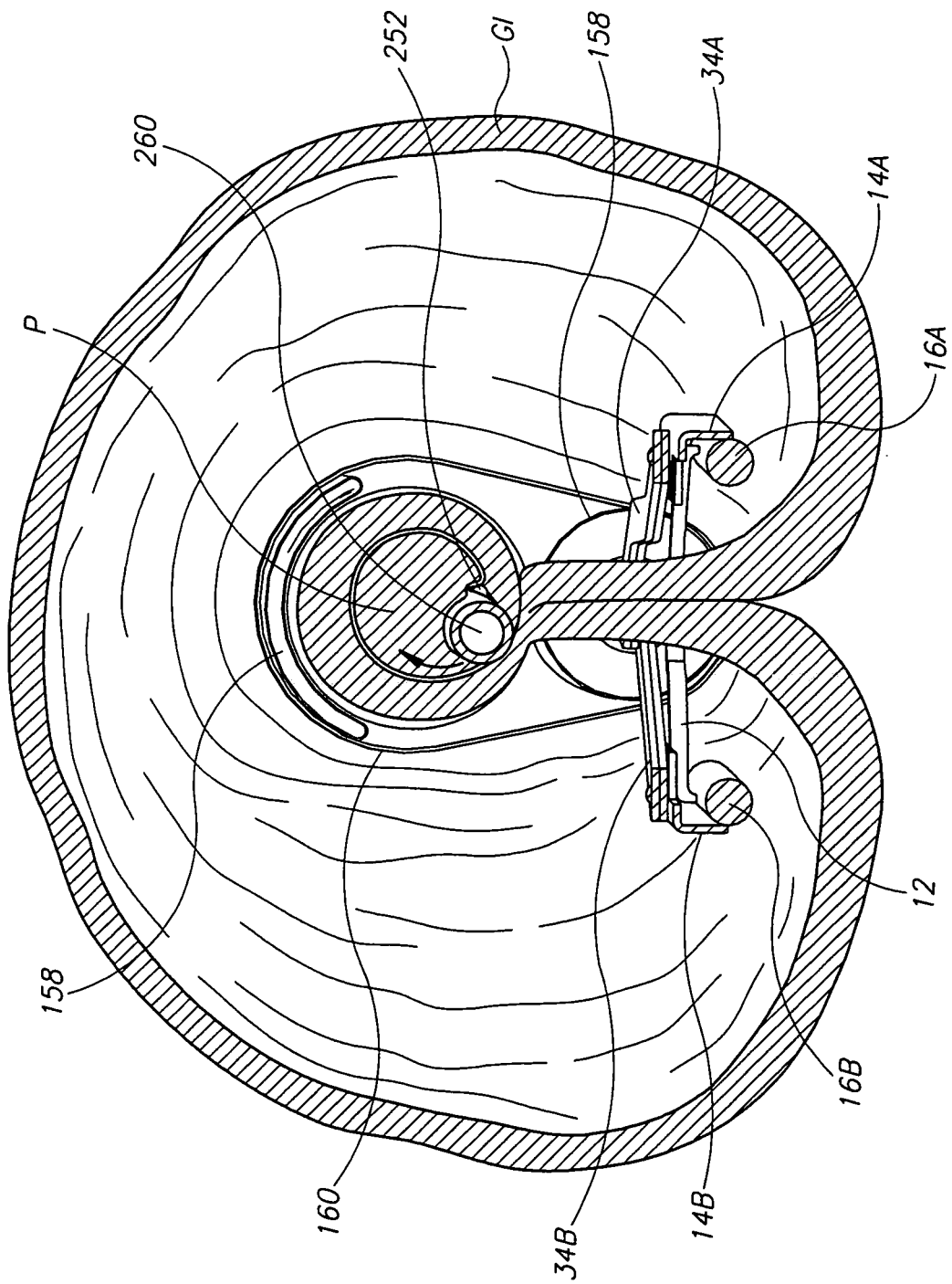
FIG. 69 shows a cross-sectional view along line AA' of FIG. 68 of the grasper and grasper transporting element rotating and wrapping the pulled polyp around the grasper transporting element.

Up to this point, the grasper (not shown) remains inside its grasper transporting element 260. Now the forceps arms 252 of the grasper are ejected from grasper transporting element 260 and positioned to grasp polyp P through the open clip (FIGS. 65 and 66).

Polyp P is then pulled by forceps arms 252 into the separated compressing and securing elements 16A, 16B and 14A, 14B, respectively, of open clip 10. This is shown in a top side view in FIG. 67. In this view, one of the forceps arms 252 of the grasper is barely visible; most of this arm and the entire second forceps arm are obscured by polyp P.

After, or simultaneously with, pulling polyp P, the polyp is rotated over and wrapped around grasper transporting element 260. This rotation is shown in an isometric view in FIG. 68 and a cross section view (FIG. 69) along line AA' of FIG. 68. Rotation is effected by the rotation of the entire grasper assembly, the grasper with forceps arms 252 holding the pulled polyp P, the grasper transporting element 260 and the assembly's shaft (not shown) using a control handle positioned outside the body cavity. Alternatively, rotating the control handle outside the body can be avoided by creating a swivel mechanism in the mechanical connection with the grasper assembly and rotating the swivel mechanism. Rotation ensures that sufficient tissue is being maneuvered into clip 10 and near severing device 310 (shown in FIG. 72) to allow for full transmural resection.

Figure 70:
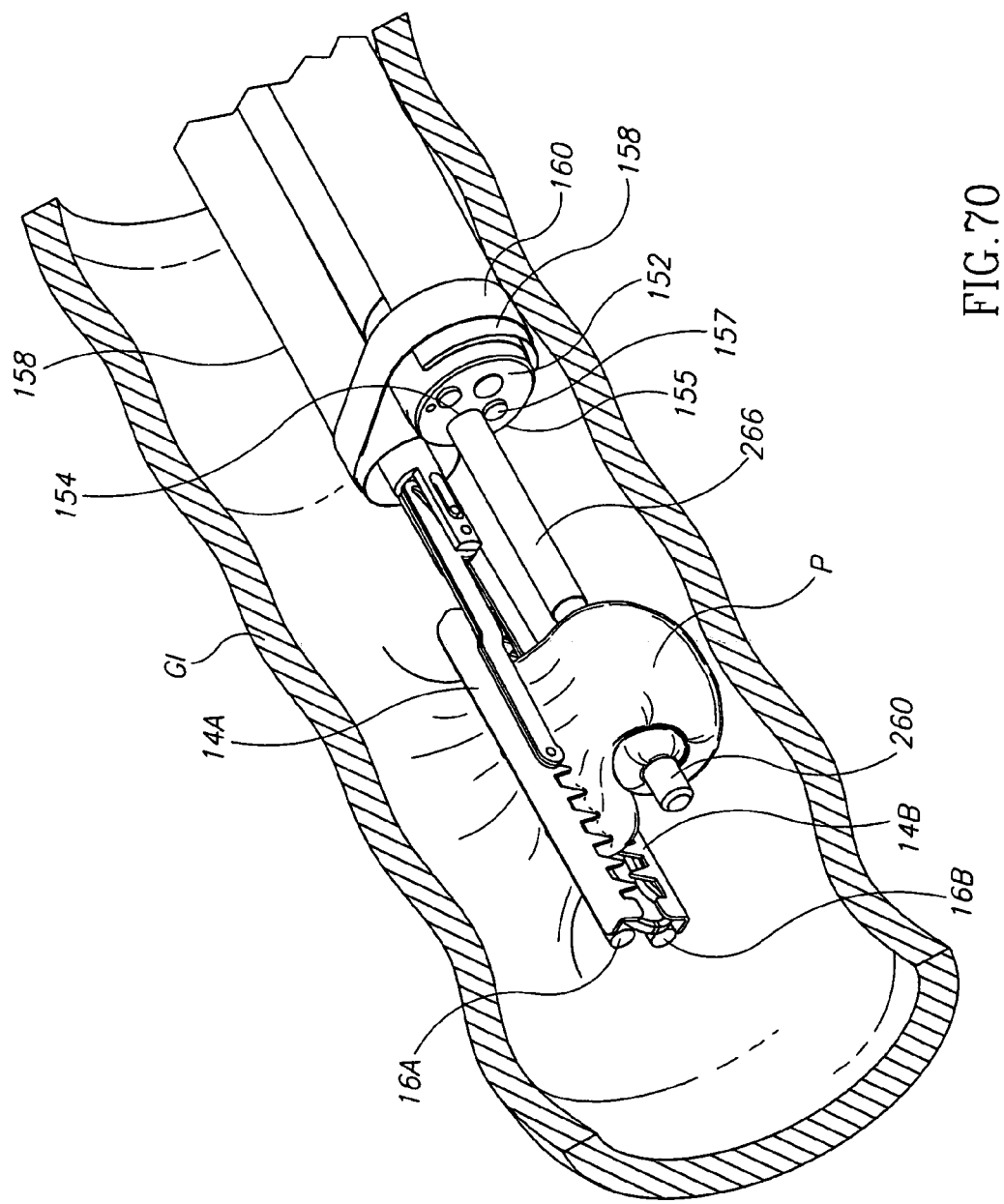
FIG. 70 shows a top side view of the surgical clip closing around the wrapped polyp.
Figure 71:
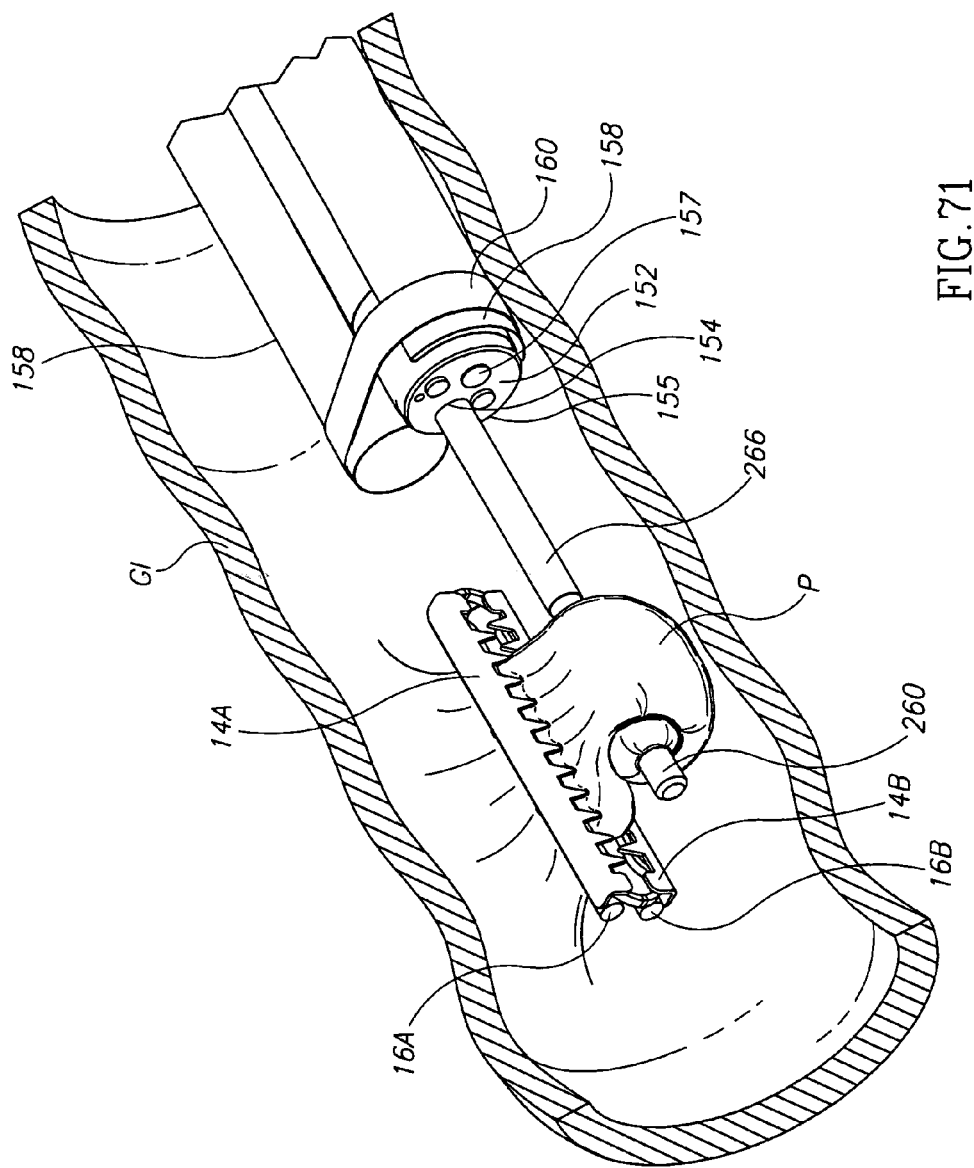
FIG. 71 shows a top side view of the closed surgical clip and polyp without the applier that has been withdrawn through a secondary lumen from the region of the resected polyp.

Clip applier 30 then closes clip 10 around the pulled and rotated polyp P (FIG. 70). Clip applier 30 is detached from the closed clip 10 and withdrawn via the secondary lumen 158 through which it entered (FIG. 71). Alternatively, if the physician feels it will assist him during the tissue resection, clip applier 30 could be detached from clip 10 after tissue resection.

Figure 72:
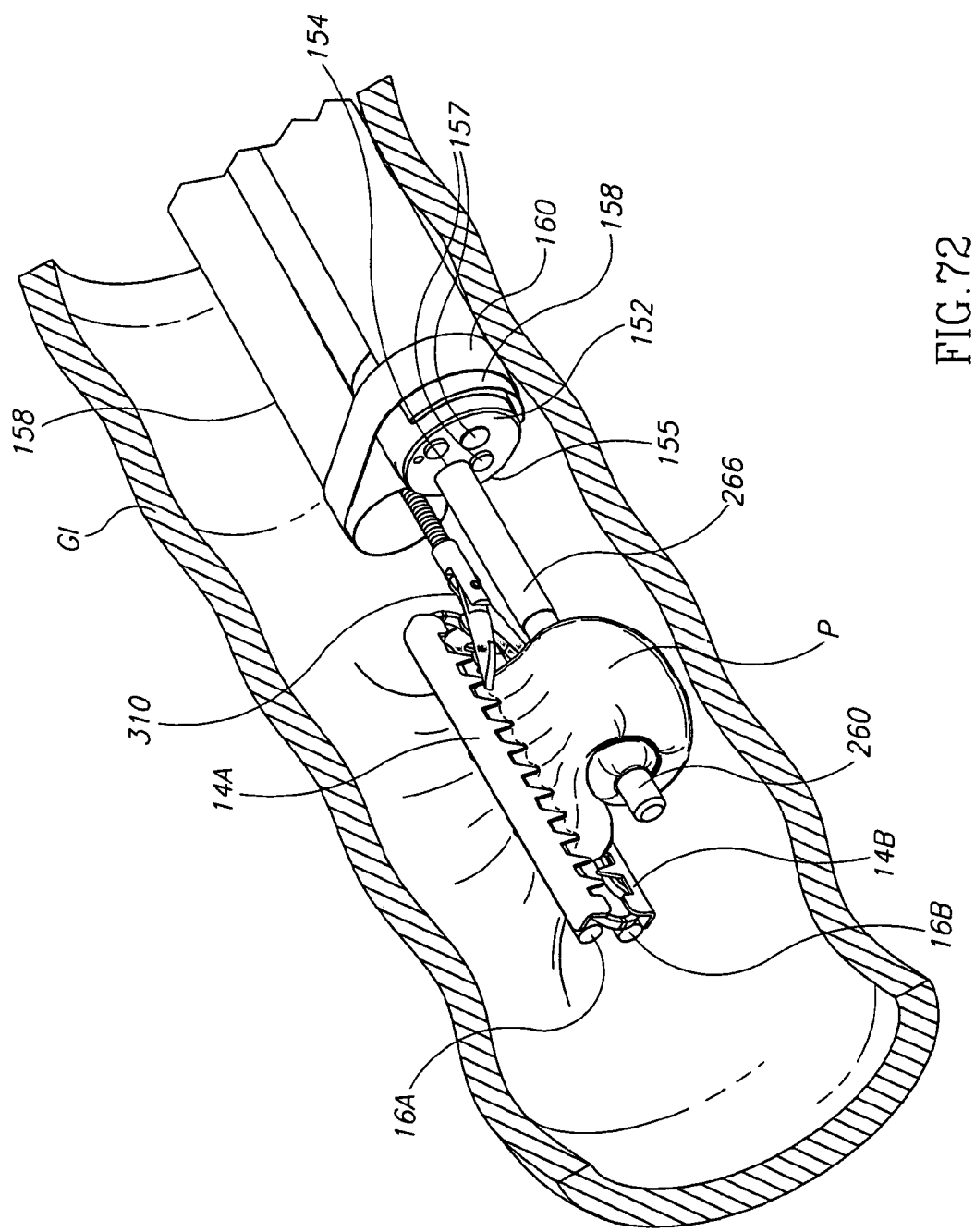
FIG. 72 shows a top side view of the closed surgical clip and polyp with a severing device approaching the rotated polyp for severing.

Polyp P wrapped around grasper transporting element 260 and compressed by clip 10 is severed by a severing device 310 shown being positioned close to polyp P (FIG. 72). Severing device 310 may be advanced to the polyp through the endoscope's working channel 154 or through a secondary lumen 158 of sleeve 150. In FIG. 72, severing device 310 has been advanced to its position for severing through the secondary lumen 158 used for advancing clip 10 and its applier 30. Severing device 310 approaches polyp P and severs it from the wall of the GI tract. The actual step of severing is not shown.

After severance of polyp P, the severed polyp held by the forceps arms of the grasper, together with the remainder of the grasper assembly, the severing device 310 and the endoscope shaft, are retracted in the direction of the proximal end of the endoscope and withdrawn from the body. Withdrawal directly from the body organ is a straight-forward step, and therefore this step of the method is not presented in a separate Figure. Polyp P can then be biopsied or treated as needed by a physician.

Figure 73:
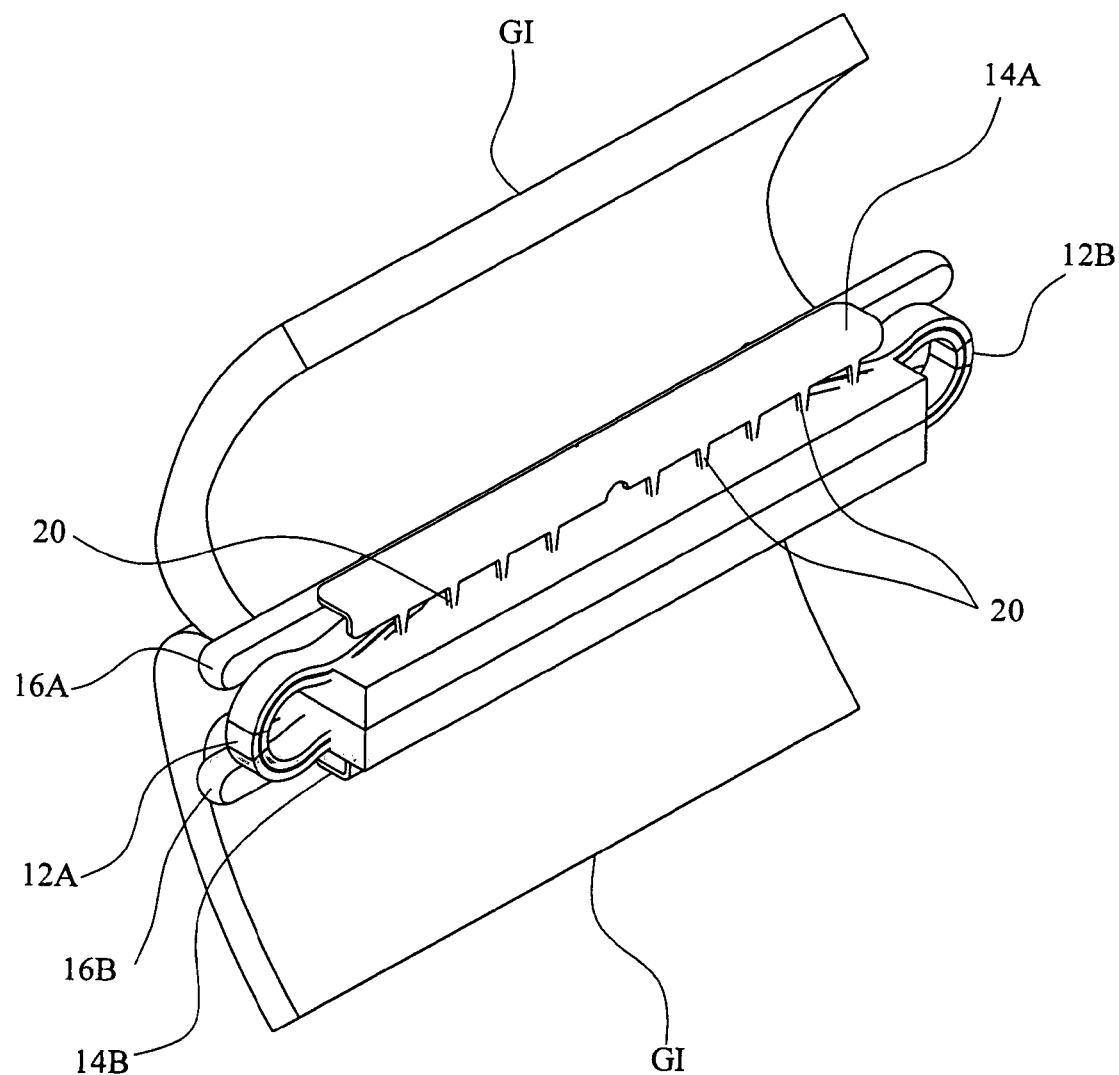
FIG. 73 shows a top side view of the tissue held by the clip at the resection site.
Figure 74A:
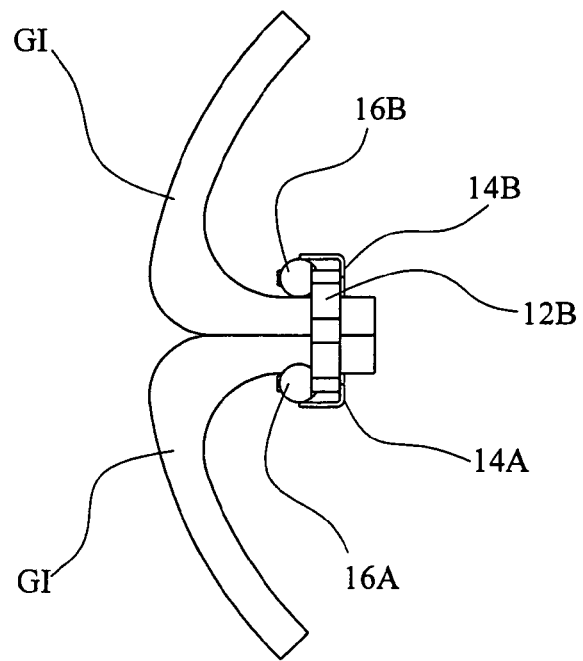
FIGS. 74A and 74B show two side views of the tissue held by the clip at the resection site.
Figure 74B:
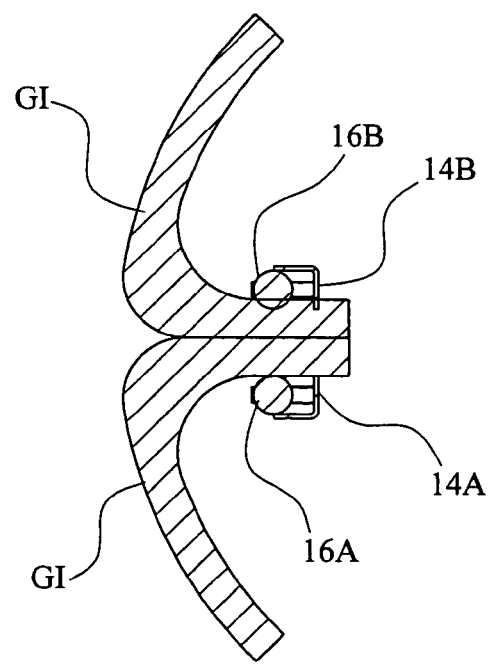

The closed surgical compression clip 10 remains around that portion of the GI wall from which the tissue was resected (FIGS. 73, 74A and 74B). Compression continues until necrosis is induced and healing of the resected site occurs. Clip 10 is naturally expelled from the body through the rectum or retrieved by the physician if needed.

The above described method may be operative when employing most of the clips designed according to embodiments of the present invention.

However, clip embodiment five discussed in conjunction with FIGS. 31A-44 requires some additional and/or modified steps. The element numbering below are those used in conjunction with FIGS. 31A-44 to which reference should be made.

The method for using the clip described in conjunction with FIGS. 31A-44 includes many of the same steps as those described above. However, the following additional or modified steps emphasize the novel aspects of the method associated with clip embodiment five. It does not include all of the steps required, many of which—including the step of rotation—can be readily understood by reviewing the method described above.

Additional or modified steps when using clip embodiment five include:

Insertion of clip 70 in its closed position together with its applier 105;

Releasing the force exerted by applier 105 allowing hinge spring 86 to spread apart arms 72 and 74 of clip 70;

Pushing wire 90 forward and extending it to form a loop;

Placing the wire 90 loop over the polyp;

Pulling the polyp with a grasper through the loop created by the extended wire;

Positioning the arms 72 and 74 of clip 70 in their open position and bringing them around the side of the polyp rather than positioning the clip from the top of the polyp as with other clips discussed in the present invention;

Alternatively, the clip may be positioned in proximity to the polyp, after which the polyp is pulled between the open clip arms using a grasper;

Pulling wire 90 taut thereby preventing the polyp from escaping from between arms 72 and 74:

Closing arms 72 and 74 by continuing to pull wire 90 and/or using applier 105, and pulling cable 102 until latch 80 snaps over the second clip arm and latches therewith;

Detaching the anchor element 97 which anchors wire 90 to arm 74; and Pressing applier 105 slightly to release the applier.

The above step of pulling the polyp with a grasper is optional since in most situations wire 90 loop by itself can be maneuvered to encompass, grasp and pull the polyp or its stalk.

Positioning the clip from the side as discussed above is a result of the polyp being encompassed by wire 90 when the latter is in its extended position. When made taut, the wire effectively pulls the polyp from a lateral position into the waiting open arms 72 and 74 of clip 70.

Generally, insertion of closed clip 70 is effected through a secondary lumen of a multi lumen sleeve, but it also may be advanced through a working channel of the endoscope. The step of applying applier 105 occurs only after clip 70 has exited the secondary lumen or working channel.

It is readily understood by one skilled in the art that a full thickness resection with wide lateral areas (margins) is very difficult to achieve using conventional surgical approaches and employing conventional surgical instruments. This is particularly true of large polyps and especially large sessile polyps. Grasping and pulling a large section of a generally slippery, polyp is very difficult especially given the limited space available in the body lumen for manipulation of the tissue. In order to overcome this difficulty, the step of rotating taught by the method of the present invention is useful. Additionally, a specially designed grasper assembly as described herein is used to effect and execute the step of rotating. Both the grasper assembly and step of rotating may be used to ensure that the entire polyp plus an adequate margin is resected.

In a previous embodiment of the tissue grasper a mechanically operated instrument was described. Typically, at least one portion of the grasper included a shape memory material. In a second embodiment of the tissue grasper, rather than using mechanical grasping of the tissue to be resected, a vacuum-based tissue grasper assembly is contemplated. The vacuum-based grasper assembly is also capable of grasping and pulling a large section of a generally slippery, polyp sufficient for a full transmural resection with a large margin.

The vacuum-based tissue grasper assembly is shown in FIGS. 75-79C to which reference is now made.

Figure 75:
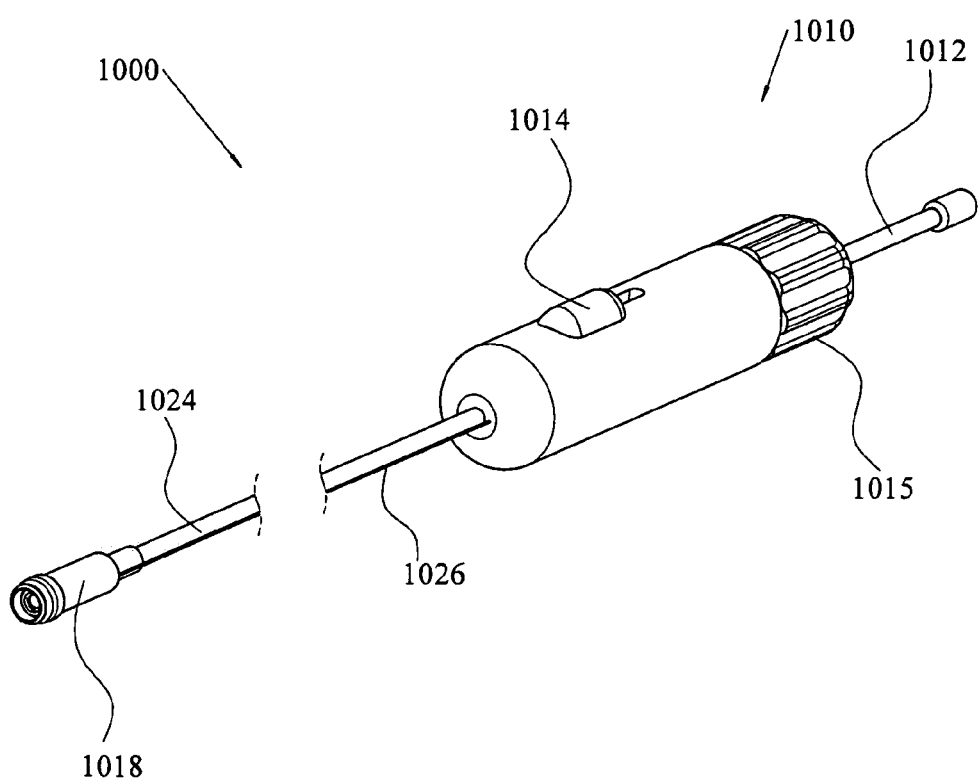
FIG. 75 shows a schematic overall view of a vacuum-based tissue grasper assembly of the present invention.

FIG. 75 shows a schematic overview of the vacuum grasper assembly. The assembly 1000 includes an assembly body 1010 which further includes a vacuum cup advancer control 1015 and an articulation wire control 1014. A tube 1012 is joined to assembly body 1010 and to a suction source (not shown). Tube 1012 is joined to the proximal side of assembly body 1010. On the distal side of assembly body 1010 is a connector tube 1024 to which is attached an articulation wire 1026. At the most distal end of connector tube 1024 is vacuum cup cover 1018. Not shown are buttons activating the suction source, a water source if required, or any other necessary auxiliary instruments.

Figure 76:
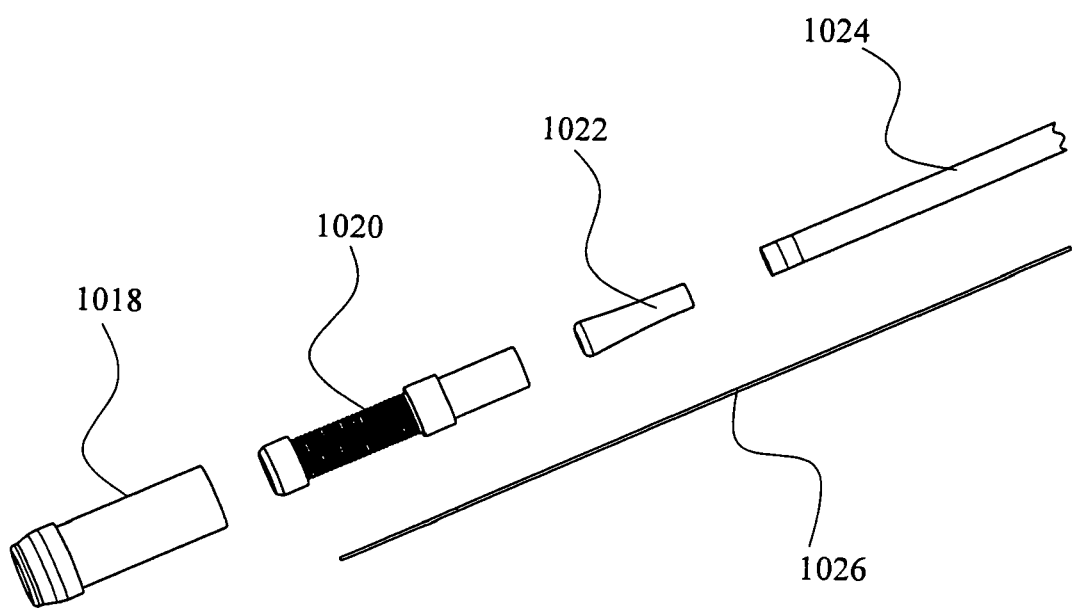
FIG. 76 shows an exploded view of the distal portion of the vacuum-based tissue grasper assembly in FIG. 75.
Figure 77B:
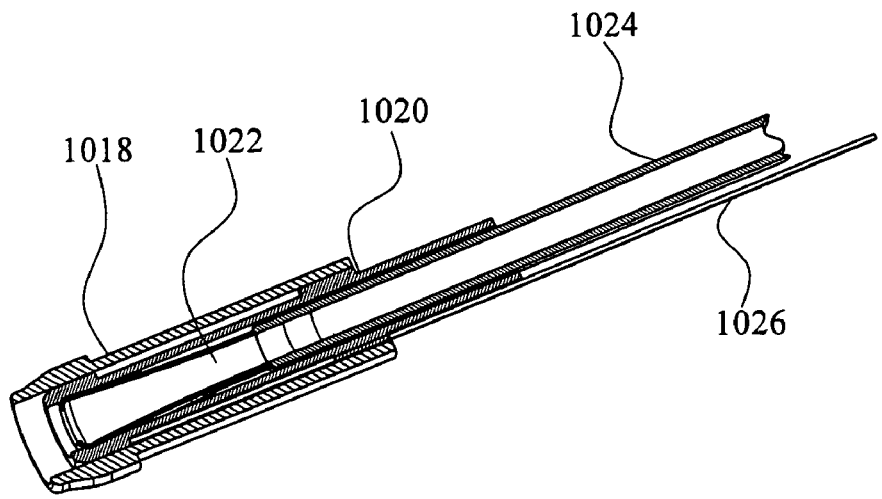
FIGS. 77A and 77B show a schematic view and a cut-away view, respectively, of the distal end of the vacuum-based tissue grasper assembly in FIG. 75.
Figure 77A:
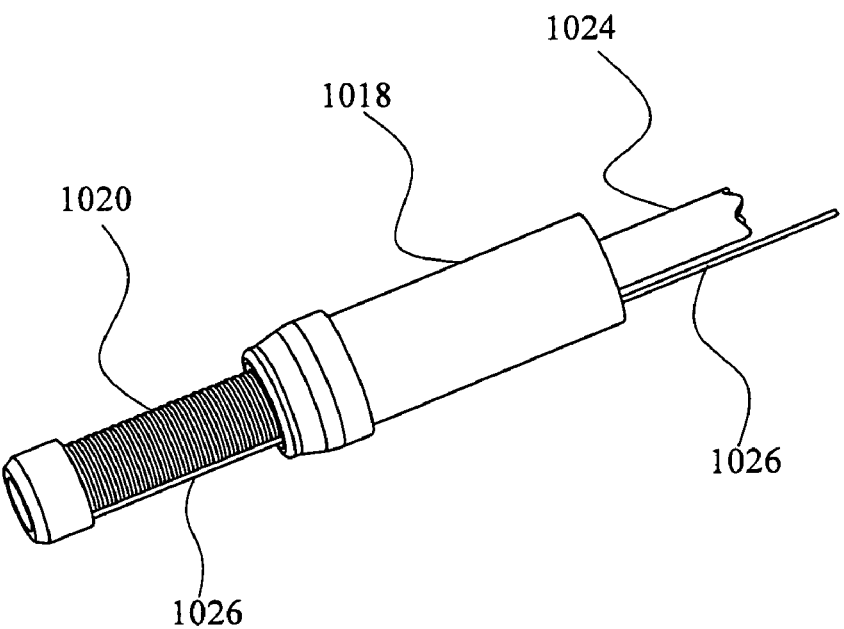

FIG. 76, to which reference is now made, shows an exploded view of the distal end of vacuum-based grasper assembly 1000 shown in FIG. 75. In FIG. 76, connector tube 1024, vacuum cup 1022 in its collapsed position, cup transporter 1020, and vacuum cup cover 1018 are shown. Also shown is articulation wire 1026. FIG. 77A shows a partially extended cup transporter 1020 projecting past vacuum cup cover 1018. FIG. 77B shows a cut away view of the distal portion of assembly 1000 before cup transporter 1020 is extended to allow for the emergence of collapsed vacuum cup 1022 and its transition to its non-collapsed position.

Figure 78A:
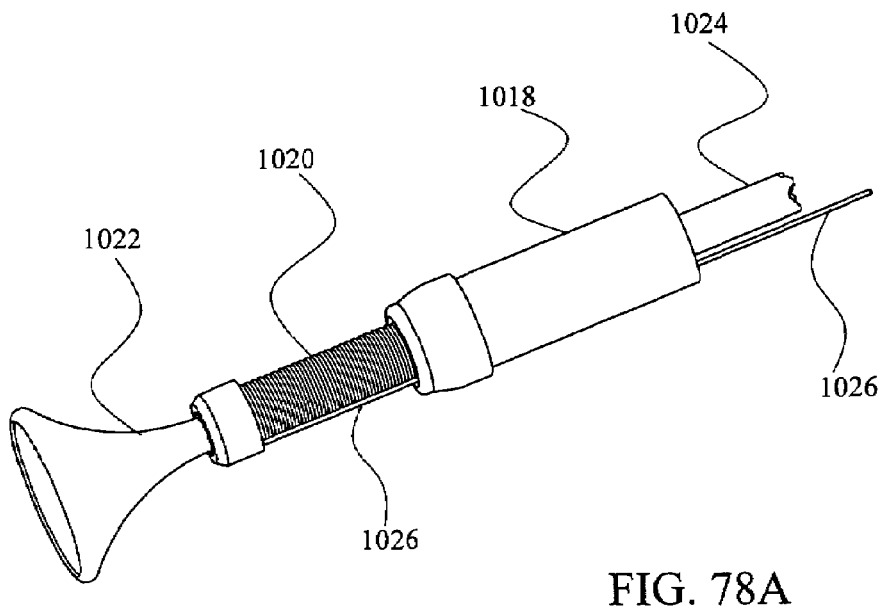
FIGS. 78A and 78B show two schematic views of a vacuum cup emerging from the distal end of the vacuum-based tissue grasper assembly with FIG. 78B showing the cup being turned toward a lesion (not shown)
Figure 78B:
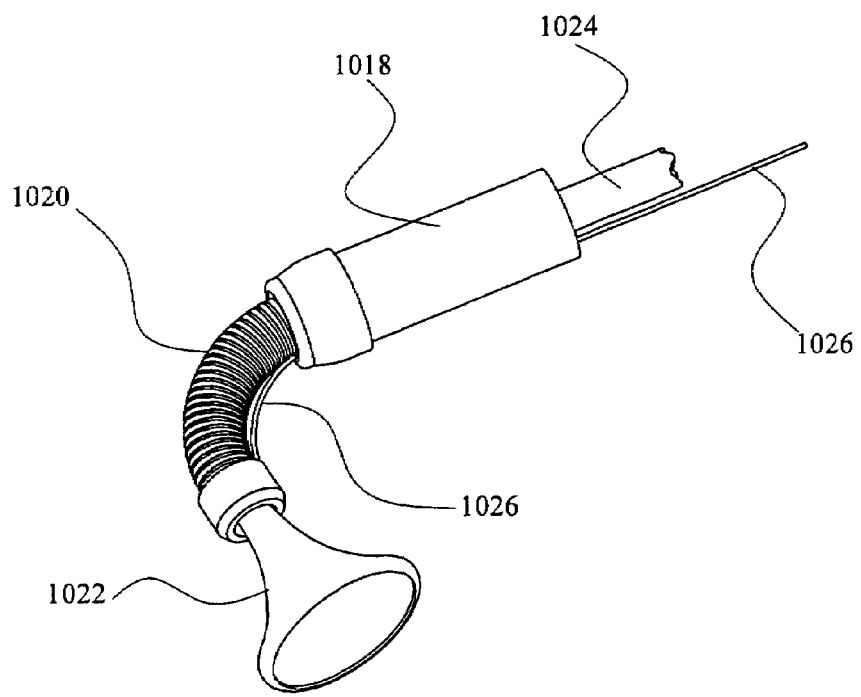
Figure 78C:
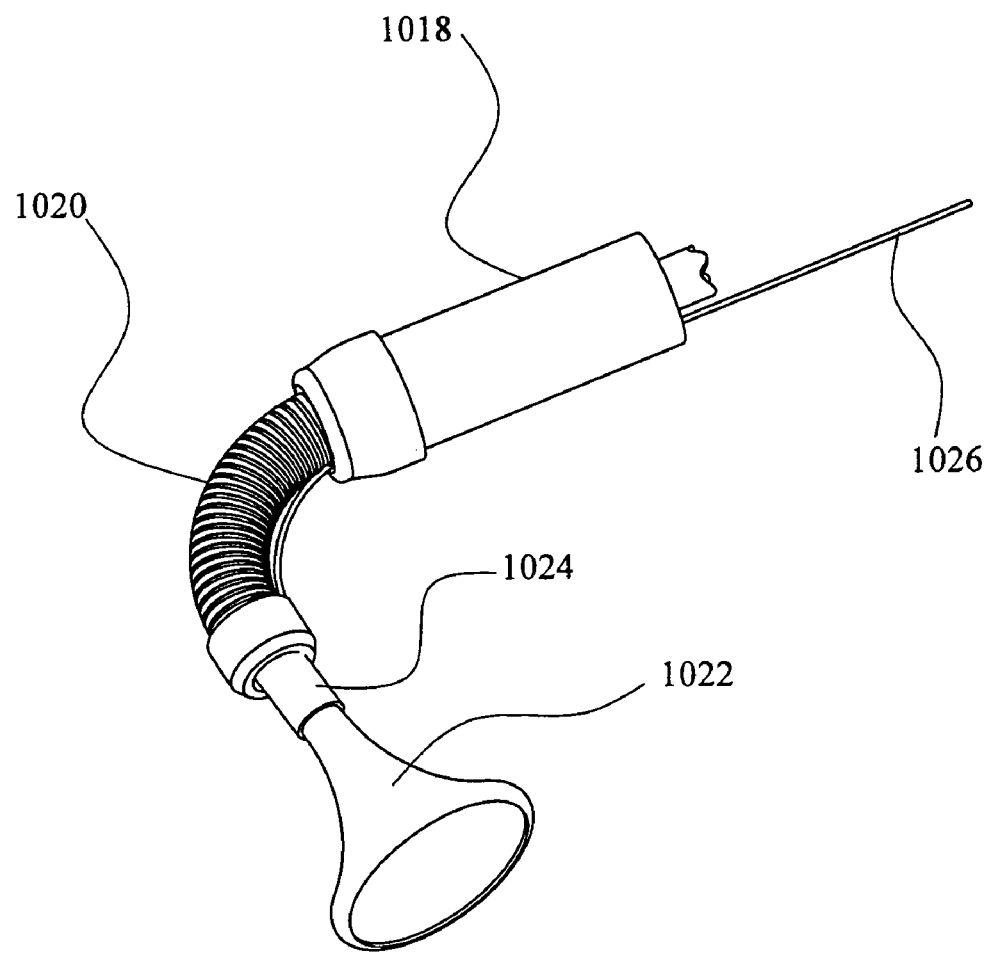
FIG. 78C shows a schematic view of the vacuum cup extending even further from the distal end of the vacuum-based tissue grasper assembly.

FIGS. 78A-78C show various stages of vacuum cup 1022 emerging from vacuum cup cover 1018 with cup transporter 1020 also at various stages of projecting past vacuum cup cover 1018. Articulation wire 1026 is joined to cup transporter 1020 (best seen in FIGS. 77A, 77B and 78A) and the results of its operation can best be seen in FIG. 78C.

Figure 79A:
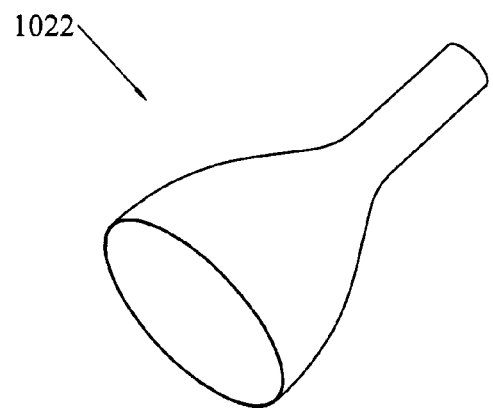
FIG. 79A shows a schematic view of the vacuum cup of the vacuum-based tissue grasper assembly shown in FIG. 75.
Figure 79B:
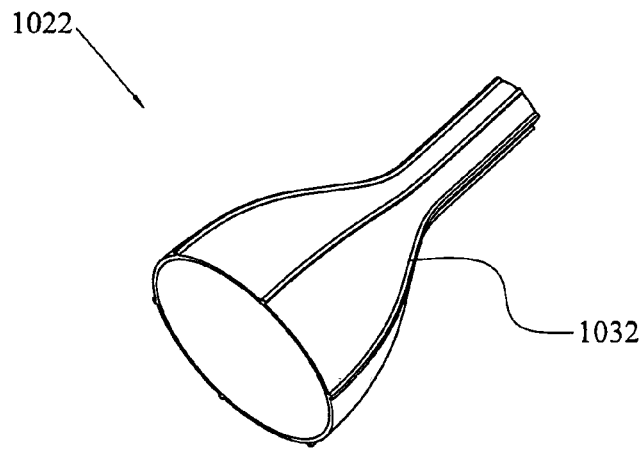
FIG. 79B shows a schematic view of a ribbed embodiment of the vacuum cup of the vacuum-based tissue grasper assembly shown in FIG. 75.
Figure 79C:
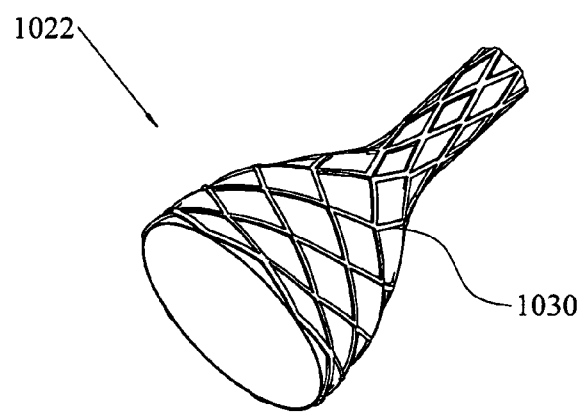
FIG. 79C shows a schematic view of the vacuum cup of the vacuum-based tissue grasper assembly shown in FIG. 75 supported by a stent-like structure.

Typically, but without intending to be limiting, vacuum cup 1022 is cup-shaped as in FIGS. 79A-79C. FIG. 79A shows an unsupported cup typically formed of a flexible plastic. FIGS. 79B and 79C show supported cups; in 79B the support are ribs 1032 either formed of resilient plastic or metal. Ribs 1032 may even be formed of the same plastic from which vacuum cup 1022 itself is formed. FIG. 79C shows the supporting structure to be a resilient stent-like structure 1030.

Typically vacuum cup 1022 is formed of a resilient plastic such as polyurethane, polyvinyl chloride, or other medical grade polymeric materials. The other parts of vacuum-based grasper assembly 1000 are formed of polymeric plastics, metals or a combination of both. Cup transporter 1020 is formed as a spring having an inner coating for reducing friction between itself and vacuum cup 1022. The spring allows for easier articulation of the vacuum cup 1022 when manipulated by articulation wire 1026. Flexible plastic tubes, specially cut metal tubes, and even tubes made from Ni—Ti alloys can be used as alternatives to a spring for allowing easier articulation. The materials noted above are exemplary only and not intended to be limiting.

As can be seen in FIGS. 80-83, to which reference is now made, the method for using vacuum-based grasper assembly 1000 of FIGS. 75-79C for effecting full transmural resection is very similar to that discussed in conjunction with FIGS. 60-74B where a mechanical tissue grasper is used. These latter Figures will again be referred to in the discussion of the method of use of the vacuum-based grasper assembly. It should be understood that in FIGS. 60-74B referred to below, the mechanical grasper assembly shown therein is replaced by vacuum-based grasper assembly 1000 of FIGS. 75-79C mutatis mutandis.

FIG. 57 shows an endoscope insertion shaft 300 with a working channel 154. It also contains several auxiliary elements, here three, denoted as 157A-157C. The number of working and auxiliary channels may be more or less than three in other embodiments of shaft 300. A multi-lumen plastic sleeve 150 is brought to and over endoscope insertion shaft 300 (FIG. 58). The endoscope insertion shaft 300 is encased in the primary lumen 155 of the multi-lumen sleeve 150. The one or more secondary lumens 158 of sleeve 150 are typically collapsed and, if needed, held by bands 160 (FIGS. 59A and 59B). The bands 160 are expandable when working instruments are inserted into the collapsed secondary lumens 158. Insertion of these instruments occurs after the distal end 152 of the endoscope shaft 300 is positioned proximate to the suspect lesion. Bands may not be required in some embodiments, if the secondary lumens 158 remain collapsed by themselves while the encased endoscope insertion shaft 300 (FIGS. 59A and 59B) is inserted into a body organ or if not required by the physician. It is to be understood that means or methods other than bands may be used to ensure that the secondary lumens remain collapsed while the encased endoscope shaft is inserted into the body and positioned, near the suspect lesion.

The encased endoscope insertion shaft 300 is advanced within the body lumen until it nears the lesion, herein taken to be a polyp P in the gastrointestinal (GI) tract (FIG. 60).

Figure 80:
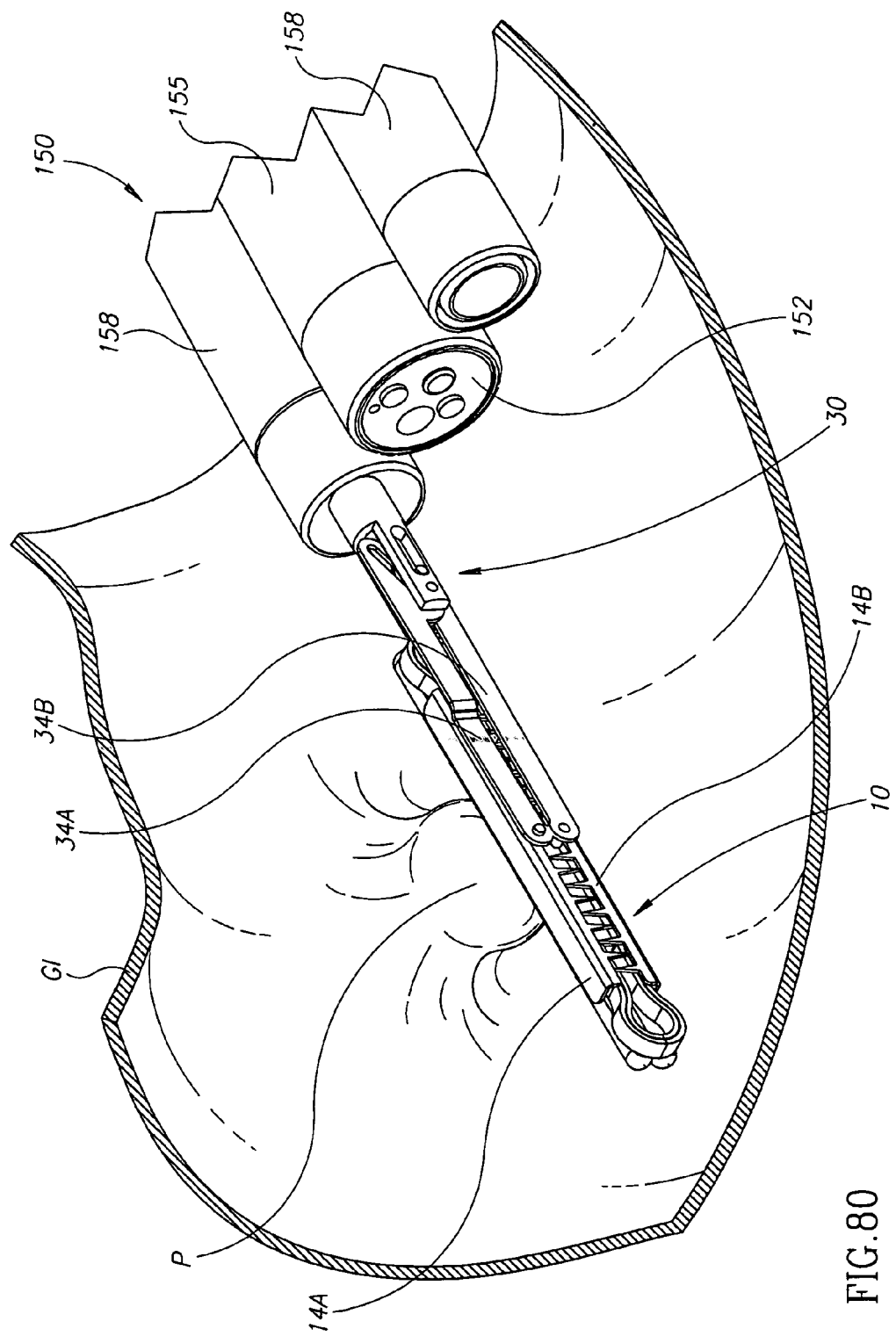
FIG. 80 shows a top side view of a surgical clip attached to an applier being positioned proximate to the polyp.

At that point, a surgical compression clip 10, and its attached applier 30, both in their closed positions, are advanced through a secondary lumen 158 of sleeve 150 to polyp P. Clip 10 exits the secondary lumen 158 still in its closed position (FIG. 61) and is brought into position adjacent to polyp P (FIG. 80).

Figure 81:
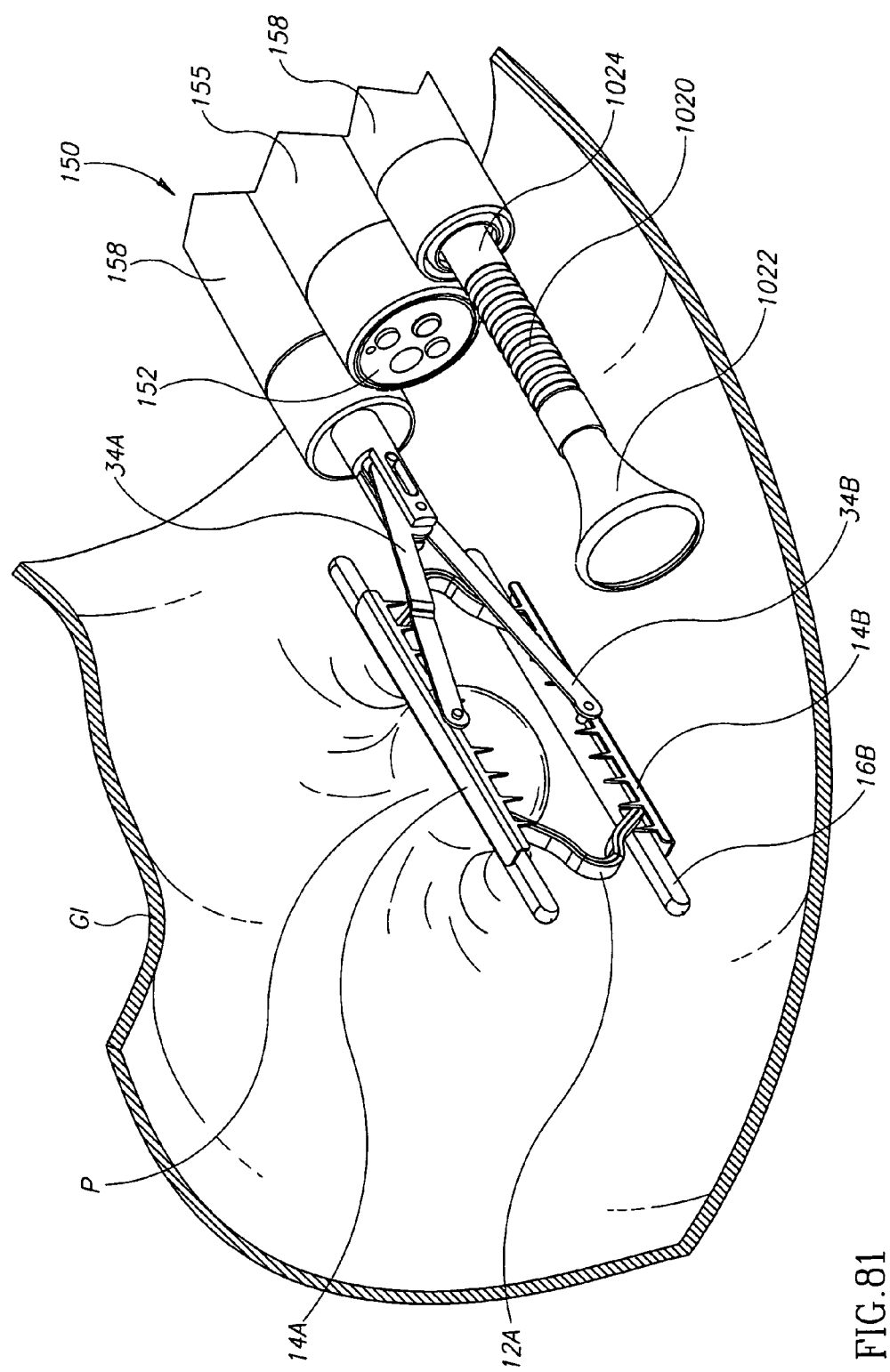
FIG. 81 shows a top side view of a surgical clip and applier positioned proximate to a polyp and a vacuum-based tissue grasper assembly being positioned proximate to the polyp after advancing through a secondary lumen of a multi-lumen sleeve.

A vacuum-based grasper assembly, such as the one discussed in conjunction with FIGS. 75-79C, is then inserted into a secondary lumen 158 of a multi-lumen sleeve 150, advanced through the lumen, and then advanced past the distal end 152 of endoscope insertion shaft 300 to the region adjacent to polyp P (FIG. 81).

In other embodiments, the grasper assembly is introduced via a working channel 154 of the endoscope insertion shaft and not through a secondary lumen 158 of the multi-lumen sleeve 150. From an operational point of view, this has no significant effect on the method described.

In yet another embodiment, the grasper assembly, clip 10 and clip applier 30 may be advanced through the same secondary lumen 158 from the proximal end of the endoscope shaft to the suspect lesion.

In yet another embodiment, the vacuum-based grasper assembly may be inserted into and advanced through a second working channel of the endoscopic insertion shaft.

Figure 82:
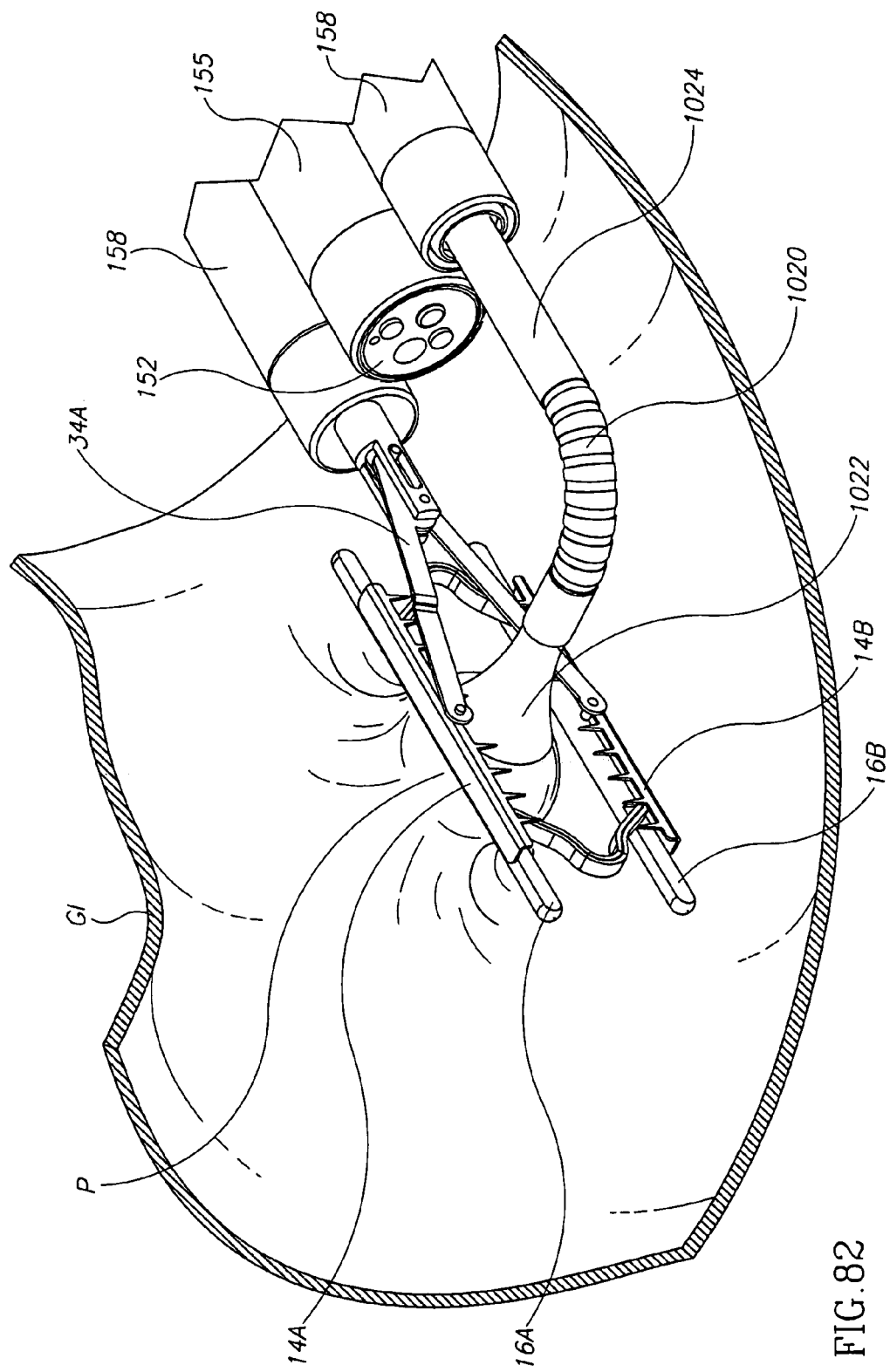
FIG. 82 shows a top side view of the vacuum cup of the vacuum-based tissue grasper assembly pulling the polyp through the opened clip shown in FIG. 81.
Figure 83:
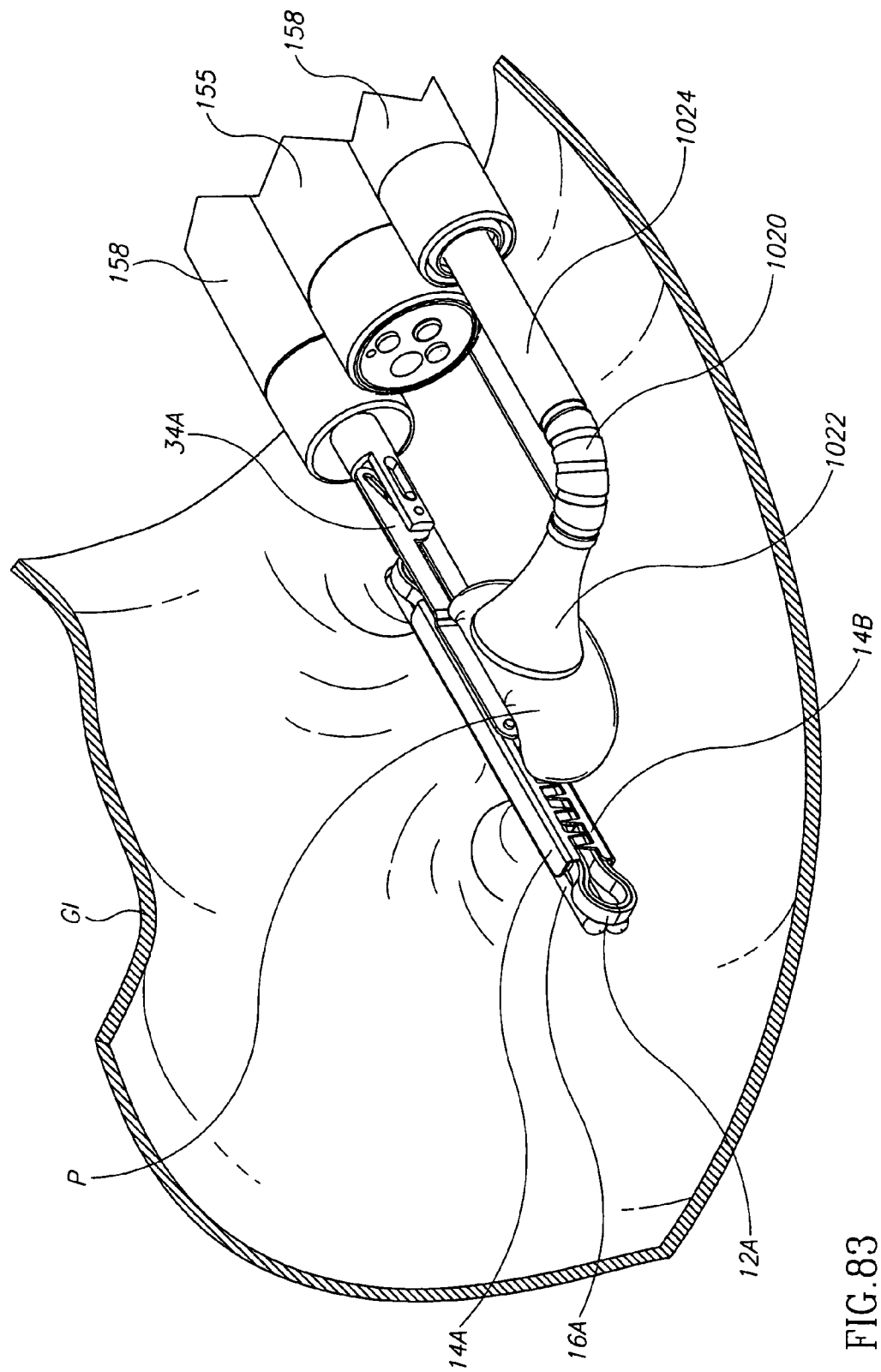
FIG. 83 shows a top side view of the surgical clip closed around the polyp, the polyp being pulled by the vacuum cup of the vacuum-based tissue grasper assembly.

Clip 10 is then opened by applier 30 so as to allow the pulling of polyp P through the clip. FIG. 81 shows an isometric view of this step. An articulation wire allows for maneuvering vacuum cup 1022 so that it can approach and grasp polyp P. In FIGS. 81-83 the articulation wire is obscured by vacuum cup 1022 and connector tube 1024.

Until clip 10 is opened and positioned close to polyp P, the grasper remains within connector tube 1024 inside lumen 158. After clip 10 is opened, vacuum cup 1022 advances out of lumen 158 and opens in stages similar to those shown in FIGS. 77A-78C. Using an articulation wire to maneuver flexible cup transporter 1020, here formed having a spring construction, vacuum cup 1022 is positioned to grasp polyp P through open clip 10 (FIG. 82).

Polyp P is then pulled by vacuum cup 1022 into separated compressing and securing elements 16A, 16B and 14A, 14B, respectively, of open clip 10. This is shown in a top side view in FIG. 823.

While what is described herein above refers to an articulation wire, any element capable of causing articulation of vacuum cup 1022 may also be used.

Unlike the mechanical grasper assembly discussed in conjunction with FIGS. 54-56 above, the vacuum-based grasper assembly does not necessarily require rotation of polyp P. The suction of the vacuum-based grasper assembly ensures that sufficient tissue is being maneuvered into clip 10 and brought near a severing device similar to severing device 310 (FIG. 72) to allow for full transmural resection.

Clip applier 30 then closes clip 10 around pulled polyp P (FIG. 83). Clip applier 30 is detached from the closed clip 10 and withdrawn via the secondary lumen 158 through which it entered (FIG. 71). Alternatively, if the physician feels it will assist him during the tissue resection, clip applier 30 can be detached from clip 10 after tissue resection.

Polyp P compressed by clip 10 is severed by a severing device 310 shown being positioned close to polyp P (FIG. 72). Severing device 310 may be advanced to the polyp through the endoscope's working channel 154 or through a secondary lumen 158 of sleeve; 150. In FIG. 72, severing device 310 has been advanced to its position for severing through the secondary lumen 158 used for advancing clip 10 and its applier 30. Severing device 310 approaches polyp P and severs it from the wall of the GI tract. The actual step of severing is not shown.

After severance of polyp P, the severed polyp held by the vacuum cup 1022 of the grasper, together with the remainder of the grasper assembly, the severing device 310 and the endoscope shaft, are retracted in the direction of the proximal end of the endoscope and withdrawn from the body. Withdrawal directly from the body organ is a straight-forward step, and therefore this step of the method is not presented in a separate Figure. Polyp P can then be biopsied or treated as needed by a physician.

The closed surgical compression clip 10 remains around that portion of the GI wall from which the tissue was resected (FIGS. 73, 74A and 74B). Compression continues until necrosis is induced and healing of the resected site occurs. Clip 10 is naturally expelled from the body through the rectum.

In the above discussion of the present invention, the invention has been described as being used in bowel polyp resections. It should be evident to one skilled in the art that other types of lesions, in other organs in other organ systems, can also be resected using the present invention with little or no modification. Such organs include, but are not limited to, the urinary bladder and other organs of the urinary tract, the uterus, the liver, the esophagus, the gall bladder, the lungs and the rectum.

In the above discussion, the system and method of the present invention have been described as being used in endoscopic procedures which do not require a direct incision into the body cavity. The system and method as described herein above has been described as being inserted into the body cavity through one of the body's existing orifices. However, it is readily understood by those skilled in the art that the system and method described herein above can be used in open surgical procedures with little or no modification, where the point of entry of the system is an incision into the body cavity.

It should be readily apparent to one skilled in the art that the device and method of the present invention can be used to excise animal tissue as well as human tissue, particularly, but without being limiting, tissue of other mammalian species.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

It will be appreciated by persons skilled in the art that the present invention is not limited by the drawings and description hereinabove presented. Rather, the invention is defined solely by the claims that follow.

The invention claimed is:

1. For use with a surgical compression clip comprising a pair of compression elements and at least one force applier element formed of a shape memory material, the clip having an open position and a closed position and configured to receive a full thickness of an organ wall portion therethrough when in its open position, the force applier element operative for providing a force to said compressing elements, and the compressing elements operative to apply a compression force to a full thickness of an organ wall portion when the clip is closed thereabout, so as to cause organ wall closure after resection of a portion thereof, a system for performing a full thickness resection of a portion of an organ wall comprising:
an endoscope having an insertion shaft having at least one channel and a distal end;
a multi-lumen sleeve having a primary lumen and at least one secondary lumen, said primary lumen encasing said endoscope insertion shaft so that there is no relative axial movement of said shaft with respect to said sleeve when said sleeve and shaft are positioned in a organ, and said at least one secondary lumen being in a collapsed configuration when said sleeve is inserted into the organ;
a clip applier for advancing the clip through a working conduit and for positioning the clip near the tissue to be resected, wherein said working conduit is a preselected one of (i) said at least one channel of said insertion shaft and (ii) said at least one secondary lumen of said multi-lumen sleeve;

a severing element for resecting tissue, selectably extendable through said working conduit so as to be brought into a position of operational proximity to tissue extending through the compression clip; and a grasper assembly which comprises;

a grasper portion having an open and a closed position;

an element having a bend for facilitating grasping the full thickness of an organ wall portion to be resected and pulling the wall portion in a direction out of the plane of the clip and said clip applier; and a transporting element, wherein said grasper portion and said element having a bend are selectably extendable through said working conduit being transported through said working conduit in said transporting element while said grasper portion is in its closed position and when said grasper portion exits said transporting element near the wall portion to be resected said grasper portion substantially immediately transitions to its open position, and wherein said severing element is operable to resect the full thickness of the portion of the organ wall extending through the clip.

2. A system for performing a full thickness resection of a portion of an organ wall according to claim 1, wherein said clip applier includes:

two arm elements selectably engageable with the compression clip, each arm element having a slot and a pin hole;

a position controlling element in mechanical communication with said arm elements, said position controlling element including a first and second pin, where said first pin passes through said pin hole on each of said two arm elements and said second pin passes through said slot on each of said arm elements; and an activating element in mechanical communication with and operable to move said pins in said position controlling element, thereby to produce substantially scissor-like motion of said arm elements bringing them from their closed adjacent position to their open spaced apart position and vice versa; and thereby to cause the compression clip to move from its open position to its closed position and vice versa in tandem with the motion of said arm elements of said clip applier.

3. A system for performing a full thickness resection of a portion of an organ wall according to claim 1, wherein the compression clip includes a threaded bolt inside a compression element, the threaded bolt having a receiving aperture, and said clip applier comprising:

a head element mateably insertable into the receiving aperture on the threaded bolt inside the compression element of the compression clip; and an activator for rotating said head element, thereby to cause the threaded bolt to rotate and the clip to move from its open position to its closed position and vice versa depending on the direction of rotation.

4. A system for performing a full thickness resection of a portion of an organ wall according to claim 1, wherein the compression clip includes a compression element and at least one connector element on each of two force applier elements, and wherein said clip applier includes:

two wires each connected to a connector element on a different one of the two force applier elements; and an anchor having an aperture positioned to plug an end of the compression element; and a pin passing through said aperture of said anchor, one of said wires being wound around said pin, whereby the compression clip moves from its closed position to its open position when said wires are pulled and moves to its closed position from its open position when said wires are released.

5. A system for performing a full thickness resection of a portion of an organ wall according to claim 1, wherein said grasper portion of said grasper assembly comprises:

forceps arms for grasping and pulling the portion of the organ wall to be resected; and said grasper assembly further includes:

a wire in mechanical connection with and for controlling and maneuvering said forceps arms and for bringing said forcep arms from their closed position to their open position and vice versa.

6. A system for performing a full thickness resection of a portion of an organ wall according to claim 5, wherein at least one of said wire and said forceps arms includes a bend, said bend facilitating grasping and pulling the organ wall to be resected through the clip.

7. A system for performing a full thickness resection of a portion of an organ wall according to claim 5, wherein at least one of said wire and said forceps arms is formed at least partially of a shape memory material.

8. A system for performing a full thickness resection of a portion of an organ wall according to claim 1, wherein said grasper portion of said grasper assembly comprises a flexible resilient vacuum cup having a closed and an open position; and said grasper assembly further includes:

a suction source for generating negative pressure;

a conduit joining said vacuum cup to said suction source; and articulation means for bringing said vacuum cup to the portion of the organ wall to be resected for engaging the tissue under a suction force.

9. A system for performing a full thickness resection of a portion of an organ wall, which comprises:

an endoscope having an insertion shaft having at least one channel;

a multi-lumen sleeve having a primary lumen encasing said endoscope insertion shaft, and at least one secondary lumen;

a compression clip having an open position and a closed position, said clip configured to receive a full thickness of an organ wall portion therethrough when in its open position, and operative to apply a compression force thereto when closed thereabout, so as to cause organ wall closure after resection of a portion thereof, said clip comprising:

a pair of generally elongated compressing elements for compressing the site of the portion of the organ wall to be resected;

at least one shape memory force applier element formed of shape memory material operative for providing a force to said pair of compressing elements for compressing the portion of the organ wall to be resected held therebetween; and a pair of generally elongated securing elements, wherein said at least one shape memory force applier element is positioned between, and in mechanical connection with, said operatively associated securing and compressing elements, and wherein said at least one shape memory force applier element and said pairs of securing and compressing elements all lie in substantially the same plane in both the first open and second closed positions of said clip and wherein a line of securing for holding the portion of the organ wall to be resected is formed by, and tangent to, said securing elements and a line of compression for compressing the portion of the organ wall to be resected is formed by, and tangent to said compression elements, the lines of securing and of compression not being collinear lines, and a clip applier for advancing said clip through a working conduit and for positioning said clip near the tissue to be resected, wherein said working conduit is a preselected one of (i) said at least one channel of said insertion shaft and (ii) said at least one secondary lumen of said multi-lumen sleeve and wherein said compressing elements are formed and configured for being disengageably joined to said clip applier;

a severing element for resecting tissue, selectably extendable through said working conduit so as to be brought into a position of operational proximity to tissue extending through said compression clip; and a grasper assembly selectably extendable through said working conduit, for engaging and pulling the full thickness of an organ wall portion through said clip when said clip is in its open position, wherein said severing element is operable to resect the full thickness of the portion of the organ wall extending through said clip.

10. A system for performing a full thickness resection of a portion of an organ wall according to claim 9, wherein said securing and compressing elements are generally linear elements.

11. A system for performing a full thickness resection of a portion of an organ wall according to claim 9, said pair of generally elongated securing elements each having formed thereon a pair of mutually opposing gripping portions adapted to secure therebetween the portion of the organ wall to be resected.

12. A system for performing a full thickness resection of a portion of an organ wall according to claim 11 wherein said gripping portions of said securing elements include toothed first edges which are in proximity to each other when said clip is in its closed position and wherein said toothed first edges of said securing elements are spaced apart from each other when said clip is in its open position.

13. A system for performing a full thickness resection of a portion of an organ wall according to claim 11, wherein said securing and compressing elements are substantially linear elements.

14. A system for performing a full thickness resection of a portion of an organ wall according to claim 9, wherein said grasper assembly is comprised of:

a grasper having a closed and an open position, said grasper comprised of:

forceps arms for grasping and pulling the portion of the organ wall to be resected; and a wire in mechanical connection with and for controlling and maneuvering said forceps arms and for bringing said forceps arms from their closed position to their open position and vice versa; and a grasper transporting element for transporting said grasper in its closed position to a location near the portion of the organ wall to be resected whereat said grasper is ejected from said transporting element allowing said forceps arms to open to their open position.

15. A system for performing a full thickness resection of a portion of an organ wall according to claim 14, wherein at least one of said wire and said forceps arms includes a bend, said bend facilitating grasping and pulling the organ wall to be resected through said clip.

16. A system for performing a full thickness resection of a portion of an organ wall according to claim 14, wherein at least one of said wire and said forceps arms is formed at least partially of a shape memory material.

17. A system for performing a full thickness resection of a portion of an organ wall according to claim 9, wherein said grasper assembly comprises:

a flexible resilient vacuum cup having a closed and an open position;

a suction source for generating negative pressure;

a conduit joining said vacuum cup to said suction source;

a grasper transporting element for transporting said vacuum cup in its closed position to a location near the portion of the organ wall to be resected where said vacuum cup is ejected from said transporting element allowing said vacuum cup to open to its open position; and articulation means for bringing said vacuum cup, when in its open position, to the portion of the organ wall to be resected for engaging the tissue under a suction force, and for subsequently pulling the tissue through said surgical clip.

18. For use with a surgical compression clip comprising a pair of compression elements and at least one force applier element formed of a shape memory material, the clip having an open position and a closed position and configured to receive a full thickness of an organ wall portion therethrough when in its open position, the force applier element operative for providing a force to said compressing elements, and the compressing elements operative to apply a compression force to a full thickness of an organ wall portion when the clip is closed thereabout, so as to cause organ wall closure after resection of a portion thereof, a system for performing a full thickness resection of a portion of an organ wall comprising:

an endoscope having an insertion shaft having at least one channel;

a multi-lumen sleeve having a primary lumen encasing said endoscope insertion shaft, and at least one secondary lumen;

a clip applier for advancing the clip through a working conduit and for positioning the clip near the tissue to be resected, wherein said working conduit is a preselected one of (i) said at least one channel of said insertion shaft and (ii) said at least one secondary lumen of said multi-lumen sleeve;

a severing element for resecting tissue, selectably extendable through said working conduit so as to be brought into a position of operational proximity to tissue extending through the compression clip; and a grasper assembly selectably extendable through said working conduit, for engaging and pulling the full thickness of an organ wall portion through the clip when the clip is in its open position, wherein said severing element is operable to resect the full thickness of the portion of the organ wall extending through the clip, and wherein said clip applier includes:

two arm elements selectably engageable with the compression clip, each arm element having a slot and a pin hole;

a position controlling element in mechanical communication with said arm elements, said position controlling element including a first and second pin, where said first pin passes through said pin hole on each of said two arm elements and said second pin passes through said slot on each of said arm elements; and an activating element in mechanical communication with and operable to move said pins in said position controlling element, thereby to produce substantially scissor-like motion of said arm elements bringing them from their closed adjacent position to their open spaced apart position and vice versa; and thereby to cause the compression clip to move from its open position to its closed position and vice versa in tandem with the motion of said arm elements of said clip applier.

19. A system for performing a full thickness resection of a portion of an organ wall, which comprises:

an endoscope having an insertion shaft having at least one channel;

a multi-lumen sleeve having a primary lumen encasing said endoscope insertion shaft, and at least one secondary lumen;

a compression clip having an open position and a closed position, said clip configured to receive a full thickness of an organ wall portion therethrough when in its open position, and operative to apply a compression force thereto when closed thereabout, so as to cause organ wall closure after resection of a portion thereof;

a clip applier for advancing said clip through a working conduit and for positioning said clip near the tissue to be resected, wherein said working conduit is a preselected one of (i) said at least one channel of said insertion shaft and (ii) said at least one secondary lumen of said multi-lumen sleeve;

a severing element for resecting tissue, selectably extendable through said working conduit so as to be brought into a position of operational proximity to tissue extending through said compression clip; and a grasper assembly selectably extendable through said working conduit, for engaging and pulling the full thickness of an organ wall portion through said clip when said clip is in its open position, wherein said severing element is operable to resect the full thickness of the portion of the organ wall extending through said clip, and wherein said clip further includes a pair of compressing elements and at least two shape memory force applier elements formed of shape memory material where one of said force applier elements is constructed as a latch which is operable to engage with an engagement means formed on one end of one of said pair of compressing elements, said latch thereby exerting a force on the portion of the organ wall to be resected when held between said compressing elements.

20. A system for performing a full thickness resection of a portion of an organ wall according to claim 19, wherein said clip further includes a wire.

21. A system for performing a full thickness resection of a portion of an organ wall, which comprises:

an endoscope having an insertion shaft having at least one channel;

a multi-lumen sleeve having a primary lumen encasing said endoscope insertion shaft, and at least one secondary lumen;

a compression clip having an open position and a closed position, said clip configured to receive a full thickness of an organ wall portion therethrough when in its open position, and operative to apply a compression force thereto when closed thereabout, so as to cause organ wall closure after resection of a portion thereof, said clip comprising:

a pair of generally elongated compressing elements for compressing the site of the portion of the organ wall to be resected held therebetween; and a pair of generally elongated securing elements operatively associated with said compressing elements, a clip applier for advancing said clip through a working conduit and for positioning said clip near the tissue to be resected, wherein said working conduit is a preselected one of (i) said at least one channel of said insertion shaft and (ii) said at least one secondary lumen of said multi-lumen sleeve and, said clip is formed and configured for being disengageably joined to said clip applier, and a severing element for resecting tissue, selectably extendable through said working conduit so as to be brought into a position of operational proximity to tissue extending through said compression clip; and a grasper assembly selectably extendable through said working conduit, for engaging and pulling the full thickness of an organ wall portion through said clip when said clip is in its open position, wherein said severing element is operable to resect the full thickness of the portion of the organ wall extending through said clip, wherein a line of securing for holding the portion of the organ wall to be resected is formed by, and tangent to, said securing elements and a line of compression for compressing the portion of the organ wall to be resected is formed by, and tangent to, said compression elements, the lines of securing and of compression not being collinear lines.

22. A system for performing a full thickness resection of a portion of an organ wall, which comprises:

an endoscope having an insertion shaft having at least one channel;

a multi-lumen sleeve having a primary lumen and at least one secondary lumen, said primary lumen encasing said endoscope insertion shaft so that there is no relative axial movement of said shaft with respect to said sleeve when said sleeve and shaft are positioned in a organ, said distal end of said shaft is substantially co-terminal with said sleeve, and said at least one secondary lumen being in a collapsed configuration when said sleeve is inserted into the organ;

a compression clip having an open position and a closed position, said clip configured to receive a full thickness of an organ wall portion therethrough when in its open position, and operative to apply a compression force thereto when closed thereabout, so as to cause organ wall closure after resection of a portion thereof;

a clip applier for advancing said clip through a working conduit and for positioning said clip near the tissue to be resected, wherein said working conduit is a preselected one of (i) said at least one channel of said insertion shaft and (ii) said at least one secondary lumen of said multi-lumen sleeve and wherein said compression clip is formed and configured for being disengageably joined to said clip applier;

a grasper assembly selectably extendable through said working conduit, said assembly includes an element having a bend for facilitating grasping the full thickness of an organ wall portion to be resected and pulling the wall portion in a direction out of the plane of the clip and said clip applier;

a severing element for resecting tissue, selectably extendable through said working conduit so as to be brought into a position of operational proximity to tissue extending through said compression clip,
wherein said severing element is operable to resect the full thickness of the portion of the organ wall extending through said clip.

23. A system according to claim 22, said clip comprising:
a pair of generally elongated compressing elements for compressing the site of the portion of the organ wall to be resected held therebetween; and
at least one force applier element formed of shape memory material operative for providing a force to said pair of compressing elements.

24. A system according to claim 1 wherein said element having a bend is chosen from at least one of the following: a grasper assembly actuator wire and forceps arms of a grasper assembly.

* * * * *